US011339385B2

(12) United States Patent
Sargent

(10) Patent No.: US 11,339,385 B2
(45) Date of Patent: May 24, 2022

(54) MODIFIED NUCLEIC ACID EDITING SYSTEMS FOR TETHERING DONOR DNA

(71) Applicant: GeneTether, Inc., San Francisco, CA (US)

(72) Inventor: Roy Geoffrey Sargent, San Lorenzo, CA (US)

(73) Assignee: GeneTether, Inc., San Francisco, CA (US)

( * ) Notice: Subject to any disclaimer, the term of this patent is extended or adjusted under 35 U.S.C. 154(b) by 477 days.

(21) Appl. No.: 16/363,642

(22) Filed: Mar. 25, 2019

(65) Prior Publication Data

US 2019/0309275 A1 Oct. 10, 2019

(51) Int. Cl.

| | |
|---|---|
| ***C12N 9/22*** | (2006.01) |
| ***C07K 14/47*** | (2006.01) |
| ***C12N 15/11*** | (2006.01) |
| ***A61K 38/00*** | (2006.01) |
| ***C12N 9/96*** | (2006.01) |
| ***C12N 15/90*** | (2006.01) |
| ***C12N 15/113*** | (2010.01) |
| ***C12N 15/62*** | (2006.01) |
| ***C12N 15/63*** | (2006.01) |

(52) U.S. Cl.

CPC ............ *C12N 9/22* (2013.01); *C07K 14/4703* (2013.01); *C12N 15/11* (2013.01); *A61K 38/00* (2013.01); *C07K 2319/80* (2013.01); *C12N 2310/20* (2017.05); *C12N 2800/80* (2013.01)

(58) Field of Classification Search

None

See application file for complete search history.

(56) References Cited

U.S. PATENT DOCUMENTS

| | | | |
|---|---|---|---|
| 2012/0324603 A1 | 12/2012 | Hlubek | |
| 2017/0058298 A1 | 3/2017 | Kennedy | |
| 2018/0250424 A1* | 9/2018 | Cotta-Ramusino | C12N 15/113 |

FOREIGN PATENT DOCUMENTS

| | | |
|---|---|---|
| WO | 2016057961 | 4/2016 |
| WO | 2016183448 | 11/2016 |

OTHER PUBLICATIONS

Aird, E. et al., "Increasing Cas9-mediated homology-directed repair efficiency through covalent tethering of DNA repair template", Commun Biol., 1:54, 6 pages, (2018).

Carlson-Stevermer, J. et al., "Assembly of CRISPR ribonucleoproteins with biotinylated oligonucleotides via an RNA aptamer for precise gene editing", Nat Commun., 8(1):1711, 13 pages, (2017).

International Application No. PCT/IB2019/052378; International Search Report and Written Opinion of the International Searching Authority, dated May 24, 2019; 11 pages.

Lee, K. et al., "Nanoparticle delivery of Cas9 ribonucleoprotein and donor DNA in vivo induces homology-directed DNA repair", Nat Biomed Eng., 1:889-901, (2017).

Lovendahl, K. et al., "Sequence-Directed Covalent Protein-DNA Linkages in a Single Step Using HUH-Tags", J Am Chem Soc., 139(20):7030-5, (2017).

Roche, P. et al., "Efficient Homology Directed Repair by Cas9: Donor Localization and Cationic Polymeric Transfection in Mammalian Cells", BiorRxiv, 48 pages, (2018).

Ruff, P. et al., "Aptamer-guided gene targeting in yeast and human cells", Nucleic Acids Res., 42(7):e61, 16 pages, (2014).

Ruff, P., "Protein-Assisted Targeting of Genes in Yeast and Human Cells", Dissertation, 162 pages, (2013).

Savic, N. et al., "Covalent linkage of the DNA repair template to the CRISPR-Cas9 nuclease enhances homology-directed repair", eLife, 7:e33761, 18 pages, (2018).

Aird, E. et al., "Enhancing CRISPR/Cas9 HDR Efficiency through Covalent Tethering of Donor DNA Template", XP055382604, https://cbitg.dl.umn.edu/sites/g/files/pua1691/f/webform/aird.pdf, Abstract, Jan. 1, 2016, 1 page.

Jasin, M. et al., "The Democratization of Gene Editing: Insights from Site-Specific Cleavage and Double-Strand Break Repair", DNA Repair, 44:6-16, (2016).

U.S. Appl. No. 17/531,450; Application as filed, filed Nov. 19, 2021; 34 pages.

* cited by examiner

*Primary Examiner* — Suzanne M Noakes
*Assistant Examiner* — Jae W Lee
(74) *Attorney, Agent, or Firm* — Dennis A. Bennett; Chris Marion; Stephanie M. Greer

(57) ABSTRACT

The technology relates to a composition for tethering donor DNA to a nuclease, the composition comprising a nucleic acid comprising donor DNA and a consensus sequence for a DNA binding domain; and at least one of: a fusion protein comprising a nuclease coupled to a DNA binding domain for binding the consensus sequence; and a nucleic acid encoding the fusion protein.

17 Claims, 19 Drawing Sheets

Specification includes a Sequence Listing.

SEQUENCE LISTING

```
<160> NUMBER OF SEQ ID NOS: 80

<210> SEQ ID NO 1
<211> LENGTH: 17
<212> TYPE: DNA
<213> ORGANISM: Artificial Sequence
<220> FEATURE:
<223> OTHER INFORMATION: GAL-4 binding site
<220> FEATURE:
<221> NAME/KEY: misc_feature
<222> LOCATION: (4)..(14)
<223> OTHER INFORMATION: n is a, c, g, or t

<400> SEQUENCE: 1

cggnnnnnnn nnnnccg                                                     17


<210> SEQ ID NO 2
<211> LENGTH: 13
<212> TYPE: DNA
<213> ORGANISM: Artificial Sequence
<220> FEATURE:
<223> OTHER INFORMATION: IHF binding site
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (7)..(10)
<223> OTHER INFORMATION: n is a, t, g, or c
<220> FEATURE:
<221> NAME/KEY: misc_feature
<222> LOCATION: (13)..(13)
<223> OTHER INFORMATION: r is a or g
<220> FEATURE:
<221> NAME/KEY: misc_feature
<222> LOCATION: (13)..(13)
<223> OTHER INFORMATION: r is a, or g

<400> SEQUENCE: 2

watcaannnn ttr                                                         13


<210> SEQ ID NO 3
<211> LENGTH: 13
<212> TYPE: PRT
<213> ORGANISM: Artificial Sequence
<220> FEATURE:
<223> OTHER INFORMATION: linker 1

<400> SEQUENCE: 3

Trp Ala Thr Cys Ala Ala Asn Asn Asn Asn Thr Thr Arg
1               5                   10


<210> SEQ ID NO 4
<211> LENGTH: 14
<212> TYPE: PRT
<213> ORGANISM: Artificial Sequence
<220> FEATURE:
<223> OTHER INFORMATION: linker 2

<400> SEQUENCE: 4

Glu Gly Lys Ser Ser Gly Ser Gly Ser Glu Ser Lys Ser Thr
1               5                   10


<210> SEQ ID NO 5
<211> LENGTH: 12
<212> TYPE: PRT
```

<213> ORGANISM: Artificial Sequence
<220> FEATURE:
<223> OTHER INFORMATION: linker 3

<400> SEQUENCE: 5

Gly Ser Ala Gly Ser Ala Ala Gly Ser Gly Glu Phe
1 5 10

<210> SEQ ID NO 6
<211> LENGTH: 18
<212> TYPE: PRT
<213> ORGANISM: Artificial Sequence
<220> FEATURE:
<223> OTHER INFORMATION: linker 4

<400> SEQUENCE: 6

Lys Glu Ser Gly Ser Val Ser Ser Glu Gln Leu Ala Gln Phe Arg Ser
1 5 10 15

Leu Glu

<210> SEQ ID NO 7
<211> LENGTH: 36
<212> TYPE: PRT
<213> ORGANISM: Artificial Sequence
<220> FEATURE:
<223> OTHER INFORMATION: linker 5

<400> SEQUENCE: 7

Gly Gly Ser Ala Gly Gly Ser Gly Ser Gly Ser Ser Gly Gly Ser Ser
1 5 10 15

Gly Ala Ser Gly Thr Gly Thr Ala Gly Gly Thr Gly Ser Gly Ser Gly
20 25 30

Thr Gly Ser Gly
35

<210> SEQ ID NO 8
<211> LENGTH: 5411
<212> TYPE: DNA
<213> ORGANISM: Artificial Sequence
<220> FEATURE:
<223> OTHER INFORMATION: lacI_Cas9 Range: 1 to 5361
<220> FEATURE:
<221> NAME/KEY: localisation cosing sequence
<222> LOCATION: (1)..(117)
<220> FEATURE:
<221> NAME/KEY: GGS linker coding sequence
<222> LOCATION: (118)..(126)
<220> FEATURE:
<221> NAME/KEY: lacI domian coding sequence
<222> LOCATION: (127)..(1209)
<220> FEATURE:
<221> NAME/KEY: XTEN linker coding sequence
<222> LOCATION: (1210)..(1257)
<220> FEATURE:
<221> NAME/KEY: Cas9 wild type protein coding sequence
<222> LOCATION: (1258)..(5361)

<400> SEQUENCE: 8
atggactaca aagaccatga cggtgattat aaagatcatg acatcgatta caaggatgac 60
gatgacaaga tggcccccaa gaagaagagg aaggtgggca ttcaccgcgg ggtacctgga 120
ggttctatga tgaagcccgt gaccctgtac gacgtggccg agtacgccgg cgtgagctac 180
cagaccgtga gccgcgtggt gaaccaggcc agccacgtga gcgccaagac ccgcgagaag 240
gtggaggccg ccatggccga gctgaactac atccccaacc gcgtggccca gcagctggcc 300
ggcaagcaga gcctgctgat cggcgtggcc accagcagcc tggccctgca cgcccccagc 360

-continued

```
cagatcgtgg ccgccatcaa gagccgcgcc gaccagctgg gcgccagcgt ggtggtgagc    420

atggtggagc gcagcggcgt ggaggcctgc aaggccgccg tgcacaacct gctggcccag    480

cgcgtgagcg gcctgatcat caactacccc ctggacgacc aggacgccat cgccgtggag    540

gccgcctgca ccaacgtgcc cgccctgttc ctggacgtga gcgaccagac ccccatcaac    600

agcatcatct tcagccacga ggacggcacc cgcctgggcg tggagcacct ggtggccctg    660

ggccaccagc agatcgccct gctggccggc cccctgagca gcgtgagcgc ccgcctgcgc    720

ctggccggct ggcacaagta cctgacccgc aaccagatcc agcccatcgc cgagcgcgag    780

ggcgactgga gcgccatgag cggcttccag cagaccatgc agatgctgaa cgagggcatc    840

gtgcccaccg ccatgctggt ggccaacgac cagatggccc tgggcgccat gcgcgccatc    900

accgagagcg gcctgcgcgt gggcgccgac atcagcgtgg tgggctacga cgacaccgag    960

gacagcagct gctacatccc ccccctgacc accatcaagc aggacttccg cctgctgggc   1020

cagaccagcg tggaccgcct gctgcagctg agccagggcc aggccgtgaa gggcaaccag   1080

ctgctgcccg tgagcctggt gaagcgcaag accaccctgg cccccaacac ccagaccgcc   1140

agcccccgcg ccctggccga cagcctgatg cagctggccc gccaggtgag ccgcctggag   1200

agcggccaga gcggcagcga gactcccggg acctcagagt ccgccacacc cgaaagtatg   1260

gataaaaagt attctattgg tttagctatc ggcactaatt ccgttggatg ggctgtcata   1320

accgatgaat acaaagtacc ttcaaagaaa tttaaggtgt tggggaacac agaccgtcat   1380

tcgattaaaa agaatcttat cggtgccctc ctattcgata gtggcgaaac ggcagaggcg   1440

actcgcctga aacgaaccgc tcggagaagg tatacacgtc gcaagaaccg aatatgttac   1500

ttacaagaaa tttttagcaa tgagatggcc aaagttgacg attctttctt tcaccgtttg   1560

gaagagtcct tccttgtcga agaggacaag aaacatgaac ggcaccccat ctttggaaac   1620

atagtagatg aggtggcata tcatgaaaag tacccaacga tttatcacct cagaaaaaag   1680

ctagttgact caactgataa agcggacctg aggttaatct acttggctct tgcccatatg   1740

ataaagttcc gtgggcactt tctcattgag ggtgatctaa atccggacaa ctcggatgtc   1800

gacaaactgt tcatccagtt agtacaaacc tataatcagt tgtttgaaga gaaccctata   1860

aatgcaagtg gcgtggatgc gaaggctatt cttagcgccc gcctctctaa atcccgacgg   1920

ctagaaaacc tgatcgcaca attacccgga gagaagaaaa atgggttgtt cggtaacctt   1980

atagcgctct cactaggcct gacaccaaat tttaagtcga acttcgactt agctgaagat   2040

gccaaattgc agcttagtaa ggacacgtac gatgacgatc tcgacaatct actggcacaa   2100

attggagatc agtatgcgga cttatttttg gctgccaaaa accttagcga tgcaatcctc   2160

ctatctgaca tactgagagt taatactgag attaccaagg cgccgttatc cgcttcaatg   2220

atcaaaaggt acgatgaaca tcaccaagac ttgacacttc tcaaggccct agtccgtcag   2280

caactgcctg agaaatataa ggaaatattc tttgatcagt cgaaaaacgg gtacgcaggt   2340

tatattgacg gcggagcgag tcaagaggaa ttctacaagt ttatcaaacc catattagag   2400

aagatggatg ggacggaaga gttgcttgta aaactcaatc gcgaagatct actgcgaaag   2460

cagcggactt tcgacaacgg tagcattcca catcaaatcc acttaggcga attgcatgct   2520

atacttagaa ggcaggagga tttttatccg ttcctcaaag acaatcgtga aaagattgag   2580

aaaatcctaa cctttcgcat accttactat gtgggacccc tggcccgagg gaactctcgg   2640

ttcgcatgga tgacaagaaa gtccgaagaa acgattactc catggaattt tgaggaagtt   2700
```

```
gtcgataaag gtgcgtcagc tcaatcgttc atcgagagga tgaccaactt tgacaagaat   2760
ttaccgaacg aaaaagtatt gcctaagcac agtttacttt acgagtattt cacagtgtac   2820
aatgaactca cgaaagttaa gtatgtcact gagggcatgc gtaaacccgc ctttctaagc   2880
ggagaacaga agaaagcaat agtagatctg ttattcaaga ccaaccgcaa agtgacagtt   2940
aagcaattga tcatctagac aataagttct ggttggcgtt tcactgtcaa ttcgttaact   3000
aagaggacta ctttaagaaa attgaatgct tcgattctgt cgagatctcc ggggtagaag   3060
atcgatttaa tgcgtcactt ggtacgtatc atgacctcct aaagataatt aaagataagg   3120
acttcctgga taacgaagag aatgaagata tcttagaaga tatagtgttg actcttaccc   3180
tctttgaaga tcgggaaatg attgaggaaa gactaaaaac atacgctcac ctgttcgacg   3240
ataaggttat gaaacagtta aagaggcgtc gctatacggg ctggggacga ttgtcgcgga   3300
aacttatcaa cgggataaga gacaagcaaa gtggtaaaac tattctcgat tttctaaaga   3360
gcgacggctt cgccaatagg aactttatgc agctgatcca tgatgactct ttaaccttca   3420
aagaggatat acaaaaggca caggtttccg gacaagggga ctcattgcac gaacatattg   3480
cgaatcttgc tggttcgcca gccatcaaaa agggcatact ccagacagtc aaagtagtgg   3540
atgagctagt taaggtcatg ggacgtcaca aaccggaaaa cattgtaatc gagatggcac   3600
gcgaaaatca aacgactcag aaggggcaaa aaaacagtcg agagcggatg aagagaatag   3660
aagagggtat taaagaactg ggcagccaga tcttaaagga gcatcctgtg gaaaataccc   3720
aattgcagaa cgagaaactt tacctctatt acctacaaaa tggaagggac atgtatgttg   3780
atcaggaact ggacataaac cgtttatctg attacgacgt cgatgccatt gtaccccaat   3840
cctttttgaa ggacgattca atcgacaata aagtgcttac acgctcggat aagaaccgag   3900
ggaaaagtga caatgttcca agcgaggaag tcgtaaagaa aatgaagaac tattggcggc   3960
agctcctaaa tgcgaaactg ataacgcaaa gaaagttcga taacttaact aaagctgaga   4020
ggggtggctt gtctgaactt gacaaggccg gatttattaa acgtcagctc gtggaaaccc   4080
gccaaatcac aaagcatgtt gcacagatac tagattcccg aatgaatacg aaatacgacg   4140
agaacgataa gctgattcgg gaagtcaaag taatcacttt aaagtcaaaa ttggtgtcgg   4200
acttcagaaa ggattttcaa ttctataaag ttagggagat aaataactac caccatgcgc   4260
acgacgctta tcttaatgcc gtcgtaggga ccgcactcat taagaaatac ccgaagctag   4320
aaagtgagtt tgtgtatggt gattacaaag tttatgacgt ccgtaagatg atcgcgaaaa   4380
gcgaacagga gataggcaag gctacagcca aatacttctt ttattctaac attatgaatt   4440
tctttaagac ggaaatcact ctggcaaacg gagagatacg caaacgacct ttaattgaaa   4500
ccaatgggga gacaggtgaa atcgtatggg ataagggccg ggacttcgcg acggtgagaa   4560
aagttttgtc catgccccaa gtcaacatag taaagaaaac tgaggtgcag accggagggt   4620
tttcaaagga atcgattctt ccaaaaagga atagtgataa gctcatcgct cgtaaaaagg   4680
actgggaccc gaaaaagtac ggtggcttcg atagccctac agttgcctat tctgtcctag   4740
tagtggcaaa agttgagaag ggaaaatcca agaaactgaa gtcagtcaaa gaattattgg   4800
ggataacgat tatggagcgc tcgtcttttg aaaagaaccc catcgacttc cttgaggcga   4860
aaggttacaa ggaagtaaaa aaggatctca taattaaact accaaagtat agtctgtttg   4920
agttagaaaa tggccgaaaa cggatgttgg ctagcgccgg agagcttcaa aaggggaacg   4980
aactcgcact accgtctaaa tacgtgaatt tcctgtattt agcgtcccat tacgagaagt   5040
tgaaaggttc acctgaagat aacgaacaga agcaactttt tgttgagcag cacaaacatt   5100
```

```
atctcgacga aatcatagag caaatttcgg aattcagtaa gagagtcatc ctagctgatg   5160

ccaatctgga caaagtatta agcgcataca acaagcacag ggataaaccc atacgtgagc   5220

aggcggaaaa tattatccat ttgtttactc ttaccaacct cggcgctcca gccgcattca   5280

agtattttga cacaacgata gatcgcaaac gatacacttc taccaaggag gtgctagacg   5340

cgacactgat tcaccaatcc atcacgggat tatatgaaac tcggatagat ttgtcacagc   5400

ttgggggtga c                                                        5411


<210> SEQ ID NO 9
<211> LENGTH: 1650
<212> TYPE: PRT
<213> ORGANISM: Artificial Sequence
<220> FEATURE:
<223> OTHER INFORMATION: lacI_Cas9 Range: 1 to 1787
<220> FEATURE:
<221> NAME/KEY: nuclear localization sequence
<222> LOCATION: (1)..(39)
<220> FEATURE:
<221> NAME/KEY: GGS linker
<222> LOCATION: (40)..(42)
<220> FEATURE:
<221> NAME/KEY: lacI domain
<222> LOCATION: (43)..(403)
<220> FEATURE:
<221> NAME/KEY: XTEN linker
<222> LOCATION: (404)..(419)
<220> FEATURE:
<221> NAME/KEY: Cas9 wild type
<222> LOCATION: (420)..(1650)

<400> SEQUENCE: 9

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Gly Gly Ser Met Met Lys Pro Val Thr
        35                  40                  45

Leu Tyr Asp Val Ala Glu Tyr Ala Gly Val Ser Tyr Gln Thr Val Ser
    50                  55                  60

Arg Val Val Asn Gln Ala Ser His Val Ser Ala Lys Thr Arg Glu Lys
65                  70                  75                  80

Val Glu Ala Ala Met Ala Glu Leu Asn Tyr Ile Pro Asn Arg Val Ala
                85                  90                  95

Gln Gln Leu Ala Gly Lys Gln Ser Leu Leu Ile Gly Val Ala Thr Ser
            100                 105                 110

Ser Leu Ala Leu His Ala Pro Ser Gln Ile Val Ala Ala Ile Lys Ser
        115                 120                 125

Arg Ala Asp Gln Leu Gly Ala Ser Val Val Val Ser Met Val Glu Arg
    130                 135                 140

Ser Gly Val Glu Ala Cys Lys Ala Ala Val His Asn Leu Leu Ala Gln
145                 150                 155                 160

Arg Val Ser Gly Leu Ile Ile Asn Tyr Pro Leu Asp Asp Gln Asp Ala
                165                 170                 175

Ile Ala Val Glu Ala Ala Cys Thr Asn Val Pro Ala Leu Phe Leu Asp
            180                 185                 190

Val Ser Asp Gln Thr Pro Ile Asn Ser Ile Ile Phe Ser His Glu Asp
        195                 200                 205

Gly Thr Arg Leu Gly Val Glu His Leu Val Ala Leu Gly His Gln Gln
    210                 215                 220
```

-continued

```
Ile Ala Leu Leu Ala Gly Pro Leu Ser Ser Val Ser Ala Arg Leu Arg
225                 230                 235                 240

Leu Ala Gly Trp His Lys Tyr Leu Thr Arg Asn Gln Ile Gln Pro Ile
                245                 250                 255

Ala Glu Arg Glu Gly Asp Trp Ser Ala Met Ser Gly Phe Gln Gln Thr
            260                 265                 270

Met Gln Met Leu Asn Glu Gly Ile Val Pro Thr Ala Met Leu Val Ala
        275                 280                 285

Asn Asp Gln Met Ala Leu Gly Ala Met Arg Ala Ile Thr Glu Ser Gly
    290                 295                 300

Leu Arg Val Gly Ala Asp Ile Ser Val Val Gly Tyr Asp Asp Thr Glu
305                 310                 315                 320

Asp Ser Ser Cys Tyr Ile Pro Pro Leu Thr Thr Ile Lys Gln Asp Phe
                325                 330                 335

Arg Leu Leu Gly Gln Thr Ser Val Asp Arg Leu Leu Gln Leu Ser Gln
            340                 345                 350

Gly Gln Ala Val Lys Gly Asn Gln Leu Leu Pro Val Ser Leu Val Lys
        355                 360                 365

Arg Lys Thr Thr Leu Ala Pro Asn Thr Gln Thr Ala Ser Pro Arg Ala
    370                 375                 380

Leu Ala Asp Ser Leu Met Gln Leu Ala Arg Gln Val Ser Arg Leu Glu
385                 390                 395                 400

Ser Gly Gln Ser Gly Ser Glu Thr Pro Gly Thr Ser Glu Ser Ala Thr
                405                 410                 415

Pro Glu Ser Met Asp Lys Lys Tyr Ser Ile Gly Leu Ala Ile Gly Thr
            420                 425                 430

Asn Ser Val Gly Trp Ala Val Ile Thr Asp Glu Tyr Lys Val Pro Ser
        435                 440                 445

Lys Lys Phe Lys Val Leu Gly Asn Thr Asp Arg His Ser Ile Lys Lys
    450                 455                 460

Asn Leu Ile Gly Ala Leu Leu Phe Asp Ser Gly Glu Thr Ala Glu Ala
465                 470                 475                 480

Thr Arg Leu Lys Arg Thr Ala Arg Arg Arg Tyr Thr Arg Arg Lys Asn
                485                 490                 495

Arg Ile Cys Tyr Leu Gln Glu Ile Phe Ser Asn Glu Met Ala Lys Val
            500                 505                 510

Asp Asp Ser Phe Phe His Arg Leu Glu Glu Ser Phe Leu Val Glu Glu
        515                 520                 525

Asp Lys Lys His Glu Arg His Pro Ile Phe Gly Asn Ile Val Asp Glu
    530                 535                 540

Val Ala Tyr His Glu Lys Tyr Pro Thr Ile Tyr His Leu Arg Lys Lys
545                 550                 555                 560

Leu Val Asp Ser Thr Asp Lys Ala Asp Leu Arg Leu Ile Tyr Leu Ala
                565                 570                 575

Leu Ala His Met Ile Lys Phe Arg Gly His Phe Leu Ile Glu Gly Asp
            580                 585                 590

Leu Asn Pro Asp Asn Ser Asp Val Asp Lys Leu Phe Ile Gln Leu Val
        595                 600                 605

Gln Thr Tyr Asn Gln Leu Phe Glu Glu Asn Pro Ile Asn Ala Ser Gly
    610                 615                 620

Val Asp Ala Lys Ala Ile Leu Ser Ala Arg Leu Ser Lys Ser Arg Arg
625                 630                 635                 640
```

-continued

```
Leu Glu Asn Leu Ile Ala Gln Leu Pro Gly Glu Lys Lys Asn Gly Leu
                645                 650                 655

Phe Gly Asn Leu Ile Ala Leu Ser Leu Gly Leu Thr Pro Asn Phe Lys
            660                 665                 670

Ser Asn Phe Asp Leu Ala Glu Asp Ala Lys Leu Gln Leu Ser Lys Asp
        675                 680                 685

Thr Tyr Asp Asp Asp Leu Asp Asn Leu Leu Ala Gln Ile Gly Asp Gln
    690                 695                 700

Tyr Ala Asp Leu Phe Leu Ala Ala Lys Asn Leu Ser Asp Ala Ile Leu
705                 710                 715                 720

Leu Ser Asp Ile Leu Arg Val Asn Thr Glu Ile Thr Lys Ala Pro Leu
                725                 730                 735

Ser Ala Ser Met Ile Lys Arg Tyr Asp Glu His His Gln Asp Leu Thr
            740                 745                 750

Leu Leu Lys Ala Leu Val Arg Gln Gln Leu Pro Glu Lys Tyr Lys Glu
        755                 760                 765

Ile Phe Phe Asp Gln Ser Lys Asn Gly Tyr Ala Gly Tyr Ile Asp Gly
    770                 775                 780

Gly Ala Ser Gln Glu Glu Phe Tyr Lys Phe Ile Lys Pro Ile Leu Glu
785                 790                 795                 800

Lys Met Asp Gly Thr Glu Glu Leu Leu Val Lys Leu Asn Arg Glu Asp
                805                 810                 815

Leu Leu Arg Lys Gln Arg Thr Phe Asp Asn Gly Ser Ile Pro His Gln
            820                 825                 830

Ile His Leu Gly Glu Leu His Ala Ile Leu Arg Arg Gln Glu Asp Phe
        835                 840                 845

Tyr Pro Phe Leu Lys Asp Asn Arg Glu Lys Ile Glu Lys Ile Leu Thr
    850                 855                 860

Phe Arg Ile Pro Tyr Tyr Val Gly Pro Leu Ala Arg Gly Asn Ser Arg
865                 870                 875                 880

Phe Ala Trp Met Thr Arg Lys Ser Glu Glu Thr Ile Thr Pro Trp Asn
                885                 890                 895

Phe Glu Glu Val Val Asp Lys Gly Ala Ser Ala Gln Ser Phe Ile Glu
            900                 905                 910

Arg Met Thr Asn Phe Asp Lys Asn Leu Pro Asn Glu Lys Val Leu Pro
        915                 920                 925

Lys His Ser Leu Leu Tyr Glu Tyr Phe Thr Val Tyr Asn Glu Leu Thr
    930                 935                 940

Lys Val Lys Tyr Val Thr Glu Gly Met Arg Lys Pro Ala Phe Leu Ser
945                 950                 955                 960

Gly Glu Gln Lys Lys Ala Ile Val Asp Leu Leu Phe Lys Thr Asn Arg
                965                 970                 975

Lys Val Thr Val Lys Gln Leu Lys Glu Asp Tyr Phe Lys Lys Ile Glu
            980                 985                 990

Cys Phe Asp Ser Val Glu Ile Ser  Gly Val Glu Asp Arg  Phe Asn Ala
        995                 1000                1005

Ser Leu  Gly Thr Tyr His Asp  Leu Leu Lys Ile Ile  Lys Asp Lys
    1010                1015                1020

Asp Phe  Leu Asp Asn Glu Glu  Asn Glu Asp Ile Leu  Glu Asp Ile
    1025                1030                1035

Val Leu  Thr Leu Thr Leu Phe  Glu Asp Arg Glu Met  Ile Glu Glu
    1040                1045                1050

Arg Leu  Lys Thr Tyr Ala His  Leu Phe Asp Asp Lys  Val Met Lys
```

```
    1055                1060                1065

Gln Leu  Lys Arg Arg Arg Tyr  Thr Gly Trp Gly Arg  Leu Ser Arg
    1070                1075                1080

Lys Leu  Ile Asn Gly Ile Arg  Asp Lys Gln Ser Gly  Lys Thr Ile
    1085                1090                1095

Leu Asp  Phe Leu Lys Ser Asp  Gly Phe Ala Asn Arg  Asn Phe Met
    1100                1105                1110

Gln Leu  Ile His Asp Asp Ser  Leu Thr Phe Lys Glu  Asp Ile Gln
    1115                1120                1125

Lys Ala  Gln Val Ser Gly Gln  Gly Asp Ser Leu His  Glu His Ile
    1130                1135                1140

Ala Asn  Leu Ala Gly Ser Pro  Ala Ile Lys Lys Gly  Ile Leu Gln
    1145                1150                1155

Thr Val  Lys Val Val Asp Glu  Leu Val Lys Val Met  Gly Arg His
    1160                1165                1170

Lys Pro  Glu Asn Ile Val Ile  Glu Met Ala Arg Glu  Asn Gln Thr
    1175                1180                1185

Thr Gln  Lys Gly Gln Lys Asn  Ser Arg Glu Arg Met  Lys Arg Ile
    1190                1195                1200

Glu Glu  Gly Ile Lys Glu Leu  Gly Ser Gln Ile Leu  Lys Glu His
    1205                1210                1215

Pro Val  Glu Asn Thr Gln Leu  Gln Asn Glu Lys Leu  Tyr Leu Tyr
    1220                1225                1230

Tyr Leu  Gln Asn Gly Arg Asp  Met Tyr Val Asp Gln  Glu Leu Asp
    1235                1240                1245

Ile Asn  Arg Leu Ser Asp Tyr  Asp Val Asp Ala Ile  Val Pro Gln
    1250                1255                1260

Ser Phe  Leu Lys Asp Asp Ser  Ile Asp Asn Lys Val  Leu Thr Arg
    1265                1270                1275

Ser Asp  Lys Asn Arg Gly Lys  Ser Asp Asn Val Pro  Ser Glu Glu
    1280                1285                1290

Val Val  Lys Lys Met Lys Asn  Tyr Trp Arg Gln Leu  Leu Asn Ala
    1295                1300                1305

Lys Leu  Ile Thr Gln Arg Lys  Phe Asp Asn Leu Thr  Lys Ala Glu
    1310                1315                1320

Arg Gly  Gly Leu Ser Glu Leu  Asp Lys Ala Gly Phe  Ile Lys Arg
    1325                1330                1335

Gln Leu  Val Glu Thr Arg Gln  Ile Thr Lys His Val  Ala Gln Ile
    1340                1345                1350

Leu Asp  Ser Arg Met Asn Thr  Lys Tyr Asp Glu Asn  Asp Lys Leu
    1355                1360                1365

Ile Arg  Glu Val Lys Val Ile  Thr Leu Lys Ser Lys  Leu Val Ser
    1370                1375                1380

Asp Phe  Arg Lys Asp Phe Gln  Phe Tyr Lys Val Arg  Glu Ile Asn
    1385                1390                1395

Asn Tyr  His His Ala His Asp  Ala Tyr Leu Asn Ala  Val Val Gly
    1400                1405                1410

Thr Ala  Leu Ile Lys Lys Tyr  Pro Lys Leu Glu Ser  Glu Phe Val
    1415                1420                1425

Tyr Gly  Asp Tyr Lys Val Tyr  Asp Val Arg Lys Met  Ile Ala Lys
    1430                1435                1440

Ser Glu  Gln Glu Ile Gly Lys  Ala Thr Ala Lys Tyr  Phe Phe Tyr
    1445                1450                1455
```

```
Ser Asn  Ile Met Asn Phe Phe  Lys Thr Glu Ile Thr  Leu Ala Asn
    1460                 1465                 1470

Gly Glu  Ile Arg Lys Arg Pro  Leu Ile Glu Thr Asn  Gly Glu Thr
    1475                 1480                 1485

Gly Glu  Ile Val Trp Asp Lys  Gly Arg Asp Phe Ala  Thr Val Arg
    1490                 1495                 1500

Lys Val  Leu Ser Met Pro Gln  Val Asn Ile Val Lys  Lys Thr Glu
    1505                 1510                 1515

Val Gln  Thr Gly Gly Phe Ser  Lys Glu Ser Ile Leu  Pro Lys Arg
    1520                 1525                 1530

Asn Ser  Asp Lys Leu Ile Ala  Arg Lys Lys Asp Trp  Asp Pro Lys
    1535                 1540                 1545

Lys Tyr  Gly Gly Phe Asp Ser  Pro Thr Val Ala Tyr  Ser Val Leu
    1550                 1555                 1560

Val Val  Ala Lys Val Glu Lys  Gly Lys Ser Lys Lys  Leu Lys Ser
    1565                 1570                 1575

Val Lys  Glu Leu Leu Gly Ile  Thr Ile Met Glu Arg  Ser Ser Phe
    1580                 1585                 1590

Glu Lys  Asn Pro Ile Asp Phe  Leu Glu Ala Lys Gly  Tyr Lys Glu
    1595                 1600                 1605

Val Lys  Lys Asp Leu Ile Ile  Lys Leu Pro Lys Tyr  Ser Leu Phe
    1610                 1615                 1620

Glu Leu  Glu Asn Gly Arg Lys  Arg Met Leu Ala Ser  Ala Gly Glu
    1625                 1630                 1635

Leu Gln  Lys Gly Asn Glu Leu  Ala Leu Pro Ser Lys
    1640                 1645                 1650
```

<210> SEQ ID NO 10
<211> LENGTH: 22
<212> TYPE: DNA
<213> ORGANISM: Artificial Sequence
<220> FEATURE:
<223> OTHER INFORMATION: CF1Bf primer sequence

<400> SEQUENCE: 10
ccttctctgt gaacctctat ca 22

<210> SEQ ID NO 11
<211> LENGTH: 20
<212> TYPE: DNA
<213> ORGANISM: Artificial Sequence
<220> FEATURE:
<223> OTHER INFORMATION: CF1f primer sequence

<400> SEQUENCE: 11
gcagagtacc tgaaacagga 20

<210> SEQ ID NO 12
<211> LENGTH: 20
<212> TYPE: DNA
<213> ORGANISM: Artificial Sequence
<220> FEATURE:
<223> OTHER INFORMATION: CF5r primer sequence

<400> SEQUENCE: 12
cattcacagt agcttaccca 20

<210> SEQ ID NO 13
<211> LENGTH: 20

<212> TYPE: DNA
<213> ORGANISM: Artificial Sequence
<220> FEATURE:
<223> OTHER INFORMATION: CF7Cr primer sequence

<400> SEQUENCE: 13
ataggaaaca ccaaagatga 20

<210> SEQ ID NO 14
<211> LENGTH: 20
<212> TYPE: DNA
<213> ORGANISM: Artificial Sequence
<220> FEATURE:
<223> OTHER INFORMATION: CF8Cr primer sequence

<400> SEQUENCE: 14
ataggaaaca ccaatgatat 20

<210> SEQ ID NO 15
<211> LENGTH: 40
<212> TYPE: DNA
<213> ORGANISM: Artificial Sequence
<220> FEATURE:
<223> OTHER INFORMATION: CF8Crfull primer

<400> SEQUENCE: 15
ataggaaaca ccaatgatat tttctttaat ggtgccaggc 40

<210> SEQ ID NO 16
<211> LENGTH: 41
<212> TYPE: DNA
<213> ORGANISM: Artificial Sequence
<220> FEATURE:
<223> OTHER INFORMATION: CF9Cf primer

<400> SEQUENCE: 16
gaaaatatca ttggtgtttc ctatgatgaa tatagataca g 41

<210> SEQ ID NO 17
<211> LENGTH: 19
<212> TYPE: DNA
<213> ORGANISM: Artificial Sequence
<220> FEATURE:
<223> OTHER INFORMATION: CF96250f primer

<400> SEQUENCE: 17
tgagttagat gtttgacgc 19

<210> SEQ ID NO 18
<211> LENGTH: 31
<212> TYPE: DNA
<213> ORGANISM: Artificial Sequence
<220> FEATURE:
<223> OTHER INFORMATION: CF96310f primer

<400> SEQUENCE: 18
gctgtgcatt ttcctctggg taatacttta g 31

<210> SEQ ID NO 19
<211> LENGTH: 24
<212> TYPE: DNA
<213> ORGANISM: Artificial Sequence
<220> FEATURE:
<223> OTHER INFORMATION: CF98236f primer

<400> SEQUENCE: 19
gtctctatta cttaatctgt acct 24

<210> SEQ ID NO 20
<211> LENGTH: 36
<212> TYPE: DNA
<213> ORGANISM: Artificial Sequence
<220> FEATURE:
<223> OTHER INFORMATION: CF98328f primer

<400> SEQUENCE: 20
ctgtgaagat taaataaatt aatatagtta aagcac 36

<210> SEQ ID NO 21
<211> LENGTH: 28
<212> TYPE: DNA
<213> ORGANISM: Artificial Sequence
<220> FEATURE:
<223> OTHER INFORMATION: CF99287r primer

<400> SEQUENCE: 21
atgctcattc cattaggcta tagtatta 28

<210> SEQ ID NO 22
<211> LENGTH: 26
<212> TYPE: DNA
<213> ORGANISM: Artificial Sequence
<220> FEATURE:
<223> OTHER INFORMATION: CF99310r primer

<400> SEQUENCE: 22
ctaattctct gctggcagat caatgc 26

<210> SEQ ID NO 23
<211> LENGTH: 34
<212> TYPE: DNA
<213> ORGANISM: Artificial Sequence
<220> FEATURE:
<223> OTHER INFORMATION: CF101310r primer

<400> SEQUENCE: 23
caagacgttg tgttaggtac attacatgta catc 34

<210> SEQ ID NO 24
<211> LENGTH: 28
<212> TYPE: DNA
<213> ORGANISM: Artificial Sequence
<220> FEATURE:
<223> OTHER INFORMATION: lacI Bbs Primer 2f

<400> SEQUENCE: 24
ctcccatgag gacggtacgc gactgggc 28

<210> SEQ ID NO 25
<211> LENGTH: 28
<212> TYPE: DNA
<213> ORGANISM: Artificial Sequence
<220> FEATURE:
<223> OTHER INFORMATION: lacI Bbs Primer 2r

<400> SEQUENCE: 25
gcccagtcgc gtaccgtcct catgggag 28

<210> SEQ ID NO 26
<211> LENGTH: 39
<212> TYPE: DNA
<213> ORGANISM: Artificial Sequence
<220> FEATURE:
<223> OTHER INFORMATION: lacI Bbs Primer 3f

<400> SEQUENCE: 26
gtgggatacg acgataccga ggacagctca tgttatatc 39

<210> SEQ ID NO 27
<211> LENGTH: 39
<212> TYPE: DNA
<213> ORGANISM: Artificial Sequence
<220> FEATURE:
<223> OTHER INFORMATION: lacI Bbs Primer 3r

<400> SEQUENCE: 27
gatataacat gagctgtcct cggtatcgtc gtatcccac 39

<210> SEQ ID NO 28
<211> LENGTH: 29
<212> TYPE: DNA
<213> ORGANISM: Artificial Sequence
<220> FEATURE:
<223> OTHER INFORMATION: lacI Primer 1f

<400> SEQUENCE: 28
atgaaaccag taacgttata cgatgtcgc 29

<210> SEQ ID NO 29
<211> LENGTH: 18
<212> TYPE: DNA
<213> ORGANISM: Artificial Sequence
<220> FEATURE:
<223> OTHER INFORMATION: lacI Primer 1r

<400> SEQUENCE: 29
tcactgcccg ctttccag 18

<210> SEQ ID NO 30
<211> LENGTH: 43
<212> TYPE: DNA
<213> ORGANISM: Artificial Sequence
<220> FEATURE:
<223> OTHER INFORMATION: lacI Primer 2f

<400> SEQUENCE: 30
ggtatccacg gagtcccagc agccatgaaa ccagtaacgt tat 43

<210> SEQ ID NO 31
<211> LENGTH: 23
<212> TYPE: DNA
<213> ORGANISM: Artificial Sequence
<220> FEATURE:
<223> OTHER INFORMATION: Primer 1f Age

<400> SEQUENCE: 31
ctggagcacc tgcctgaaat cac 23

<210> SEQ ID NO 32
<211> LENGTH: 27
<212> TYPE: DNA
<213> ORGANISM: Artificial Sequence
<220> FEATURE:
<223> OTHER INFORMATION: Primer 1fXba

<400> SEQUENCE: 32
cgcgtgcgcc aattctgcag acaaatg 27

<210> SEQ ID NO 33
<211> LENGTH: 34
<212> TYPE: DNA
<213> ORGANISM: Artificial Sequence
<220> FEATURE:
<223> OTHER INFORMATION: Primer 1r

<400> SEQUENCE: 33
tgctgggact ccgtggatac cgaccttccg cttc 34

<210> SEQ ID NO 34
<211> LENGTH: 43
<212> TYPE: DNA
<213> ORGANISM: Artificial Sequence
<220> FEATURE:
<223> OTHER INFORMATION: Primer 2f

<400> SEQUENCE: 34
ggtatccacg gagtcccagc agccgtgaaa ccagtaacgt tat 43

<210> SEQ ID NO 35
<211> LENGTH: 51
<212> TYPE: DNA
<213> ORGANISM: Artificial Sequence
<220> FEATURE:
<223> OTHER INFORMATION: Primer 2r

<400> SEQUENCE: 35
ggcggactct gaggtcccgg gagtctcgct gccgctctgc ccgctttcca g 51

<210> SEQ ID NO 36
<211> LENGTH: 49
<212> TYPE: DNA
<213> ORGANISM: Artificial Sequence
<220> FEATURE:
<223> OTHER INFORMATION: Primer 3f

<400> SEQUENCE: 36
cgggacctca gagtccgcca cacccgaaag tgacaagaag tacagcatc 49

<210> SEQ ID NO 37
<211> LENGTH: 26
<212> TYPE: DNA
<213> ORGANISM: Artificial Sequence
<220> FEATURE:
<223> OTHER INFORMATION: Primer 3r

<400> SEQUENCE: 37
cgtccacctt ggccatctcg ttgctg 26

<210> SEQ ID NO 38
<211> LENGTH: 58
<212> TYPE: DNA
<213> ORGANISM: Artificial Sequence
<220> FEATURE:
<223> OTHER INFORMATION: lacOsymCF1f primer

<400> SEQUENCE: 38
gttcggaata taaattgtga gcgctcacaa ttaagcttgc agagtacctg aaacagga 58

<210> SEQ ID NO 39
<211> LENGTH: 58
<212> TYPE: DNA
<213> ORGANISM: Artificial Sequence
<220> FEATURE:
<223> OTHER INFORMATION: lacOsymCF5r primer

<400> SEQUENCE: 39
gttcggaata taaattgtga gcgctcacaa ttaagcttca ttcacagtag cttaccca 58

<210> SEQ ID NO 40
<211> LENGTH: 59
<212> TYPE: DNA
<213> ORGANISM: Artificial Sequence
<220> FEATURE:
<223> OTHER INFORMATION: lacOsymCF5kf primer

<400> SEQUENCE: 40
gttcggaata taaattgtga gcgctcacaa ttaagcttgc tgtgcatttt cctctgggt 59

<210> SEQ ID NO 41
<211> LENGTH: 69
<212> TYPE: DNA
<213> ORGANISM: Artificial Sequence
<220> FEATURE:
<223> OTHER INFORMATION: lacOsymCF5kr primer

<400> SEQUENCE: 41
gttcggaata taaattgtga gcgctcacaa ttaagcttca agacgttgtg ttaggtacat 60
tacatgtac 69

<210> SEQ ID NO 42
<211> LENGTH: 58
<212> TYPE: DNA
<213> ORGANISM: Artificial Sequence
<220> FEATURE:
<223> OTHER INFORMATION: pUC19polyCF5kr primer

<400> SEQUENCE: 42
gaattcgagc tcggtacccg ggatcccaa gacgttgtgt taggtacatt acatgtac 58

<210> SEQ ID NO 43
<211> LENGTH: 47
<212> TYPE: DNA
<213> ORGANISM: Artificial Sequence
<220> FEATURE:
<223> OTHER INFORMATION: pUC19polyCF5r primer

<400> SEQUENCE: 43
gaattcgagc tcggtacccg ggatcccat tcacagtagc ttaccca 47

<210> SEQ ID NO 44
<211> LENGTH: 50
<212> TYPE: DNA
<213> ORGANISM: Artificial Sequence
<220> FEATURE:
<223> OTHER INFORMATION: tetOCF5kf primer

<400> SEQUENCE: 44
cactccctat cagtgataga gaaaagaaag ctgtgcattt tcctctgggt 50

<210> SEQ ID NO 45
<211> LENGTH: 58
<212> TYPE: DNA
<213> ORGANISM: Artificial Sequence
<220> FEATURE:
<223> OTHER INFORMATION: tetOCF5kr primer

<400> SEQUENCE: 45
cactccctat cagtgataga gaaacaagac gttgtgttag gtacattaca tgtacatc 58

<210> SEQ ID NO 46
<211> LENGTH: 46
<212> TYPE: DNA
<213> ORGANISM: Artificial Sequence
<220> FEATURE:
<223> OTHER INFORMATION: tetOCF1f primer

<400> SEQUENCE: 46
cactccctat cagtgataga gaaaaggcag agtacctgaa acagga 46

<210> SEQ ID NO 47
<211> LENGTH: 46
<212> TYPE: DNA
<213> ORGANISM: Artificial Sequence
<220> FEATURE:
<223> OTHER INFORMATION: tetOCF5r primer

<400> SEQUENCE: 47
cactccctat cagtgataga gaaaagcatt cacagtagct taccca 46

<210> SEQ ID NO 48
<211> LENGTH: 24
<212> TYPE: DNA
<213> ORGANISM: Artificial Sequence
<220> FEATURE:
<223> OTHER INFORMATION: 10635f primer

<400> SEQUENCE: 48
cggagcctat ggaaaaacgc cagc 24

<210> SEQ ID NO 49
<211> LENGTH: 25
<212> TYPE: DNA
<213> ORGANISM: Artificial Sequence
<220> FEATURE:
<223> OTHER INFORMATION: CFWT 130117 forward guide

<400> SEQUENCE: 49
caccgattaa agaaaatatc atctt 25

<210> SEQ ID NO 50
<211> LENGTH: 25
<212> TYPE: DNA
<213> ORGANISM: Artificial Sequence
<220> FEATURE:
<223> OTHER INFORMATION: CFWT 130117 fc guide

<400> SEQUENCE: 50
aaacaagatg atattttctt taatc 25

<210> SEQ ID NO 51
<211> LENGTH: 25
<212> TYPE: DNA
<213> ORGANISM: Artificial Sequence
<220> FEATURE:
<223> OTHER INFORMATION: CFWT 130121 rw guide

<400> SEQUENCE: 51
caccgaaaga tgatattttc tttaa 25

<210> SEQ ID NO 52
<211> LENGTH: 25
<212> TYPE: DNA
<213> ORGANISM: Artificial Sequence
<220> FEATURE:
<223> OTHER INFORMATION: CFWT 130121 rc guide

<400> SEQUENCE: 52
aaacttaaag aaaatatcat ctttc 25

<210> SEQ ID NO 53
<211> LENGTH: 25
<212> TYPE: DNA
<213> ORGANISM: Artificial Sequence
<220> FEATURE:
<223> OTHER INFORMATION: delF 130127 fw guide

<400> SEQUENCE: 53
caccgaccat taaagaaaat atcat 25

<210> SEQ ID NO 54
<211> LENGTH: 25
<212> TYPE: DNA
<213> ORGANISM: Artificial Sequence
<220> FEATURE:
<223> OTHER INFORMATION: delF 130127 fc guide

<400> SEQUENCE: 54
aaacatgata ttttctttaa tggtc 25

<210> SEQ ID NO 55
<211> LENGTH: 25
<212> TYPE: DNA
<213> ORGANISM: Artificial Sequence
<220> FEATURE:
<223> OTHER INFORMATION: delF 130138 rw guide

<400> SEQUENCE: 55
caccgaccaa tgatattttc tttaa 25

<210> SEQ ID NO 56
<211> LENGTH: 25
<212> TYPE: DNA
<213> ORGANISM: Artificial Sequence
<220> FEATURE:
<223> OTHER INFORMATION: del 130138 rc guide

<400> SEQUENCE: 56
aaacttaaag aaaatatcat tggtc 25

<210> SEQ ID NO 57
<211> LENGTH: 20
<212> TYPE: DNA
<213> ORGANISM: Artificial Sequence
<220> FEATURE:
<223> OTHER INFORMATION: lactose operator sequence

<400> SEQUENCE: 57
aattgtgagc gctcacaatt 20

<210> SEQ ID NO 58
<211> LENGTH: 24
<212> TYPE: DNA
<213> ORGANISM: Artificial Sequence
<220> FEATURE:
<223> OTHER INFORMATION: tetracycline operator sequence

<400> SEQUENCE: 58
cactccctat cagtgataga gaaa 24

<210> SEQ ID NO 59

<211> LENGTH: 42
<212> TYPE: DNA
<213> ORGANISM: Artificial Sequence
<220> FEATURE:
<223> OTHER INFORMATION: tetO w oligo

<400> SEQUENCE: 59
tcgagtttac cactccctat cagtgataga gaaaagtgaa ag 42

<210> SEQ ID NO 60
<211> LENGTH: 42
<212> TYPE: DNA
<213> ORGANISM: Artificial Sequence
<220> FEATURE:
<223> OTHER INFORMATION: tetO c oligo

<400> SEQUENCE: 60
tcgactttca cttttctcta tcactgatag ggagtggtaa ac 42

<210> SEQ ID NO 61
<211> LENGTH: 44
<212> TYPE: DNA
<213> ORGANISM: Artificial Sequence
<220> FEATURE:
<223> OTHER INFORMATION: lacO w oligo

<400> SEQUENCE: 61
tcgagtttag tggaattgtg agcggataac aatttcactg aaag 44

<210> SEQ ID NO 62
<211> LENGTH: 44
<212> TYPE: DNA
<213> ORGANISM: Artificial Sequence
<220> FEATURE:
<223> OTHER INFORMATION: lacO c oligo

<400> SEQUENCE: 62
tcgactttca gtgaaattgt tatccgctca caattccact aaac 44

<210> SEQ ID NO 63
<211> LENGTH: 10417
<212> TYPE: DNA
<213> ORGANISM: Artificial Sequence
<220> FEATURE:
<223> OTHER INFORMATION: pGT1

<400> SEQUENCE: 63
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg ggtcttcgag aagacctgtt ttagagctag aaatagcaag ttaaaataag 300
gctagtccgt tatcaacttg aaaaagtggc accgagtcgg tgcttttttg ttttagagct 360
agaaatagca agttaaaata aggctagtcc gtttttagcg cgtgcgccaa ttctgcagac 420
aaatggctct agaggtaccc gttacataac ttacggtaaa tggcccgcct ggctgaccgc 480
ccaacgaccc ccgcccattg acgtcaatag taacgccaat agggactttc cattgacgtc 540
aatgggtgga gtatttacgg taaactgccc acttggcagt acatcaagtg tatcatatgc 600
caagtacgcc ccctattgac gtcaatgacg gtaaatggcc cgcctggcat tgtgcccagt 660
acatgacctt atgggacttt cctacttggc agtacatcta cgtattagtc atcgctatta 720

```
ccatggtcga ggtgagcccc acgttctgct tcactctccc catctccccc ccctccccac    780
ccccaatttt gtatttattt atttttaat tattttgtgc agcgatgggg gcgggggggg    840
gggggggcg cgcgccaggc ggggcggggc ggggcgaggg gcggggcggg gcgaggcgga    900
gaggtgcggc ggcagccaat cagagcggcg cgctccgaaa gtttcctttt atggcgaggc    960
ggcggcggcg gcggccctat aaaaagcgaa gcgcgcggcg ggcgggagtc gctgcgacgc   1020
tgccttcgcc ccgtgccccg ctccgccgcc gcctcgcgcc gcccgccccg gctctgactg   1080
accgcgttac tcccacaggt gagcgggcgg gacggccctt ctcctccggg ctgtaattag   1140
ctgagcaaga ggtaagggtt taagggatgg ttggttggtg gggtattaat gtttaattac   1200
ctggagcacc tgcctgaaat cactttttt caggttggac cggtgccacc atggactata   1260
aggaccacga cggagactac aaggatcatg atattgatta caaagacgat gacgataaga   1320
tggccccaaa gaagaagcgg aaggtcggta tccacggagt cccagcagcc gtgaaaccag   1380
taacgttata cgatgtcgca gagtatgccg gtgtctctta tcagaccgtt tcccgcgtgg   1440
tgaaccaggc cagccacgtt tctgcgaaaa cgcgggaaaa agtggaagcg gcgatggcgg   1500
agctgaatta cattcccaac cgcgtggcac aacaactggc gggcaaacag tcgttgctga   1560
ttggcgttgc cacctccagt ctggccctgc acgcgccgtc gcaaattgtc gcggcgatta   1620
aatctcgcgc cgatcaactg ggtgccagcg tggtggtgtc gatggtagaa cgaagcggcg   1680
tcgaagcctg taaagcggcg gtgcacaatc ttctcgcgca acgcgtcagt gggctgatca   1740
ttaactatcc gctggatgac caggatgcca ttgctgtgga agctgcctgc actaatgttc   1800
cggcgttatt tcttgatgtc tctgaccaga cacccatcaa cagtattatt ttctcccatg   1860
aggacggtac gcgactgggc gtggagcatc tggtcgcatt gggtcaccag caaatcgcgc   1920
tgttagcggg cccattaagt tctgtctcgg cgcgtctgcg tctggctggc tggcataaat   1980
atctcactcg caatcaaatt cagccgatag cggaacggga aggcgactgg agtgccatgt   2040
ccggttttca acaaaccatg caaatgctga atgagggcat cgttcccact gcgatgctgg   2100
ttgccaacga tcagatggcg ctgggcgcaa tgcgcgccat taccgagtcc gggctgcgcg   2160
ttggtgcgga tatctcggta gtgggatacg acgataccga ggacagctca tgttatatcc   2220
cgccgttaac caccatcaaa caggattttc gcctgctggg gcaaaccagc gtggaccgct   2280
tgctgcaact ctctcagggc caggcggtga agggcaatca gctgttgccc gtctcactgg   2340
tgaaaagaaa aaccaccctg gcgcccaata cgcaaaccgc ctctccccgc gcgttggccg   2400
attcattaat gcagctggca cgacaggttt cccgactgga aagcgggcag agcggcagcg   2460
agactcccgg gacctcagag tccgccacac ccgaaagtga caagaagtac agcatcggcc   2520
tggacatcgg caccaactct gtgggctggg ccgtgatcac cgacgagtac aaggtgccca   2580
gcaagaaatt caaggtgctg ggcaacaccg accggcacag catcaagaag aacctgatcg   2640
gagccctgct gttcgacagc ggcgaaacag ccgaggccac ccggctgaag agaaccgcca   2700
gaagaagata caccagacgg aagaaccgga tctgctatct gcaagagatc ttcagcaacg   2760
agatggccaa ggtggacgac agcttcttcc acagactgga agagtccttc ctggtggaag   2820
aggataagaa gcacgagcgg caccccatct tcggcaacat cgtggacgag gtggcctacc   2880
acgagaagta ccccaccatc taccacctga gaaagaaact ggtggacagc accgacaagg   2940
ccgacctgcg gctgatctat ctggccctgg cccacatgat caagttccgg ggccacttcc   3000
tgatcgaggg cgacctgaac cccgacaaca gcgacgtgga caagctgttc atccagctgg   3060
```

```
tgcagaccta caaccagctg ttcgaggaaa accccatcaa cgccagcggc gtggacgcca   3120
aggccatcct gtctgccaga ctgagcaaga gcagacggct ggaaaatctg atcgcccagc   3180
tgcccggcga gaagaagaat ggcctgttcg gaaacctgat tgccctgagc ctgggcctga   3240
cccccaactt caagagcaac ttcgacctgg ccgaggatgc caaactgcag ctgagcaagg   3300
acacctacga cgacgacctg gacaacctgc tggcccagat cggcgaccag tacgccgacc   3360
tgtttctggc cgccaagaac ctgtccgacg ccatcctgct gagcgacatc ctgagagtga   3420
acaccgagat caccaaggcc cccctgagcg cctctatgat caagagatac gacgagcacc   3480
accaggacct gaccctgctg aaagctctcg tgcggcagca gctgcctgag aagtacaaag   3540
agattttctt cgaccagagc aagaacggct acgccggcta cattgacggc ggagccagcc   3600
aggaagagtt ctacaagttc atcaagccca tcctggaaaa gatggacggc accgaggaac   3660
tgctcgtgaa gctgaacaga gaggacctgc tgcggaagca gcggaccttc gacaacggca   3720
gcatccccca ccagatccac ctgggagagc tgcacgccat tctgcggcgg caggaagatt   3780
tttacccatt cctgaaggac aaccgggaaa agatcgagaa gatcctgacc ttccgcatcc   3840
cctactacgt gggccctctg gccaggggaa acagcagatt cgcctggatg accagaaaga   3900
gcgaggaaac catcaccccc tggaacttcg aggaagtggt ggacaagggc gcttccgccc   3960
agagcttcat cgagcggatg accaacttcg ataagaacct gcccaacgag aaggtgctgc   4020
ccaagcacag cctgctgtac gagtacttca ccgtgtataa cgagctgacc aaagtgaaat   4080
acgtgaccga gggaatgaga aagcccgcct tcctgagcgg cgagcagaaa aaggccatcg   4140
tggacctgct gttcaagacc aaccggaaag tgaccgtgaa gcagctgaaa gaggactact   4200
tcaagaaaat cgagtgcttc gactccgtgg aaatctccgg cgtggaagat cggttcaacg   4260
cctccctggg cacataccac gatctgctga aaattatcaa ggacaaggac ttcctggaca   4320
atgaggaaaa cgaggacatt ctggaagata tcgtgctgac cctgacactg tttgaggaca   4380
gagagatgat cgaggaacgg ctgaaaacct atgcccacct gttcgacgac aaagtgatga   4440
agcagctgaa gcggcggaga tacaccggct ggggcaggct gagccggaag ctgatcaacg   4500
gcatccggga caagcagtcc ggcaagacaa tcctggattt cctgaagtcc gacggcttcg   4560
ccaacagaaa cttcatgcag ctgatccacg acgacagcct gacctttaaa gaggacatcc   4620
agaaagccca ggtgtccggc cagggcgata gcctgcacga gcacattgcc aatctggccg   4680
gcagccccgc cattaagaag ggcatcctgc agacagtgaa ggtggtggac gagctcgtga   4740
aagtgatggg ccggcacaag cccgagaaca tcgtgatcga aatggccaga gagaaccaga   4800
ccacccagaa gggacagaag aacagccgcg agagaatgaa gcggatcgaa gagggcatca   4860
aagagctggg cagccagatc ctgaaagaac accccgtgga aaacacccag ctgcagaacg   4920
agaagctgta cctgtactac ctgcagaatg ggcgggatat gtacgtggac caggaactgg   4980
acatcaaccg gctgtccgac tacgatgtgg accatatcgt gcctcagagc tttctgaagg   5040
acgactccat cgacaacaag gtgctgacca gaagcgacaa gaaccggggc aagagcgaca   5100
acgtgccctc cgaagaggtc gtgaagaaga tgaagaacta ctggcggcag ctgctgaacg   5160
ccaagctgat tacccagaga aagttcgaca atctgaccaa ggccgagaga ggcggcctga   5220
gcgaactgga taaggccggc ttcatcaaga gacagctggt ggaaacccgg cagatcacaa   5280
agcacgtggc acagatcctg gactcccgga tgaacactaa gtacgacgag aatgacaagc   5340
tgatccggga agtgaaagtg atcaccctga agtccaagct ggtgtccgat ttccggaagg   5400
atttccagtt ttacaaagtg cgcgagatca acaactacca ccacgcccac gacgcctacc   5460
```

-continued

```
tgaacgccgt cgtgggaacc gccctgatca aaaagtaccc taagctggaa agcgagttcg   5520
tgtacggcga ctacaaggtg tacgacgtgc ggaagatgat cgccaagagc gagcaggaaa   5580
tcggcaaggc taccgccaag tacttcttct acagcaacat catgaacttt ttcaagaccg   5640
agattaccct ggccaacggc gagatccgga agcggcctct gatcgagaca aacggcgaaa   5700
ccggggagat cgtgtgggat aagggccggg attttgccac cgtgcggaaa gtgctgagca   5760
tgccccaagt gaatatcgtg aaaaagaccg aggtgcagac aggcggcttc agcaaagagt   5820
ctatcctgcc caagaggaac agcgataagc tgatcgccag aaagaaggac tgggacccta   5880
agaagtacgg cggcttcgac agccccaccg tggcctattc tgtgctggtg gtggccaaag   5940
tggaaaaggg caagtccaag aaactgaaga gtgtgaaaga gctgctgggg atcaccatca   6000
tggaaagaag cagcttcgag aagaatccca tcgactttct ggaagccaag ggctacaaag   6060
aagtgaaaaa ggacctgatc atcaagctgc ctaagtactc cctgttcgag ctggaaaacg   6120
gccggaagag aatgctggcc tctgccggcg aactgcagaa gggaaacgaa ctggccctgc   6180
cctccaaata tgtgaacttc ctgtacctgg ccagccacta tgagaagctg aagggctccc   6240
ccgaggataa tgagcagaaa cagctgtttg tggaacagca caagcactac ctggacgaga   6300
tcatcgagca gatcagcgag ttctccaaga gagtgatcct ggccgacgct aatctggaca   6360
aagtgctgtc cgcctacaac aagcaccggg ataagcccat cagagagcag gccgagaata   6420
tcatccacct gtttaccctg accaatctgg gagcccctgc cgccttcaag tactttgaca   6480
ccaccatcga ccggaagagg tacaccagca ccaaagaggt gctggacgcc accctgatcc   6540
accagagcat caccggcctg tacgagacac ggatcgacct gtctcagctg ggaggcgaca   6600
aaaggccggc ggccacgaaa aaggccggcc aggcaaaaaa gaaaaaggaa ttcggcagtg   6660
gagagggcag aggaagtctg ctaacatgcg gtgacgtcga ggagaatcct ggcccagtga   6720
gcaagggcga ggagctgttc accggggtgg tgcccatcct ggtcgagctg gacggcgacg   6780
taaacggcca caagttcagc gtgtccggcg agggcgaggg cgatgccacc tacggcaagc   6840
tgaccctgaa gttcatctgc accaccggca agctgcccgt gccctggccc accctcgtga   6900
ccaccctgac ctacggcgtg cagtgcttca gccgctaccc cgaccacatg aagcagcacg   6960
acttcttcaa gtccgccatg cccgaaggct acgtccagga gcgcaccatc ttcttcaagg   7020
acgacggcaa ctacaagacc cgcgccgagg tgaagttcga gggcgacacc ctggtgaacc   7080
gcatcgagct gaagggcatc gacttcaagg aggacggcaa catcctgggg cacaagctgg   7140
agtacaacta caacagccac aacgtctata tcatggccga caagcagaag aacggcatca   7200
aggtgaactt caagatccgc cacaacatcg aggacggcag cgtgcagctc gccgaccact   7260
accagcagaa cacccccatc ggcgacggcc ccgtgctgct gcccgacaac cactacctga   7320
gcacccagtc cgccctgagc aaagacccca acgagaagcg cgatcacatg gtcctgctgg   7380
agttcgtgac cgccgccggg atcactctcg gcatggacga gctgtacaag gaattctaac   7440
tagagctcgc tgatcagcct cgactgtgcc ttctagttgc cagccatctg ttgtttgccc   7500
ctcccccgtg ccttccttga ccctggaagg tgccactccc actgtccttt cctaataaaa   7560
tgaggaaatt gcatcgcatt gtctgagtag gtgtcattct attctggggg gtggggtggg   7620
gcaggacagc aagggggagg attgggaaga gaatagcagg catgctgggg agcggccgca   7680
ggaaccccta gtgatggagt tggccactcc ctctctgcgc gctcgctcgc tcactgaggc   7740
cgggcgacca aaggtcgccc gacgcccggg ctttgcccgg gcggcctcag tgagcgagcg   7800
```

```
agcgcgcagc tgcctgcagg ggcgcctgat gcggtatttt ctccttacgc atctgtgcgg   7860
tatttcacac cgcatacgtc aaagcaacca tagtacgcgc cctgtagcgg cgcattaagc   7920
gcggcgggtg tggtggttac gcgcagcgtg accgctacac ttgccagcgc cctagcgccc   7980
gctcctttcg ctttcttccc ttcctttctc gccacgttcg ccggctttcc ccgtcaagct   8040
ctaaatcggg ggctcccttt agggttccga tttagtgctt tacggcacct cgaccccaaa   8100
aaacttgatt tgggtgatgg ttcacgtagt gggccatcgc cctgatagac ggtttttcgc   8160
cctttgacgt tggagtccac gttctttaat agtggactct tgttccaaac tggaacaaca   8220
ctcaacccta tctcgggcta ttcttttgat ttataaggga ttttgccgat ttcggcctat   8280
tggttaaaaa atgagctgat ttaacaaaaa tttaacgcga attttaacaa aatattaacg   8340
tttacaattt tatggtgcac tctcagtaca atctgctctg atgccgcata gttaagccag   8400
ccccgacacc cgccaacacc cgctgacgcg ccctgacggg cttgtctgct cccggcatcc   8460
gcttacagac aagctgtgac cgtctccggg agctgcatgt gtcagaggtt ttcaccgtca   8520
tcaccgaaac gcgcgagacg aaagggcctc gtgatacgcc tatttttata ggttaatgtc   8580
atgataataa tggtttctta gacgtcaggt ggcacttttc ggggaaatgt gcgcggaacc   8640
cctatttgtt tatttttcta aatacattca aatatgtatc cgctcatgag acaataaccc   8700
tgataaatgc ttcaataata ttgaaaaagg aagagtatga gtattcaaca tttccgtgtc   8760
gcccttattc ccttttttgc ggcattttgc cttcctgttt ttgctcaccc agaaacgctg   8820
gtgaaagtaa aagatgctga agatcagttg ggtgcacgag tgggttacat cgaactggat   8880
ctcaacagcg gtaagatcct tgagagtttt cgccccgaag aacgttttcc aatgatgagc   8940
acttttaaag ttctgctatg tggcgcggta ttatcccgta ttgacgccgg gcaagagcaa   9000
ctcggtcgcc gcatacacta ttctcagaat gacttggttg agtactcacc agtcacagaa   9060
aagcatctta cggatggcat gacagtaaga gaattatgca gtgctgccat aaccatgagt   9120
gataacactg cggccaactt acttctgaca acgatcggag gaccgaagga gctaaccgct   9180
tttttgcaca acatggggga tcatgtaact cgccttgatc gttgggaacc ggagctgaat   9240
gaagccatac caaacgacga gcgtgacacc acgatgcctg tagcaatggc aacaacgttg   9300
cgcaaactat taactggcga actacttact ctagcttccc ggcaacaatt aatagactgg   9360
atggaggcgg ataaagttgc aggaccactt ctgcgctcgg cccttccggc tggctggttt   9420
attgctgata aatctggagc cggtgagcgt ggaagccgcg gtatcattgc agcactgggg   9480
ccagatggta agccctcccg tatcgtagtt atctacacga cggggagtca ggcaactatg   9540
gatgaacgaa atagacagat cgctgagata ggtgcctcac tgattaagca ttggtaactg   9600
tcagaccaag tttactcata tatactttag attgatttaa aacttcattt ttaatttaaa   9660
aggatctagg tgaagatcct ttttgataat ctcatgacca aaatccctta acgtgagttt   9720
tcgttccact gagcgtcaga ccccgtagaa aagatcaaag gatcttcttg agatcctttt   9780
tttctgcgcg taatctgctg cttgcaaaca aaaaaaccac cgctaccagc ggtggtttgt   9840
ttgccggatc aagagctacc aactcttttt ccgaaggtaa ctggcttcag cagagcgcag   9900
ataccaaata ctgtccttct agtgtagccg tagttaggcc accacttcaa gaactctgta   9960
gcaccgccta catacctcgc tctgctaatc ctgttaccag tggctgctgc cagtggcgat  10020
aagtcgtgtc ttaccgggtt ggactcaaga cgatagttac cggataaggc gcagcggtcg  10080
ggctgaacgg ggggttcgtg cacacagccc agcttggagc gaacgaccta caccgaactg  10140
agatacctac agcgtgagct atgagaaagc gccacgcttc ccgaagggag aaaggcggac  10200
```

aggtatccgg taagcggcag ggtcggaaca ggagagcgca cgagggagct tccaggggga 10260
aacgcctggt atctttatag tcctgtcggg tttcgccacc tctgacttga gcgtcgattt 10320
ttgtgatgct cgtcaggggg gcggagccta tggaaaaacg ccagcaacgc ggccttttta 10380
cggttcctgg ccttttgctg gccttttgct cacatgt 10417

<210> SEQ ID NO 64
<211> LENGTH: 9958
<212> TYPE: DNA
<213> ORGANISM: Artificial Sequence
<220> FEATURE:
<223> OTHER INFORMATION: pGT9

<400> SEQUENCE: 64
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg ggtcttcgag aagacctgtt ttagagctag aaatagcaag ttaaaataag 300
gctagtccgt tatcaacttg aaaaagtggc accgagtcgg tgcttttttg ttttagagct 360
agaaatagca agttaaaata aggctagtcc gtttttagcg cgtgcgccaa ttctgcagac 420
aaatggctct agaggtaccc gttacataac ttacggtaaa tggcccgcct ggctgaccgc 480
ccaacgaccc ccgcccattg acgtcaatag taacgccaat agggactttc cattgacgtc 540
aatgggtgga gtatttacgg taaactgccc acttggcagt acatcaagtg tatcatatgc 600
caagtacgcc ccctattgac gtcaatgacg gtaaatggcc cgcctggcat tgtgcccagt 660
acatgacctt atgggacttt cctacttggc agtacatcta cgtattagtc atcgctatta 720
ccatggtcga ggtgagcccc acgttctgct tcactctccc catctccccc ccctccccac 780
ccccaatttt gtatttattt atttttaat tattttgtgc agcgatgggg gcgggggggg 840 gggggggcg cgcgccaggc ggggcggggc ggggcgaggg gcggggcggg gcgaggcgga 900
gaggtgcggc ggcagccaat cagagcggcg cgctccgaaa gtttcctttt atggcgaggc 960
ggcggcggcg gcggccctat aaaaagcgaa gcgcgcggcg ggcgggagtc gctgcgacgc 1020
tgccttcgcc ccgtgccccg ctccgccgcc gcctcgcgcc gcccgccccg gctctgactg 1080
accgcgttac tcccacaggt gagcgggcgg gacggccctt ctcctccggg ctgtaattag 1140
ctgagcaaga ggtaagggtt taagggatgg ttggttggtg gggtattaat gtttaattac 1200
ctggagcacc tgcctgaaat cactttttt caggttggac cggtgccacc atggactata 1260
aggaccacga cggagactac aaggatcatg atattgatta caaagacgat gacgataaga 1320
tggccccaaa gaagaagcgg aaggtcggta tccacggagt cccagcagcc atgtctagac 1380
tggataaaag taaagtgatt aacagcgcac tggagctgct taatgaggtc ggaatcgaag 1440
gtctgacaac cagaaaactc gcccagaagc tgggtgtaga gcagcctaca ttgtattggc 1500
atgtaaaaaa taagcgggct ttgctcgacg ccctggccat tgagatgctg gataggcacc 1560
atactcactt ttgccctctg gaaggggaaa gctggcaaga ttttctgaga aataacgcta 1620
aaagttttag atgtgctctg ctgagtcatc gcgatggagc aaaagtacat ctgggtacac 1680
ggcctacaga aaaacagtat gaaactctcg aaaatcaact ggcctttctg tgccaacaag 1740
gtttttcact ggagaatgca ctgtatgcac tcagcgctgt ggggcatttt actctgggtt 1800

```
gcgtattgga agatcaagag catcaagtcg ctaaagaaga aagggaaaca cctactactg   1860
atagtatgcc gccactgctg cgacaagcta tcgaactgtt tgatcaccaa ggtgcagagc   1920
cagccttcct gttcggcctt gaattgatca tatgcggact ggaaaaacaa cttaaatgtg   1980
aaagtgggtc tagcggcagc gagactcccg ggacctcaga gtccgccaca cccgaaagtg   2040
acaagaagta cagcatcggc ctggacatcg gcaccaactc tgtgggctgg gccgtgatca   2100
ccgacgagta caaggtgccc agcaagaaat tcaaggtgct gggcaacacc gaccggcaca   2160
gcatcaagaa gaacctgatc ggagccctgc tgttcgacag cggcgaaaca gccgaggcca   2220
cccggctgaa gagaaccgcc agaagaagat acaccagacg gaagaaccgg atctgctatc   2280
tgcaagagat cttcagcaac gagatggcca aggtggacga cagcttcttc cacagactgg   2340
aagagtcctt cctggtggaa gaggataaga agcacgagcg gcaccccatc ttcggcaaca   2400
tcgtggacga ggtggcctac cacgagaagt accccaccat ctaccacctg agaaagaaac   2460
tggtggacag caccgacaag gccgacctgc ggctgatcta tctggccctg gcccacatga   2520
tcaagttccg gggccacttc ctgatcgagg gcgacctgaa ccccgacaac agcgacgtgg   2580
acaagctgtt catccagctg gtgcagacct acaaccagct gttcgaggaa aaccccatca   2640
acgccagcgg cgtggacgcc aaggccatcc tgtctgccag actgagcaag agcagacggc   2700
tggaaaatct gatcgcccag ctgcccggcg agaagaagaa tggcctgttc ggaaacctga   2760
ttgccctgag cctgggcctg acccccaact tcaagagcaa cttcgacctg gccgaggatg   2820
ccaaactgca gctgagcaag gacacctacg acgacgacct ggacaacctg ctggcccaga   2880
tcggcgacca gtacgccgac ctgtttctgg ccgccaagaa cctgtccgac gccatcctgc   2940
tgagcgacat cctgagagtg aacaccgaga tcaccaaggc ccccctgagc gcctctatga   3000
tcaagagata cgacgagcac caccaggacc tgaccctgct gaaagctctc gtgcggcagc   3060
agctgcctga gaagtacaaa gagattttct tcgaccagag caagaacggc tacgccggct   3120
acattgacgg cggagccagc caggaagagt tctacaagtt catcaagccc atcctggaaa   3180
agatggacgg caccgaggaa ctgctcgtga agctgaacag agaggacctg ctgcggaagc   3240
agcggacctt cgacaacggc agcatccccc accagatcca cctgggagag ctgcacgcca   3300
ttctgcggcg gcaggaagat ttttacccat tcctgaagga caaccgggaa aagatcgaga   3360
agatcctgac cttccgcatc ccctactacg tgggccctct ggccagggga aacagcagat   3420
tcgcctggat gaccagaaag agcgaggaaa ccatcacccc ctggaacttc gaggaagtgg   3480
tggacaaggg cgcttccgcc cagagcttca tcgagcggat gaccaacttc gataagaacc   3540
tgcccaacga gaaggtgctg cccaagcaca gcctgctgta cgagtacttc accgtgtata   3600
acgagctgac caaagtgaaa tacgtgaccg agggaatgag aaagcccgcc ttcctgagcg   3660
gcgagcagaa aaaggccatc gtggacctgc tgttcaagac caaccggaaa gtgaccgtga   3720
agcagctgaa agaggactac ttcaagaaaa tcgagtgctt cgactccgtg gaaatctccg   3780
gcgtggaaga tcggttcaac gcctccctgg gcacatacca cgatctgctg aaaattatca   3840
aggacaagga cttcctggac aatgaggaaa acgaggacat tctggaagat atcgtgctga   3900
ccctgacact gtttgaggac agagagatga tcgaggaacg gctgaaaacc tatgcccacc   3960
tgttcgacga caaagtgatg aagcagctga agcggcggag atacaccggc tggggcaggc   4020
tgagccggaa gctgatcaac ggcatccggg acaagcagtc cggcaagaca atcctggatt   4080
tcctgaagtc cgacggcttc gccaacagaa acttcatgca gctgatccac gacgacagcc   4140
tgacctttaa agaggacatc cagaaagccc aggtgtccgg ccagggcgat agcctgcacg   4200
```

```
agcacattgc caatctggcc ggcagccccg ccattaagaa gggcatcctg cagacagtga   4260
aggtggtgga cgagctcgtg aaagtgatgg gccggcacaa gcccgagaac atcgtgatcg   4320
aaatggccag agagaaccag accacccaga agggacagaa gaacagccgc gagagaatga   4380
agcggatcga agagggcatc aaagagctgg gcagccagat cctgaaagaa caccccgtgg   4440
aaaacaccca gctgcagaac gagaagctgt acctgtacta cctgcagaat gggcgggata   4500
tgtacgtgga ccaggaactg gacatcaacc ggctgtccga ctacgatgtg gaccatatcg   4560
tgcctcagag ctttctgaag gacgactcca tcgacaacaa ggtgctgacc agaagcgaca   4620
agaaccgggg caagagcgac aacgtgccct ccgaagaggt cgtgaagaag atgaagaact   4680
actggcggca gctgctgaac gccaagctga ttacccagag aaagttcgac aatctgacca   4740
aggccgagag aggcggcctg agcgaactgg ataaggccgg cttcatcaag agacagctgg   4800
tggaaacccg gcagatcaca aagcacgtgg cacagatcct ggactcccgg atgaacacta   4860
agtacgacga gaatgacaag ctgatccggg aagtgaaagt gatcaccctg aagtccaagc   4920
tggtgtccga tttccggaag gatttccagt tttacaaagt gcgcgagatc aacaactacc   4980
accacgccca cgacgcctac ctgaacgccg tcgtgggaac cgccctgatc aaaaagtacc   5040
ctaagctgga aagcgagttc gtgtacggcg actacaaggt gtacgacgtg cggaagatga   5100
tcgccaagag cgagcaggaa atcggcaagg ctaccgccaa gtacttcttc tacagcaaca   5160
tcatgaactt tttcaagacc gagattaccc tggccaacgg cgagatccgg aagcggcctc   5220
tgatcgagac aaacggcgaa accggggaga tcgtgtggga taagggccgg gattttgcca   5280
ccgtgcggaa agtgctgagc atgccccaag tgaatatcgt gaaaaagacc gaggtgcaga   5340
caggcggctt cagcaaagag tctatcctgc ccaagaggaa cagcgataag ctgatcgcca   5400
gaaagaagga ctgggaccct aagaagtacg gcggcttcga cagccccacc gtggcctatt   5460
ctgtgctggt ggtggccaaa gtggaaaagg gcaagtccaa gaaactgaag agtgtgaaag   5520
agctgctggg gatcaccatc atggaaagaa gcagcttcga gaagaatccc atcgactttc   5580
tggaagccaa gggctacaaa gaagtgaaaa aggacctgat catcaagctg cctaagtact   5640
ccctgttcga gctggaaaac ggccggaaga gaatgctggc ctctgccggc gaactgcaga   5700
agggaaacga actggccctg ccctccaaat atgtgaactt cctgtacctg gccagccact   5760
atgagaagct gaagggctcc cccgaggata atgagcagaa acagctgttt gtggaacagc   5820
acaagcacta cctggacgag atcatcgagc agatcagcga gttctccaag agagtgatcc   5880
tggccgacgc taatctggac aaagtgctgt ccgcctacaa caagcaccgg gataagccca   5940
tcagagagca ggccgagaat atcatccacc tgtttaccct gaccaatctg ggagcccctg   6000
ccgccttcaa gtactttgac accaccatcg accggaagag gtacaccagc accaaagagg   6060
tgctggacgc caccctgatc caccagagca tcaccggcct gtacgagaca cggatcgacc   6120
tgtctcagct gggaggcgac aaaaggccgg cggccacgaa aaaggccggc caggcaaaaa   6180
agaaaaagga attcggcagt ggagagggca gaggaagtct gctaacatgc ggtgacgtcg   6240
aggagaatcc tggcccagtg agcaagggcg aggagctgtt caccggggtg gtgcccatcc   6300
tggtcgagct ggacggcgac gtaaacggcc acaagttcag cgtgtccggc gagggcgagg   6360
gcgatgccac ctacggcaag ctgaccctga agttcatctg caccaccggc aagctgcccg   6420
tgccctggcc caccctcgtg accaccctga cctacggcgt gcagtgcttc agccgctacc   6480
ccgaccacat gaagcagcac gacttcttca agtccgccat gcccgaaggc tacgtccagg   6540
```

```
agcgcaccat cttcttcaag gacgacggca actacaagac ccgcgccgag gtgaagttcg   6600
agggcgacac cctggtgaac cgcatcgagc tgaagggcat cgacttcaag gaggacggca   6660
acatcctggg gcacaagctg gagtacaact acaacagcca caacgtctat atcatggccg   6720
acaagcagaa gaacggcatc aaggtgaact tcaagatccg ccacaacatc gaggacggca   6780
gcgtgcagct cgccgaccac taccagcaga acacccccat cggcgacggc cccgtgctgc   6840
tgcccgacaa ccactacctg agcacccagt ccgccctgag caaagacccc aacgagaagc   6900
gcgatcacat ggtcctgctg gagttcgtga ccgccgccgg gatcactctc ggcatggacg   6960
agctgtacaa ggaattctaa ctagagctcg ctgatcagcc tcgactgtgc cttctagttg   7020
ccagccatct gttgtttgcc cctcccccgt gccttccttg accctggaag gtgccactcc   7080
cactgtcctt tcctaataaa atgaggaaat tgcatcgcat tgtctgagta ggtgtcattc   7140
tattctgggg ggtggggtgg ggcaggacag caagggggag gattgggaag agaatagcag   7200
gcatgctggg gagcggccgc aggaacccct agtgatggag ttggccactc cctctctgcg   7260
cgctcgctcg ctcactgagg ccgggcgacc aaaggtcgcc cgacgcccgg gctttgcccg   7320
ggcggcctca gtgagcgagc gagcgcgcag ctgcctgcag gggcgcctga tgcggtattt   7380
tctccttacg catctgtgcg gtatttcaca ccgcatacgt caaagcaacc atagtacgcg   7440
ccctgtagcg gcgcattaag cgcggcgggt gtggtggtta cgcgcagcgt gaccgctaca   7500
cttgccagcg ccctagcgcc cgctcctttc gctttcttcc cttcctttct cgccacgttc   7560
gccggctttc cccgtcaagc tctaaatcgg gggctccctt tagggttccg atttagtgct   7620
ttacggcacc tcgaccccaa aaaacttgat ttgggtgatg gttcacgtag tgggccatcg   7680
ccctgataga cggtttttcg ccctttgacg ttggagtcca cgttctttaa tagtggactc   7740
ttgttccaaa ctggaacaac actcaaccct atctcgggct attcttttga tttataaggg   7800
attttgccga tttcggccta ttggttaaaa aatgagctga tttaacaaaa atttaacgcg   7860
aattttaaca aaatattaac gtttacaatt ttatggtgca ctctcagtac aatctgctct   7920
gatgccgcat agttaagcca gccccgacac ccgccaacac ccgctgacgc gccctgacgg   7980
gcttgtctgc tcccggcatc cgcttacaga caagctgtga ccgtctccgg gagctgcatg   8040
tgtcagaggt tttcaccgtc atcaccgaaa cgcgcgagac gaaagggcct cgtgatacgc   8100
ctatttttat aggttaatgt catgataata atggtttctt agacgtcagg tggcactttt   8160
cggggaaatg tgcgcggaac ccctatttgt ttatttttct aaatacattc aaatatgtat   8220
ccgctcatga gacaataacc ctgataaatg cttcaataat attgaaaaag gaagagtatg   8280
agtattcaac atttccgtgt cgcccttatt cccttttttg cggcattttg ccttcctgtt   8340
tttgctcacc cagaaacgct ggtgaaagta aaagatgctg aagatcagtt gggtgcacga   8400
gtgggttaca tcgaactgga tctcaacagc ggtaagatcc ttgagagttt tcgccccgaa   8460
gaacgttttc caatgatgag cacttttaaa gttctgctat gtggcgcggt attatcccgt   8520
attgacgccg ggcaagagca actcggtcgc cgcatacact attctcagaa tgacttggtt   8580
gagtactcac cagtcacaga aaagcatctt acggatggca tgacagtaag agaattatgc   8640
agtgctgcca taaccatgag tgataacact gcggccaact tacttctgac aacgatcgga   8700
ggaccgaagg agctaaccgc ttttttgcac aacatggggg atcatgtaac tcgccttgat   8760
cgttgggaac cggagctgaa tgaagccata ccaaacgacg agcgtgacac cacgatgcct   8820
gtagcaatgg caacaacgtt gcgcaaacta ttaactggcg aactacttac tctagcttcc   8880
cggcaacaat taatagactg gatggaggcg gataaagttg caggaccact tctgcgctcg   8940
```

```
gcccttccgg ctggctggtt tattgctgat aaatctggag ccggtgagcg tggaagccgc   9000

ggtatcattg cagcactggg gccagatggt aagccctccc gtatcgtagt tatctacacg   9060

acggggagtc aggcaactat ggatgaacga aatagacaga tcgctgagat aggtgcctca   9120

ctgattaagc attggtaact gtcagaccaa gtttactcat atatacttta gattgattta   9180

aaacttcatt tttaatttaa aaggatctag gtgaagatcc tttttgataa tctcatgacc   9240

aaaatccctt aacgtgagtt ttcgttccac tgagcgtcag accccgtaga aaagatcaaa   9300

ggatcttctt gagatccttt ttttctgcgc gtaatctgct gcttgcaaac aaaaaaacca   9360

ccgctaccag cggtggtttg tttgccggat caagagctac caactctttt tccgaaggta   9420

actggcttca gcagagcgca gataccaaat actgtccttc tagtgtagcc gtagttaggc   9480

caccacttca agaactctgt agcaccgcct acatacctcg ctctgctaat cctgttacca   9540

gtggctgctg ccagtggcga taagtcgtgt cttaccgggt tggactcaag acgatagtta   9600

ccggataagg cgcagcggtc gggctgaacg gggggttcgt gcacacagcc cagcttggag   9660

cgaacgacct acaccgaact gagataccta cagcgtgagc tatgagaaag cgccacgctt   9720

cccgaaggga gaaaggcgga caggtatccg gtaagcggca gggtcggaac aggagagcgc   9780

acgagggagc ttccaggggg aaacgcctgg tatctttata gtcctgtcgg gtttcgccac   9840

ctctgacttg agcgtcgatt tttgtgatgc tcgtcagggg ggcggagcct atggaaaaac   9900

gccagcaacg cggccttttt acggttcctg gccttttgct ggccttttgc tcacatgt     9958
```

```
<210> SEQ ID NO 65
<211> LENGTH: 3465
<212> TYPE: DNA
<213> ORGANISM: Artificial Sequence
<220> FEATURE:
<223> OTHER INFORMATION: ptet repressor

<400> SEQUENCE: 65
```

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt accactttcg    420

ggtgtggcgg actctgaggt cccgggagtc tcgctgccgc tagacccact ttcacattta    480

agttgttttt ccagtccgca tatgatcaat tcaaggccga acaggaaggc tggctctgca    540

ccttggtgat caaacagttc gatagcttgt cgcagcagtg gcggcatact atcagtagta    600

ggtgtttccc tttcttcttt agcgacttga tgctcttgat cttccaatac gcaacccaga    660

gtaaaatgcc ccacagcgct gagtgcatac agtgcattct ccagtgaaaa accttgttgg    720

cacagaaagg ccagttgatt ttcgagagtt tcatactgtt tttctgtagg ccgtgtaccc    780

agatgtactt ttgctccatc gcgatgactc agcagagcac atctaaaact tttagcgtta    840

tttctcagaa aatcttgcca gctttcccct tccagagggc aaaagtgagt atggtgccta    900

tccagcatct caatggccag ggcgtcgagc aaagcccgct tattttttac atgccaatac    960

aatgtaggct gctctacacc cagcttctgg gcgagttttc tggttgtcag accttcgatt   1020
```

-continued

```
ccgacctcat taagcagctc cagtgcgctg ttaatcactt tacttttatc cagtctagac   1080
atggctgctg ggactccgtg gataccgacc ttccgcttct tctttggggc catcttatcg   1140
tcatcgtctt tgtaatcaat atcatgatcc ttgtagtctc cgtcgtggtc cttatagtcc   1200
atgtcgactg cagaggcctg catgcaagct tggcgtaatc atggtcatag ctgtttcctg   1260
tgtgaaattg ttatccgctc acaattccac acaacatacg agccggaagc ataaagtgta   1320
aagcctgggg tgcctaatga gtgagctaac tcacattaat tgcgttgcgc tcactgcccg   1380
ctttccagtc gggaaacctg tcgtgccagc tgcattaatg aatcggccaa cgcgcgggga   1440
gaggcggttt gcgtattggg cgctcttccg cttcctcgct cactgactcg ctgcgctcgg   1500
tcgttcggct gcggcgagcg gtatcagctc actcaaaggc ggtaatacgg ttatccacag   1560
aatcagggga taacgcagga aagaacatgt gagcaaaagg ccagcaaaag gccaggaacc   1620
gtaaaaaggc cgcgttgctg gcgtttttcc ataggctccg cccccctgac gagcatcaca   1680
aaaatcgacg ctcaagtcag aggtggcgaa acccgacagg actataaaga taccaggcgt   1740
ttccccctgg aagctccctc gtgcgctctc ctgttccgac cctgccgctt accggatacc   1800
tgtccgcctt tctcccttcg ggaagcgtgg cgctttctca tagctcacgc tgtaggtatc   1860
tcagttcggt gtaggtcgtt cgctccaagc tgggctgtgt gcacgaaccc cccgttcagc   1920
ccgaccgctg cgccttatcc ggtaactatc gtcttgagtc caacccggta agacacgact   1980
tatcgccact ggcagcagcc actggtaaca ggattagcag agcgaggtat gtaggcggtg   2040
ctacagagtt cttgaagtgg tggcctaact acggctacac tagaagaaca gtatttggta   2100
tctgcgctct gctgaagcca gttaccttcg gaaaaagagt tggtagctct tgatccggca   2160
aacaaaccac cgctggtagc ggtggttttt ttgtttgcaa gcagcagatt acgcgcagaa   2220
aaaaaggatc tcaagaagat cctttgatct tttctacggg gtctgacgct cagtggaacg   2280
aaaactcacg ttaagggatt ttggtcatga gattatcaaa aaggatcttc acctagatcc   2340
ttttaaatta aaaatgaagt tttaaatcaa tctaaagtat atatgagtaa acttggtctg   2400
acagttacca atgcttaatc agtgaggcac ctatctcagc gatctgtcta tttcgttcat   2460
ccatagttgc ctgactcccc gtcgtgtaga taactacgat acgggagggc ttaccatctg   2520
gccccagtgc tgcaatgata ccgcgagacc cacgctcacc ggctccagat ttatcagcaa   2580
taaaccagcc agccggaagg gccgagcgca gaagtggtcc tgcaacttta tccgcctcca   2640
tccagtctat taattgttgc cgggaagcta gagtaagtag ttcgccagtt aatagtttgc   2700
gcaacgttgt tgccattgct acaggcatcg tggtgtcacg ctcgtcgttt ggtatggctt   2760
cattcagctc cggttcccaa cgatcaaggc gagttacatg atcccccatg ttgtgcaaaa   2820
aagcggttag ctccttcggt cctccgatcg ttgtcagaag taagttggcc gcagtgttat   2880
cactcatggt tatggcagca ctgcataatt ctcttactgt catgccatcc gtaagatgct   2940
tttctgtgac tggtgagtac tcaaccaagt cattctgaga atagtgtatg cggcgaccga   3000
gttgctcttg cccggcgtca atacgggata ataccgcgcc acatagcaga actttaaaag   3060
tgctcatcat tggaaaacgt tcttcggggc gaaaactctc aaggatctta ccgctgttga   3120
gatccagttc gatgtaaccc actcgtgcac ccaactgatc ttcagcatct tttactttca   3180
ccagcgtttc tgggtgagca aaaacaggaa ggcaaaatgc cgcaaaaaag ggaataaggg   3240
cgacacggaa atgttgaata ctcatactct tcctttttca atattattga agcatttatc   3300
agggttattg tctcatgagc ggatacatat ttgaatgtat ttagaaaaat aaacaaatag   3360
gggttccgcg cacatttccc cgaaaagtgc cacctgacgt ctaagaaacc attattatca   3420
```

tgacattaac ctataaaaat aggcgtatca cgaggccctt tcgtc 3465

<210> SEQ ID NO 66
<211> LENGTH: 29
<212> TYPE: DNA
<213> ORGANISM: Artificial Sequence
<220> FEATURE:
<223> OTHER INFORMATION: Lac operator

<400> SEQUENCE: 66
gtggaattgt gagcggataa caatttcac 29

<210> SEQ ID NO 67
<211> LENGTH: 19
<212> TYPE: DNA
<213> ORGANISM: Artificial Sequence
<220> FEATURE:
<223> OTHER INFORMATION: TET operator

<400> SEQUENCE: 67
tccctatcag tgatagaga 19

<210> SEQ ID NO 68
<211> LENGTH: 33
<212> TYPE: DNA
<213> ORGANISM: Artificial Sequence
<220> FEATURE:
<223> OTHER INFORMATION: TRP operator

<400> SEQUENCE: 68
aaactatcgt actagttaac tagtacgata gtt 33

<210> SEQ ID NO 69
<211> LENGTH: 3792
<212> TYPE: DNA
<213> ORGANISM: Homo sapiens

<400> SEQUENCE: 69
atgaataacg gaactaataa cttccaaaac ttcatcggga tcagttcctt gcagaaaact 60
ctccggaatg ctctcatccc aactgagact actcagcagt tcattgttaa gaatggaatc 120
ataaaagagg acgagcttag gggggaaaat aggcaaatcc tcaaggatat catggatgac 180
tattataggg gctttatatc cgagacactg agcagcattg atgatataga ctggacctct 240
cttttcgaaa agatggaaat acaacttaaa aatggagata acaaggacac cctgataaag 300
gaacagaccg aatataggaa ggcaattcat aaaaagtttg ctaacgatga taggtttaaa 360
aacatgttct cagcaaaact catttcagat atactgcccg aattcgttat ccacaacaac 420
aactactccg ctagcgaaaa agaggaaaag acccaagtca taaagctgtt ctctcgattc 480
gcgacgagtt ttaaagatta tttcaagaat cgcgcaaact gtttctcagc tgatgatatc 540
agcagctcat cctgtcatcg gatcgttaac gataatgctg aaatcttctt ctccaatgca 600
cttgtttata ggcgcattgt taaatctctc tcaaacgatg atatcaataa gatttccggc 660
gatatgaagg acagtcttaa ggagatgagc ctcgaagaga tatactcata cgagaaatat 720
ggcgaattta tcacccagga agggatttcc ttctataatg acatttgcgg caaagtcaat 780
tccttcatga acctgtattg ccaaaaaaat aaagaaaaca agaacctcta taagctgcaa 840
aagttgcata agcaaatact ttgtatcgcg gatacaagct atgaagttcc ctacaagttc 900
gagagtgatg aggaggtgta tcaatctgtc aatggtttcc ttgataatat ttcttctaag 960

```
catattgttg aacgactccg aaagatagga gacaactata atggatacaa tttggataaa   1020
atctacatcg tgtctaaatt ttacgagagt gtgtcacaaa aaacatatag agactgggag   1080
acaattaata ccgccctgga gatacattac aacaatatac ttcccgggaa cgggaagtct   1140
aaggcagaca aggtgaagaa agccgtgaag aacgacttgc aaaagtcaat taccgaaatc   1200
aatgagcttg tttcaaacta taaactttgt tcagatgaca atattaaagc cgaaacctat   1260
attcatgaaa tctctcatat tctgaataac tttgaggcgc aagaactgaa atataaccca   1320
gaaatacacc tcgttgagtc cgaactgaaa gcaagcgaac tgaaaaatgt tttggacgtg   1380
ataatgaacg cttttcattg gtgctcagtc tttatgacag aggagcttgt tgacaaggat   1440
aacaatttct atgcggaact ggaagagatt tacgacgaaa tctatccggt catatccctg   1500
tataacctgg ttcgcaacta tgtcacgcaa aaaccataca gcacgaagaa gattaaactg   1560
aactttggta ttccgacgct ggccgatgga tggtcaaaat ctaaggaata ctcaaacaat   1620
gccataatcc tgatgcgaga taacctctac taccttggaa tctttaatgc taaaaataaa   1680
cccgataaaa aaattatcga agggaacacg agtgaaaaca aaggtgatta taaaaaaatg   1740
atatataatc tgcttccagg accaaataag atgataccca aagttttcct ttcttcaaag   1800
accggcgtcg agacatataa accatccgcg tacatacttg aaggctacaa acaaaataaa   1860
catatcaaat catctaagga ttttgacatt acgttctgtc atgatttgat tgactatttc   1920
aaaaattgca tagccattca tccagagtgg aaaaactttg ggtttgactt ctctgatacc   1980
agtacatatg aagacataag tggattttac cgagaagtag agctccaagg ttataaaata   2040
gactggacct atatatctga aaaggatata gaccttttgc aagagaaggg acagctttat   2100
cttttccaaa tctacaacaa agacttcagt aagaaaagta ccgggaatga caatcttcat   2160
accatgtatc tgaagaacct gttctccgaa gaaaatctga aggacatagt cctgaagctt   2220
aatggcgaag cggaaatttt tttccgaaag agctctatta agaaccccat aatacataag   2280
aagggaagca ttctcgttaa tcgaacgtat gaggccgaag agaaagatca atttgggaat   2340
atccaaatcg ttcgaaagaa cataccagaa aatatttacc aagaattgta caaatatttt   2400
aacgataaaa gcgacaaaga actgtctgat gaagctgcta agctgaaaaa cgtcgtcggc   2460
catcatgagg ccgcgacgaa tatagtcaag gattaccgat atacatacga taagtatttc   2520
ctgcatatgc ccatcactat caactttaag gcaaataaga ctggattcat taatgacaga   2580
atactgcaat acatagctaa agaaaaagat ttgcatgtta ttggcattga caggggtgag   2640
cgcaatctta tctatgtaag cgtcattgat acttgcggga atatcgtaga gcagaagtca   2700
tttaatattg taaatgggta cgattaccaa atcaagttga agcagcaaga gggagcacga   2760
cagattgccc gcaaggagtg gaaagagatc ggaaagataa aggagatcaa ggaggggtat   2820
ttgtcccttg ttatacacga aatttccaag atggtaatca agtacaacgc tataattgct   2880
atggaggatc tctcctatgg atttaaaaag ggaagattta aagtcgagcg gcaggtatat   2940
cagaaatttg aaacaatgct tattaataaa cttaattatc tcgttttcaa agacattagt   3000
atcaccgaaa acggtgggct gttgaagggc tatcaactta cgtacatacc agataagctt   3060
aagaatgtgg gtcaccaatg cggatgcata ttctacgtgc ccgcagctta tacaagcaaa   3120
atcgacccaa caacgggttt cgtaaacata tttaagttca aggatctcac cgtggatgcc   3180
aagcgagagt tcataaaaaa atttgactca atcagatatg actcagaaaa gaatcttttt   3240
tgttttacct tcgactacaa taatttcatt acacaaaata cggttatgag caagtcatcc   3300
tggtccgtat atacgtatgg agtgcgcata aagcggagat tcgttaacgg gcgattttct   3360
```

```
aatgagtccg atacaatcga tataacaaag gatatggaaa aaactctgga aatgactgat   3420
ataaattgga gggacggtca tgacctcagg caagacatta tcgattatga gatcgtgcaa   3480
catatttttg agatctttcg gttgactgtc caaatgagga actctctgtc tgaattggaa   3540
gatagggact acgatcgcct gataagcccc gtgttgaacg agaataacat attctacgat   3600
tccgcgaaag ccggggatgc gctccctaag gacgccgatg caaatggggc ctattgtatt   3660
gctttgaaag ggctgtacga aatcaaacag atcaccgaaa actggaaaga agacgggaag   3720
tttagtcggg ataaactgaa gatatccaac aaggactggt ttgactttat ccaaaataag   3780
cgatatttgt aa                                                        3792
```

<210> SEQ ID NO 70
<211> LENGTH: 3792
<212> TYPE: DNA
<213> ORGANISM: E. coli

<400> SEQUENCE: 70

```
atgaacaacg gcacaaataa ttttcagaac ttcatcggga tctcaagttt gcagaaaacg     60
ctgcgcaatg ctctgatccc cacggaaacc acgcaacagt tcatcgtcaa gaacggaata    120
attaaagaag atgagttacg tggcgagaac cgccagattc tgaaagatat catggatgac    180
tactaccgcg gattcatctc tgagactctg agttctattg atgacataga ttggactagc    240
ctgttcgaaa aaatggaaat tcagctgaaa aatggtgata ataaagatac cttaattaag    300
gaacagacag agtatcggaa agcaatccat aaaaaatttg cgaacgacga tcggtttaag    360
aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaatcgctg agcaatgacg atatcaacaa aatttcgggc    660
gatatgaaag attcattaaa agaaatgagt ctggaagaaa tatattctta cgagaagtat    720
ggggaattta ttacccagga aggcattagc ttctataatg atatctgtgg gaaagtgaat    780
tcttttatga acctgtattg tcagaaaaat aaagaaaaca aaaatttata caaacttcag    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa   1020
atttatatcg tgtccaaatt ttacgagagc gttagccaaa aaacctaccg cgactgggaa   1080
acaattaata ccgccctcga aattcattac aataaatatct tgccgggtaa cggtaaaagt   1140
aaagccgaca aagtaaaaaa agcggttaag aatgatttac agaaatccat caccgaaata   1200
aatgaactag tgtcaaacta taagctgtgc agtgacgaca acatcaaagc ggagacttat   1260
atacatgaga ttagccatat cttgaataac tttgaagcac aggaattgaa atacaatccg   1320
gaaattcacc tagttgaatc cgagctcaaa gcgagtgagc ttaaaaacgt gctggacgtg   1380
atcatgaatg cgtttcattg gtgttcggtt tttatgactg aggaacttgt tgataaagac   1440
aacaattttt atgcggaact ggaggagatt tacgatgaaa tttatccagt aattagtctg   1500
tacaacctgg ttcgtaacta cgttacccag aaaccgtaca gcacgaaaaa gattaaattg   1560
aactttggaa taccgacgtt agcagacggt tggtcaaagt ccaaagagta ttctaataac   1620
```

```
gctatcatac tgatgcgcga caatctgtat tatctgggca tctttaatgc gaagaataaa   1680
ccggacaaga agattatcga gggtaatacg tcagaaaata agggtgacta caaaaagatg   1740
atttataatt tgctcccggg tcccaacaaa atgatcccga aagttttctt gagcagcaag   1800
acgggggtgg aaacgtataa accgagcgcc tatatcctag aggggtataa acagaataaa   1860
catatcaagt cttcaaaaga ctttgatatc actttctgtc atgatctgat cgactacttc   1920
aaaaactgta ttgcaattca tcccgagtgg aaaaacttcg gttttgattt tagcgacacc   1980
agtacttatg aagacatttc cgggttttat cgtgaggtag agttacaagg ttacaagatt   2040
gattggacat acattagcga aaaagacatt gatctgctgc aggaaaaagg tcaactgtat   2100
ctgttccaga tatataacaa agatttttcg aaaaaatcaa ccgggaatga caaccttcac   2160
accatgtacc tgaaaaatct ttctcagaa  gaaaatctta aggatatcgt cctgaaactt   2220
aacggcgaag cggaaatctt cttcaggaag agcagcataa agaacccaat cattcataaa   2280
aaaggctcga ttttagtcaa ccgtacctac gaagcagaag aaaaagacca gtttggcaac   2340
attcaaattg tgcgtaaaaa tattccggaa aacatttatc aggagctgta caaatacttc   2400
aacgataaaa gcgacaaaga gctgtctgat gaagcagcca aactgaagaa tgtagtggga   2460
caccacgagg cagcgacgaa tatagtcaag gactatcgct acacgtatga taaatacttc   2520
cttcatatgc ctattacgat caatttcaaa gccaataaaa cgggttttat taatgatagg   2580
atcttacagt atatcgctaa agaaaaagac ttacatgtga tcggcattga tcggggcgag   2640
cgtaacctga tctacgtgtc cgtgattgat acttgtggta atatagttga acagaaaagc   2700
tttaacattg taaacggcta cgactatcag ataaaactga aacaacagga gggcgctaga   2760
cagattgcgc ggaaagaatg gaaagaaatt ggtaaaatta aagagatcaa agagggctac   2820
ctgagcttag taatccacga gatctctaaa atggtaatca aatacaatgc aattatagcg   2880
atggaggatt tgtcttatgg ttttaaaaaa gggcgcttta aggtcgaacg gcaagtttac   2940
cagaaatttg aaaccatgct catcaataaa ctcaactatc tggtatttaa agatatttcg   3000
attaccgaga atggcggtct cctgaaaggt tatcagctga catacattcc tgataaactt   3060
aaaaacgtgg gtcatcagtg cggctgcatt ttttatgtgc ctgctgcata cacgagcaaa   3120
attgatccga ccaccggctt tgtgaatatc tttaaattta aagacctgac agtggacgca   3180
aaacgtgaat tcattaaaaa atttgactca attcgttatg acagtgaaaa aaatctgttc   3240
tgctttacat ttgactacaa taactttatt acgcaaaaca cggtcatgag caaatcatcg   3300
tggagtgtgt atacatacgg cgtgcgcatc aaacgtcgct ttgtgaacgg ccgcttctca   3360
aacgaaagtg ataccattga cataaccaaa gatatggaga aaacgttgga aatgacggac   3420
attaactggc gcgatggcca cgatcttcgt caagacatta tagattatga aattgttcag   3480
cacatattcg aaattttccg tttaacagtg caaatgcgta actccttgtc tgaactggag   3540
gaccgtgatt acgatcgtct catttcacct gtactgaacg aaaataacat tttttatgac   3600
agcgcgaaag cgggggatgc acttcctaag gatgccgatg caaatggtgc gtattgtatt   3660
gcattaaaag ggttatatga aattaaacaa attaccgaaa attggaaaga agatggtaaa   3720
ttttcgcgcg ataaactcaa aatcagcaat aaagattggt tcgactttat ccagaataag   3780
cgctatctct aa                                                       3792
```

<210> SEQ ID NO 71
<211> LENGTH: 5
<212> TYPE: PRT
<213> ORGANISM: Artificial Sequence
<220> FEATURE:
<223> OTHER INFORMATION: Linker

<400> SEQUENCE: 71

Gly Gly Gly Gly Ser
1 5

<210> SEQ ID NO 72
<211> LENGTH: 5
<212> TYPE: PRT
<213> ORGANISM: Artificial Sequence
<220> FEATURE:
<223> OTHER INFORMATION: Linker

<400> SEQUENCE: 72

Glu Ala Ala Ala Lys
1 5

<210> SEQ ID NO 73
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: Misc
<222> LOCATION: (2)..(6)
<223> OTHER INFORMATION: EAAAK may be repeated 1, 2, 3, 4, 5, 6, 7, 8, 9, 10, 11, 12, 13, 14, 15, 16, 17, 18, 19 or 20 times.

<400> SEQUENCE: 73

Ala Glu Ala Ala Ala Lys
1 5

<210> SEQ ID NO 74
<211> LENGTH: 18
<212> TYPE: PRT
<213> ORGANISM: Artificial Sequence
<220> FEATURE:
<223> OTHER INFORMATION: Linker

<400> SEQUENCE: 74

Lys Glu Ser Gly Ser Val Ser Ser Glu Gln Leu Ala Gln Phe Arg Ser
1 5 10 15

Leu Asp

<210> SEQ ID NO 75
<211> LENGTH: 14
<212> TYPE: PRT
<213> ORGANISM: Artificial Sequence
<220> FEATURE:
<223> OTHER INFORMATION: Linker

<400> SEQUENCE: 75

Glu Gly Lys Ser Ser Gly Ser Gly Ser Glu Ser Lys Ser Thr
1 5 10

<210> SEQ ID NO 76
<211> LENGTH: 12
<212> TYPE: PRT
<213> ORGANISM: Artificial Sequence
<220> FEATURE:
<223> OTHER INFORMATION: Linker

<400> SEQUENCE: 76

Gly Ser Ala Gly Ser Ala Ala Gly Ser Gly Glu Phe
1 5 10

```
<210> SEQ ID NO 77
<211> LENGTH: 18
<212> TYPE: PRT
<213> ORGANISM: Artificial Sequence
<220> FEATURE:
<223> OTHER INFORMATION: Linker

<400> SEQUENCE: 77

Lys Glu Ser Gly Ser Val Ser Ser Glu Gln Leu Ala Gln Phe Arg Ser
1               5                   10                  15

Leu Glu


<210> SEQ ID NO 78
<211> LENGTH: 36
<212> TYPE: PRT
<213> ORGANISM: Artificial Sequence
<220> FEATURE:
<223> OTHER INFORMATION: Linker

<400> SEQUENCE: 78

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35


<210> SEQ ID NO 79
<211> LENGTH: 17
<212> TYPE: DNA
<213> ORGANISM: Artificial Sequence
<220> FEATURE:
<223> OTHER INFORMATION: GAL-4 binding site
<220> FEATURE:
<221> NAME/KEY: N
<222> LOCATION: (4)..(14)
<223> OTHER INFORMATION: N may be any nucleotide
<220> FEATURE:
<221> NAME/KEY: misc_feature
<222> LOCATION: (4)..(14)
<223> OTHER INFORMATION: n is a, c, g, or t

<400> SEQUENCE: 79

cggnnnnnnn nnnnccg                                                      17


<210> SEQ ID NO 80
<211> LENGTH: 13
<212> TYPE: DNA
<213> ORGANISM: Artificial Sequence
<220> FEATURE:
<223> OTHER INFORMATION: IHF binding site
<220> FEATURE:
<221> NAME/KEY: W
<222> LOCATION: (1)..(1)
<223> OTHER INFORMATION: A or T
<220> FEATURE:
<221> NAME/KEY: N
<222> LOCATION: (7)..(10)
<223> OTHER INFORMATION: N may be any nucleotide
<220> FEATURE:
<221> NAME/KEY: misc_feature
<222> LOCATION: (7)..(10)
<223> OTHER INFORMATION: n is a, c, g, or t

<400> SEQUENCE: 80

watcaannnn ttr                                                          13
```

MODIFIED NUCLEIC ACID EDITING SYSTEMS FOR TETHERING DONOR DNA

TECHNICAL FIELD

The technology relates to compositions for tethering donor DNA to a nuclease the use of those compositions for improving the efficiency of in vivo gene editing.

RELATED APPLICATION

This application claims priority to Australian provisional patent application No 2018900990 filed 25 Mar. 2018 which is herein incorporated by reference in its entirety.

The instant application contains a Sequence Listing which has been submitted in ASCII format via EFS-Web and is hereby incorporated by reference in its entirety. Said SCII copy, created on Nov. 3, 2021, is named 20211103_Updated_Sequence_Listing_ST25.txt and is 77.5 KB in size.

BACKGROUND

A number of genome editing technologies are known including Transcription Activator-Like Effector Nucleases (TALENs), the CRISPR-Cas9 system (Clustered, Regularly Interspaced, Short Palindromic Repeats and CRISPR associated protein 9), and Zinc finger nucleases (ZFNs). TALENs, CRISPR-Cas9 protein and ZFNs use endonucleases to initiate double-strand breaks (DSBs) at almost any target sequence in genomic DNA and can be used for gene knockouts, gene knock-ins, gene tagging, and correction of genetic defects.

The type II bacterial clustered, regularly interspaced, short palindromic repeats (CRISPR)-associated protein 9 (Cas9) system is a tool for the targeted introduction of mutations into cellular DNA. Well-designed single guide (sg) RNAs induce Cas9-mediated double stranded breaks (DSBs) at desired target sites in cellular DNA while minimizing effects at other locations. Double stranded breaks stimulate DNA repair by at least two distinct mechanisms non-homologous end joining (NHEJ) and homology directed repair (HDR). Cas9-mediated modification of cellular DNA by NHEJ can reach efficiencies of 20-60% but because NHEJ is error-prone and introduces unpredictable patterns of insertions and deletions it is only suitable for introducing small random mutations. Co-application CRISPR-Cas9 with a single-stranded or double-stranded DNA template homologous to the sequences flanking the cleavage site on the cellular DNA enables precise genome editing by HDR-mediated incorporation of an exogenous, or donor DNA fragment. However, the frequency of HDR is inherently low and the efficiency of insertion of a donor DNA using this strategy is only 0.5-20%.

TALENs are fusions of transcription activator-like (TAL) proteins and a Fok I nuclease. TAL proteins are typically composed of 33-34 amino acid repeating motifs with two variable positions that have a strong recognition for specific nucleotide sequences. By assembling arrays of TALs and fusing them to a Fok I nuclease, specific cutting of the genome can be achieved. When two TALENs bind and meet, the Fok I domains induce a double-strand break which can inactivate a gene, or can be used to insert DNA of interest. TALENs are able to modify chromosomes with efficiency of up to about 33%.

ZFNs are a class of engineered DNA-binding proteins that allow targeted genome editing of the genome by creating double-strand breaks in DNA at desired locations. ZFNs consist of two functional domains, a DNA-binding domain comprised of a chain of Zinc-finger modules, each recognizing a unique DNA hexamer. Multiple Zinc-fingers can be assembled to form ZFN with specificity for a sequence of 24 bases or more. The second functional domain is the nuclease domain of Fok I. Using ZFNs can result in single or biallelic edits occurring at an efficiency of 1-20% of clone population.

The present inventor has developed compositions and methods that utilise the target specificity of gene editing systems such as CRISPR-Cas9, TALENs and ZFNs to tether a donor DNA to a desired target DNA sequence.

SUMMARY

In a first aspect, there is provided a composition comprising a composition for tethering donor DNA to a nuclease, the composition comprising a nucleic acid comprising donor DNA and a consensus sequence for a DNA binding domain; and at least one of:

a fusion protein comprising a nuclease coupled to a DNA binding domain for binding the consensus sequence; and a nucleic acid encoding the fusion protein.

The nuclease may be a Cas, a Transcription activator-like effector nuclease (TALEN), a meganuclease, or a Zinc Finger. In one embodiment the is a Cas proetin, for example Cas9

The fusion protein may further comprises a nuclear localization sequence.

The composition may further comprise a guide RNA that interacts with the Cas protein and a target DNA sequence.

The consensus sequence may comprise the Lac operator (SEQ ID NO: 66), the TRP operator (SEQ ID NO: 68), the TET operator (SEQ ID NO: 67), the GAL-4 binding site (SEQ ID NO: 1), or the IHF binding site (SEQ ID NO 2).

The consensus sequence may comprise a sequence with at least 80%, 85%, 90%, 95% or at least 99% identity to the Lac operator, the TRP operator, the TET operator, the GAL-4 binding site, or the IHF binding site The DNA biding domain may comprises the LAC repressor, TET repressor, TRP-repressor, GAL-4, or IHF, or a portion thereof sufficient to bind the consensus sequence.

The DNA binding domain is the LAC repressor, preferably amino acids 43-403 of SEQ ID NO 9.

The nuclease may be coupled to the DNA binding domain via a linker. The linker may comprise a sequence selected from any one of SEQ ID Nos: 3 to 7, a GGS linker, or amino acids 404-419 of SEQ ID NO 9.

In one embodiment the fusion protein comprises the LAC repressor and Cas9.

The composition may comprise a vector, wherein the vector comprises either or both of:

a. the nucleic acid comprising the donor DNA and the consensus sequence for a DNA binding domain; and b. the nucleic acid encoding the fusion protein.

The vector may further comprise a nucleic acid sequence encoding a guide RNA that interacts with the Cas9 and a target DNA sequence.

In some embodiments the fusion protein is nuclease deficient.

In a second aspect there is provided an isolated host cell comprising the composition of the first aspect.

In a third aspect there is provided a method for editing DNA in a cell, the method comprising:

contacting the cell with the composition of the first aspect under conditions suitable for the interaction of the fusion protein with a target DNA sequence.

In a third aspect there is provided a method for editing DNA in a cell, the method comprising a) contacting the cell with the composition of claim 15 under conditions suitable for the interaction of the fusion protein with a first target DNA sequence; and b) contacting the cell with a nucleic acid editing system adapted to edit the genomic DNA at a second target DNA sequence, under conditions suitable for nucleic acid editing.

The target DNA sequence may be selected from genomic DNA, mitochondrial DNA, viral DNA, or exogenous DNA.

In one embodiment the efficiency of editing is at least 50%, at least 55%, at least 60%, at least 65%, at least 70%, at least 75%, at least 80%, at least 85%, at least 90% at least 95%, or at least 99%.

The cell may be in a subject, preferably a human subject.

In a fourth aspect there is provided a kit comprising:

a nucleic acid comprising donor DNA and a consensus sequence for a DNA binding domain; and at least one of

- a fusion protein comprising a nuclease coupled to a DNA binding domain for binding the consensus sequence; and
- a nucleic acid encoding the fusion protein.

In one embodiment the fusion protein in the kit comprises a Cas protein, a Transcription activator-like effector nuclease (TALEN), a meganuclease, a Zinc Finger or a MADzyme™. In one embodiment the Cas is Cas9.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present invention may be more clearly understood, preferred embodiments will be described with reference to the following drawings and examples.

DESCRIPTION OF EMBODIMENTS

Figure 1:
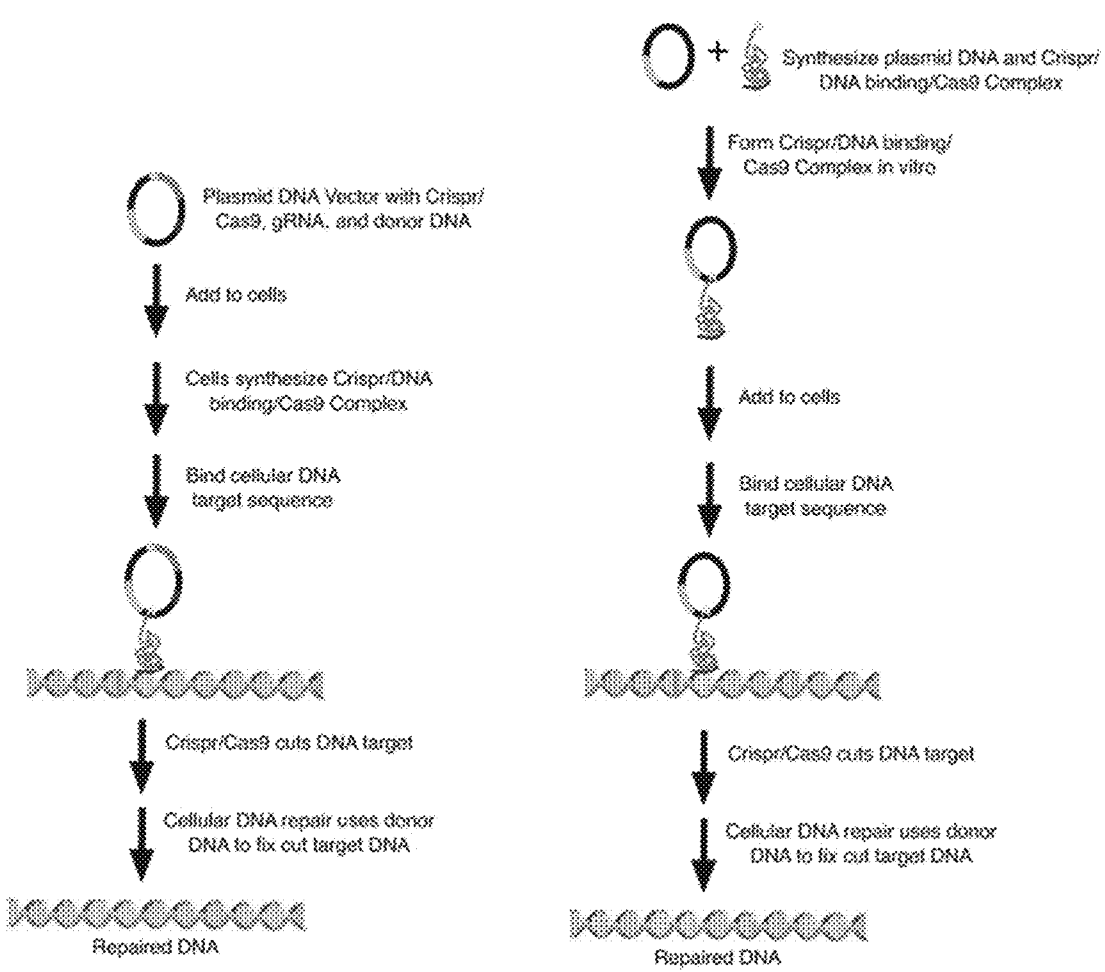
FIG. 1 is a depiction of two embodiments of the composition disclosed herein comprising a modified nucleic acid editing system.

The present disclosure provides compositions, methods, and kits for tethering donor DNA to a DNA target sequence with a modified nucleic acid editing system. The disclosure provides for improved efficiency of in vivo cellular DNA modification (such as gene editing) using a modified nucleic acid editing system, such as CRISPR-Cas9. One embodiment of this process is illustrated in FIG. 1. The modified gene editing system is adapted a bind to a nucleic acid comprising donor DNA and tether the nucleic acid to a specific site on the cellular DNA at or near to the nucleotide sequence to be edited.

Modified Nucleic Acid Editing Systems (Nuclease-DNA Binding Domain Fusions)

The compositions and methods described herein can include a nuclease of any nucleic acid editing system capable of site specific binding. For example, useful nucleases include Cas nucleases, TALENs, meganucleases, ZFNs and MADzymes™. The nuclease is modified by combining it with a DNA binding domain.

The nuclease and the DNA binding domain may be joined via linker. Suitable linkers include for example, linkers comprising the sequences (Gly-Gly-Gly-Gly-Ser)$_n$ (SEQ ID NO: 71), (Gly)$_n$, or (Gly)$_n$S, (EAAAK)$_n$ (SEQ ID NO: 72), (AP)$_n$, (XP)$_n$, or A(EAAAK)$_n$ (SEQ ID NO: 73) where n is any one of 1, 2, 3, 4, 5, 6, 7, 8, 9, 10, 11, 12, 13, 14, 15, 16, 17, 18, 19 or 20 and X is any amino acid. Other suitable linkers comprise the sequences KESGSVSSEQLAQFRSLD (SEQ ID NO: 74), EGKSSGSGSESKST (SEQ ID NO: 75), GSAGSAAGSGEF (SEQ ID NO: 76), KESGSVSSEQLAQFRSLE (SEQ ID NO: 77), or GGSAGGSGSGSSGGSSGASGTGTAGGTGSGSGTGSG (SEQ ID NO: 78).

Cas systems are divided into three major types (type I, type II, and type III) and twelve subtypes, which are based on their genetic content and structural differences. However, the core defining features of all CRISPR-Cas systems are the Cas genes and their proteins: cas1 and cas2 are universal across types and subtypes, while Cas3, Cas9, and Cas10 are signature genes for type I, type II, and type III, respectively.

Any Cas may be used. For example the Cas nuclease may be Cas1, Cas2, Cas3, Cas4, Cas5, Cas6, Cas7, Cas8, Cas9, Cas10. In some embodiments the Cas is Cas9.

Cas9 (CRISPR associated protein 9) is an RNA-guided DNA nuclease used to induce site-directed double strand breaks in DNA for the gene inactivation or the introduction of heterologous genes through non-homologous end joining and homologous recombination respectively. Systems and nucleic acids sequences for expressing Cas9 are commercially available. The Cas9 may be codon optimized for a human or other mammalian system. The Cas9 protein may contain a nuclear localization signal at the C-terminus. The RNA encoding Cas9 may be capped and polyadenylated to support expression in mammalian cells, and may contain modifications to reduce immune stimulation. The amino acid sequence and encoding nucleic acid sequence for Cas9 and functional derivatives and homologs which can be used in the compositions and methods are known in the art.

The Cas9 may be delivered in conjunction with a guide RNA (gRNA) that directs the editing system to the nucleotide sequence recognized by the gRNA. In general, a gRNA can be designed to target any nucleotide sequence. The gRNA structure is disclosed in, for example, Ran FA, Genome editing using the CRISPR-Cas9 System. PNAS 8(1 1):2281-308 (2013); and Pyzocha et al., RNA-guided genome editing of mammalian cells. Methods Mol. Biol. 1 1 14:269-77 (2014), which are hereby incorporated by reference in their entirety. Generally for Cas9, gRNAs guide the Cas9 to the complementary 20 nucleotide sequences with a downstream NGG protospacer-adjacent motif (PAM).

The CRISPR-Cas9 system including the construction of guide sequences is further disclosed in U.S. Pat. No. 8,697,359, which is hereby incorporated by reference in its entirety.

In place of a CRISPR-Cas9 system, alternate nucleic acid editing systems may be used. For example, suitable systems include any CRISPR/cas system (e.g., any Cascade-like CRISPR/cas, Type I CRISPR cas, Type II CRISPR/cas, and type III CRISPR/cas), zinc finger nucleases (ZFNs), transcription activator-like effector nucleases (TALENs), meganucleases, homing endonucleases, and MADzymes™ (for examples the Human or *E. coli* MADzymes™ encoded by SEQ ID Nos: 69 and 70, respectively.

The DNA binding domain component of the modified nucleic acid editing system can be any sequence specific high affinity DNA binding domain. The term 'DNA binding domain' as used herein refers to any complete protein or fragment thereof which can bind DNA. Accordingly the term 'DNA binding domain' includes complete proteins such as the LAC repressor and fragments of the protein which retain the DNA binding In some embodiments the DNA binding domain is not mammalian in order to reduce of target effects. For example the DNA binding domain may be from a bacteria or yeast. DNA binding domains useful in the compositions and methods described herein can be selected from the group consisting of be the LAC repressor, TET repressor, TRP-repressor, GAL-4, or IHF. Each of these bind specific consensus sequences that are known in the art.

The consensus sequence may be the Lac operator (e.g. SEQ ID NO: 66), the TRP operator (e.g. SEQ ID NO: 68), the TET operator (e.g. SEQ ID NO: 67), the GAL-4 binding site (5'-CGG-N$_{11}$-CCG-3') (SEQ ID NO: 79) or the IHF binding site (5'-WATCAANNNNTTR-3') (SEQ ID NO: 80). W is A or T, and R is A or G, and N is any nucleotide.

The nucleic acid editing systems can be present in the compositions disclosed herein in the form of purified proteins or in the form of nucleic acids encoding the nucleic acid editing system. The nucleic acid may be a vector, for example a plasmid vector comprising sequences encoding the nucleic acid editing system operably linked to a constitutive or inducible promoter.

The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors).

Other vectors (e.g., non-episomal mammalian vectors) are integrated into the genome of a host cell upon introduction into the host cell, and thereby are replicated along with the host genome. Moreover, certain vectors are expression vectors capable of directing the expression of genes to which they are operatively linked. Common expression vectors of utility in recombinant DNA techniques are often in the form of plasmids. Recombinant expression vectors can comprise one or more nucleic acids encoding a modified nucleic acid editing system in a form suitable for expression of the nucleic acid in a cell, which means that the recombinant expression vectors include one or more regulatory elements, which may be selected on the basis of the host cells to be used for expression. That is the regulatory elements are operatively-linked to the nucleic acid sequence to be expressed. 'Operably linked' means that that the nucleotide sequence of interest is linked to the regulatory element(s) in a manner that allows for expression of the nucleotide sequence (e.g. in an in vitro transcription/translation system or in a host cell when the vector is introduced into the host cell).

'Regulatory element' includes promoters, enhancers, internal ribosomal entry sites (IRES), and other expression control elements (e.g. transcription termination signals, such as polyadenylation signals and poly-U sequences). Regulatory elements are known in the art. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes).

Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol 1 promoters), or combinations thereof. Examples of pol III promoters include, but are not limited to, U6 and HI promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EFIa promoter and Pol II promoters described herein. Also encompassed by the term "regulatory element" are enhancer elements, such as WPRE; CMV enhancers; the R-U5' segment in LTR of HTLV-I; SV40 enhancer; and the intron sequence between exons 2 and 3 of rabbit β-globin. It will be appreciated by those skilled in the art that the design of the expression vector can depend on such factors as the choice of the host cell to be transformed, the level of expression desired, etc. A vector can be introduced into host cells to thereby produce transcripts (e.g. guide RNA), proteins, or peptides, including fusion proteins (such as the modified nucleic acid editing systems) or peptides.

The vector may include one or more terminator sequences. A terminator sequence includes a section of nucleic acid sequence that marks the end of a coding sequence during transcription.

The vector may include one or more sequences encoding an epitope tag or reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP). The epitope tag, reporter gene or both may be expressed from the vector as a fusion with the modified nucleic acid editing system (nuclease-DNA binding domain fusion).

Alternatively or in addition the compositions may comprise a mRNA encoding the fusion protein.

The mRNA can be modified, and the modification selected from one or more of modifications of the phosphate backbone (e.g., phosphorothioate linkages or boranophosphate linkages), ribose ring modifications such as 2'-0-methyl and/or 2'-fluoro and/or 4'-thio modifications, and locked or unlocked nucleic acids. Other modifications may include pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, 5-methylcytidine, N4-methylcytidine, 2-thiocytidine, 5-azacytidine, 5-hydroxycytidine, 5-aminocytidine, N4-methylpseudoisocytidine, 2-thiopseudoisocytidine, 5-hydroxypseudoisocytidine, 5-aminopseudoisocytidine, 5-methylpseudoisocytidine, N6-methyladenosine, 7-deazaadenosine, 6-thioguanosine, 7-deazaguanosine, 8-azaguanosine, 6-thio-7-deazaguahosine, 6-thio-8-azaguanosine, 7-deaza-8-azaguanosine, and 6-thio-7-deaza-8-azaguanosine.

In some embodiments the modifications are selected for one or more of the following: reduce immune stimulation, RNA stabilization, improve expression of the encoded protein. For example, the RNA may have a combination of 2-thiouridine and 5-methyl-cytidine to reduce immune stimulation through pattern recognition receptors such as TLR3, TLR7 and TLR8. In some embodiments, the mRNA has one or more pseudouridine to stabilize the mRNA against cleavage, and improve expression rates.

The modified nucleic acid editing systems also comprise a DNA binding domain. The DNA binding domain facilitates the localisation of the modified nucleic acid editing system to cellular DNA.

Construction of the vectors disclosed herein is by standard methods known in the art such as ligation of synthetic nucleic acids, or nucleic acids produced by, for example PCR, into a plasmid that has been cut by one or more site-specific nucleases.

There are alternative strategies for producing the vectors disclosed herein. In one approach, the entire vector(s) are synthesized de novo using a commercially available service, for example by a company that specialises in the synthesis of large DNA molecules.

Figure 7:
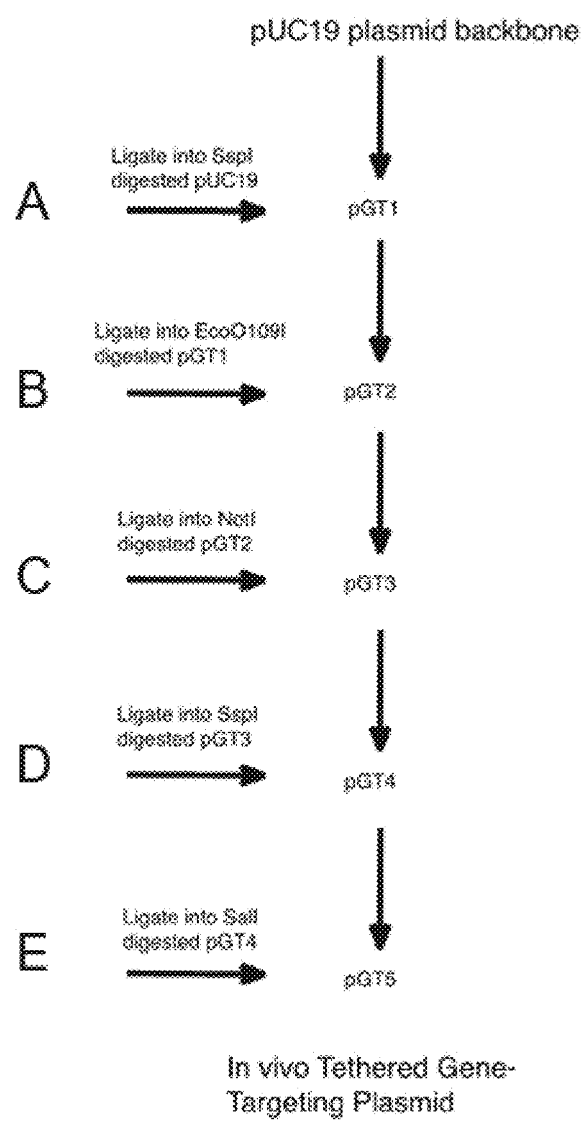
FIG. 7 is a workflow diagram for construction of an in vivo tethered gene-targeting plasmid, where A represents the synthesis of U6 expression cassette containing Ug promoter with a central SspI recognition sequence and flanking SspI compatible overhangs that do not reconstruct the plasmid SspI recognition sequence. B represents the synthesis of CMV promoter-SV40-polyA cassette containing central NotI cloning site and Eco109I compatible overhangs. C represents Synthesis of gene encoding Cas9-lac repressor fusion protein with NotI compatible overhangs. D represents synthesis of gene encoding RNA complementary to genomic target DNA sequence with SspI compatible overhangs. E represent PCR amplification of donor DNA sequence with oligonucleotide containing flanking SalI restriction endonuclease recognition sequences and digestions with SalI.
Figure 8A:
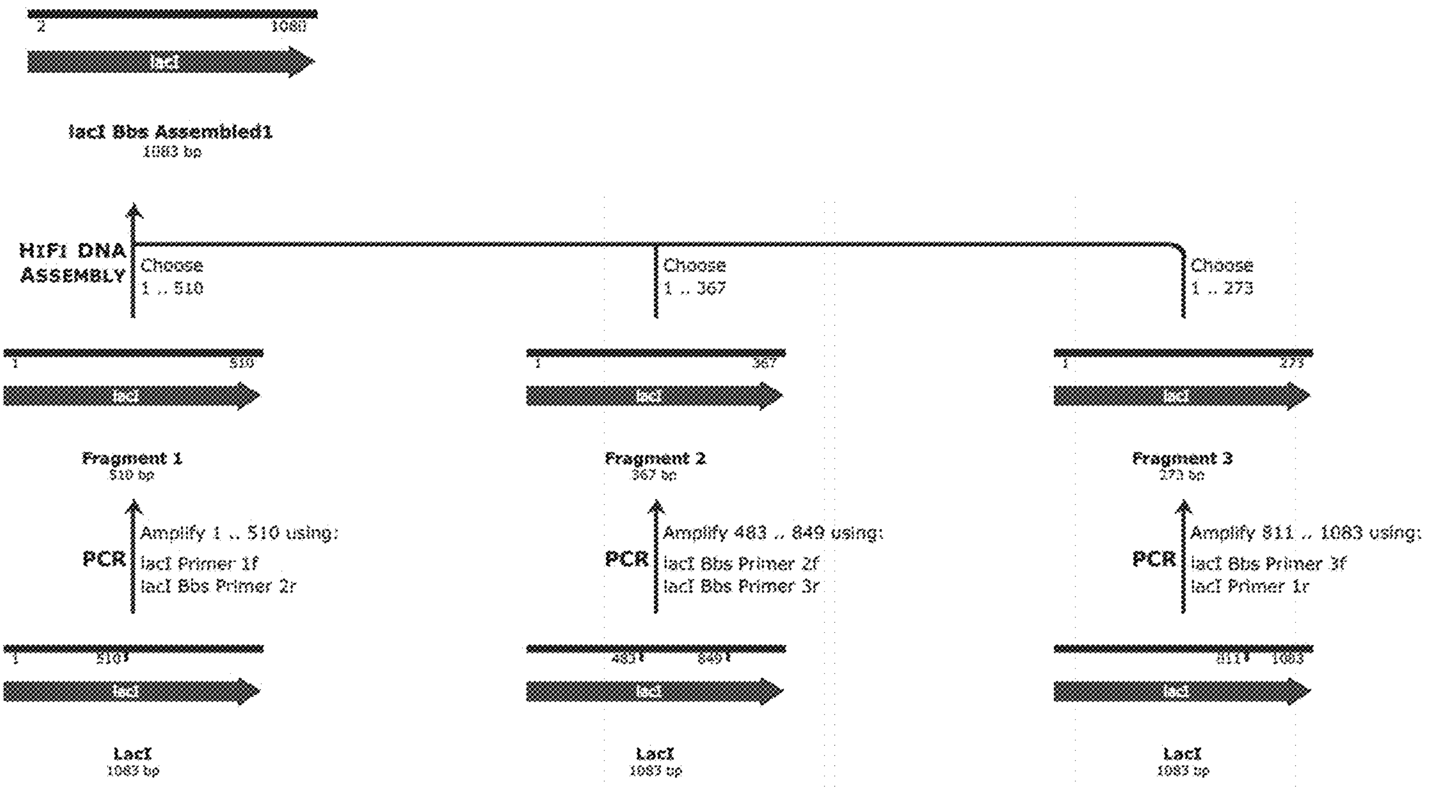
FIG. 8A is a workflow diagram for the construction of pGT1. Construction of lactose repressor gene with inactivated BbsI restriction endonuclease sites.
Figure 8B:
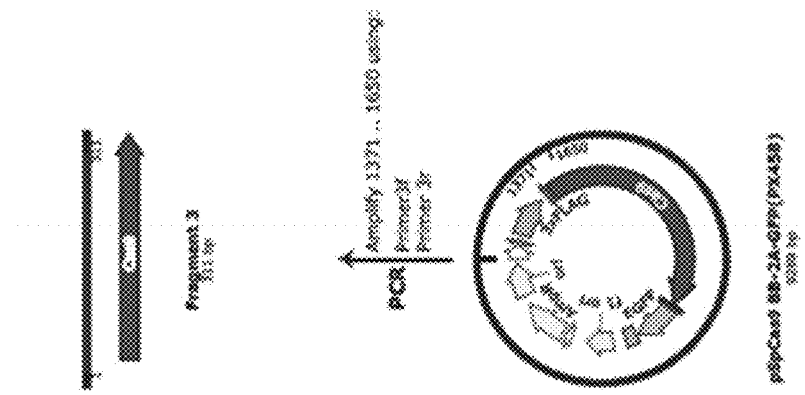
FIG. 8B is a workflow diagram for the construction of pGT1.
Figure 8B:
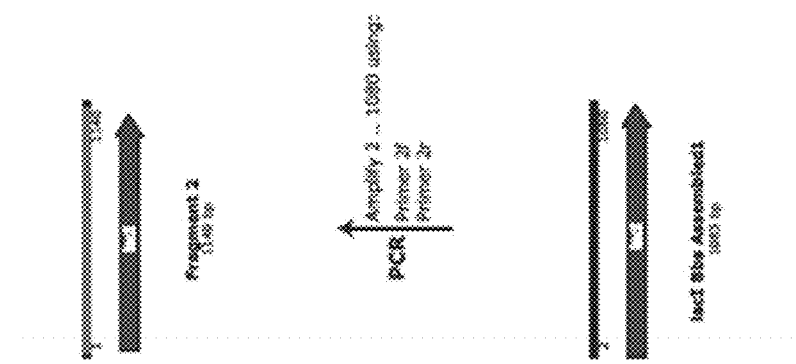
Figure 8B:
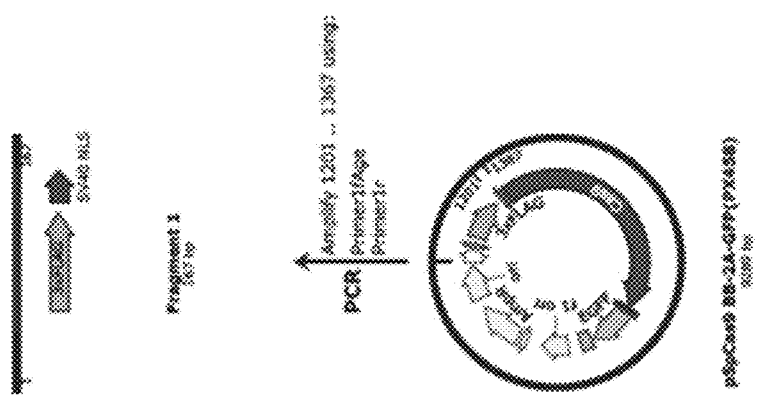
Figure 8C:
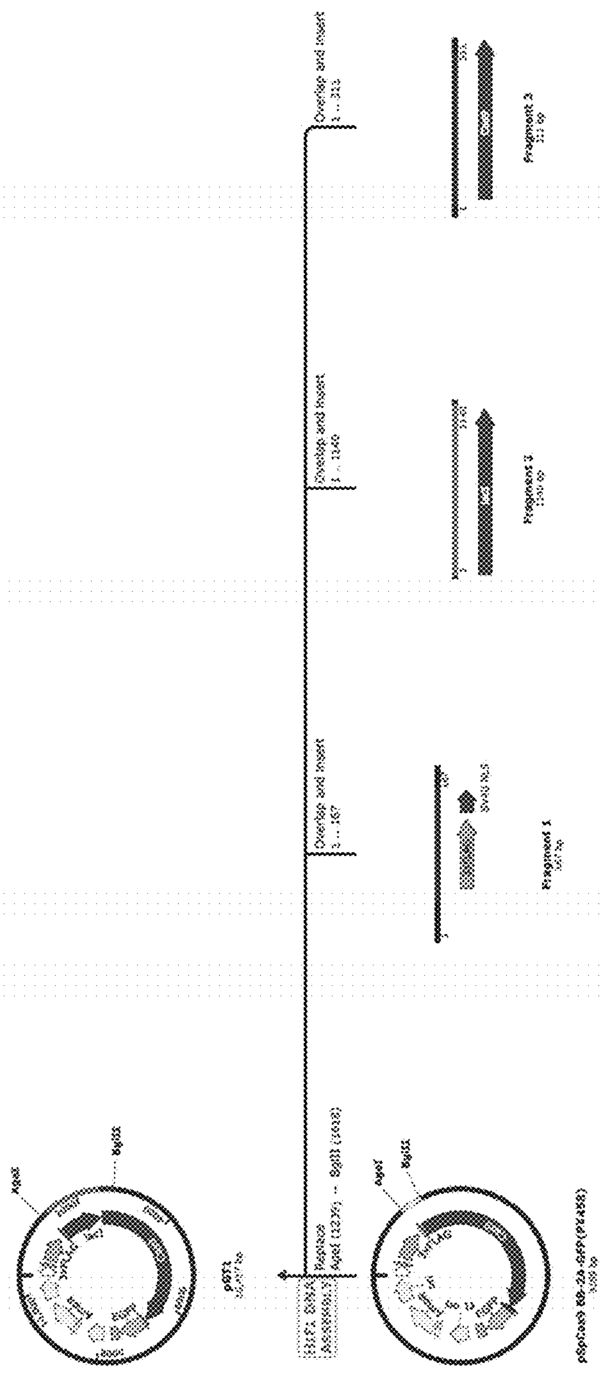
FIG. 8C is a workflow diagram for the construction of pGT1. Three overlapping DNA fragments comprising Flag/SV40 NLS, lacI and Cas9 were made, and these were cloned into pSpCas9 BB-2A-GFP(px458).
Figure 8D:
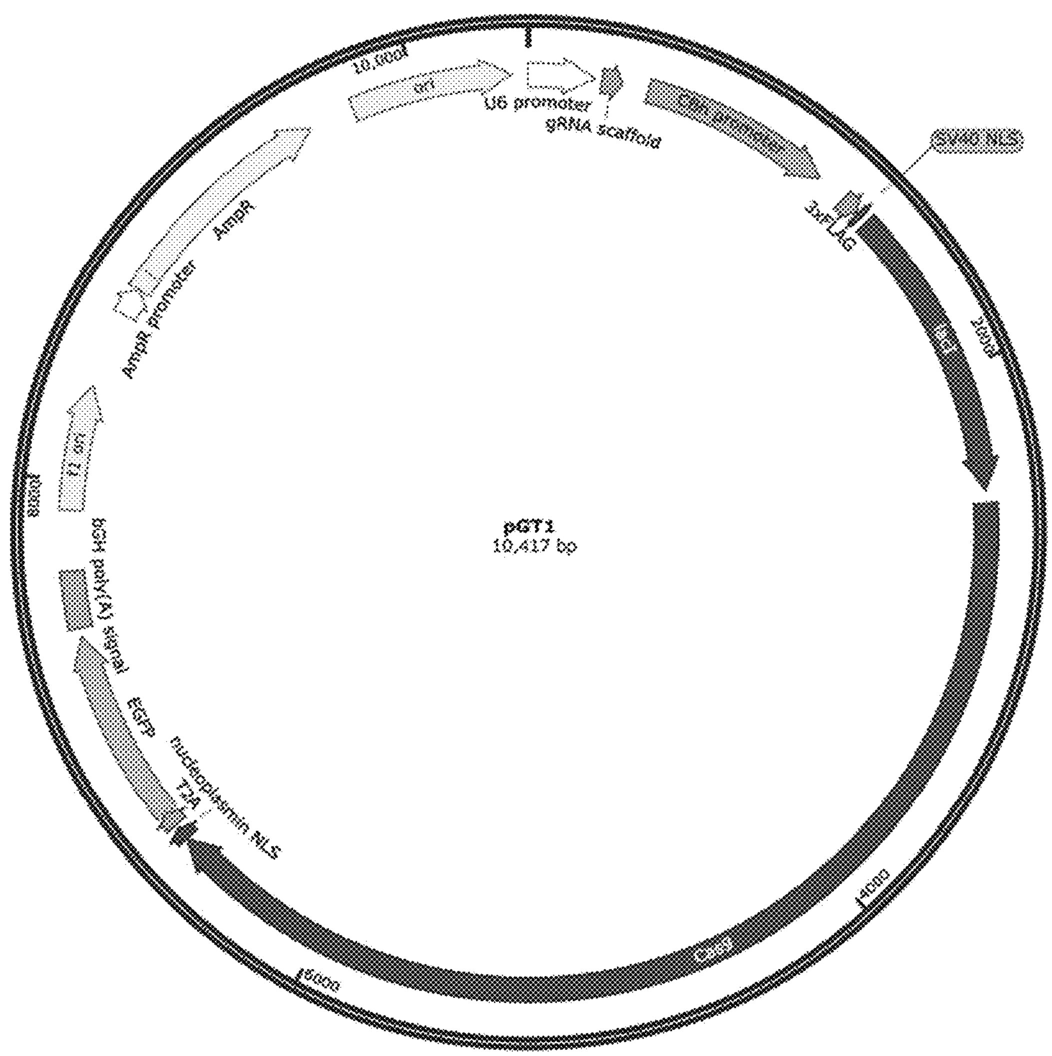
FIG. 8D is a vector map if pGT1.

Alternatively, a combination of classical cloning techniques and synthetic biology to modify a standard laboratory plasmid such as pUC19. In this approach, gene cassettes encoding the Cas9-lac operon fusion gene, guide RNA, and donor DNA sequences would be synthesized de novo and individually cloned into unique restriction endonuclease sites present in the vector backbone using T4 DNA ligase. Donor DNA sequences are amplified by polymerase chain reaction to generate products that are cloned into the vector backbone. Modification of Cas9-lac repressor fusion proteins to add other DNA binding domains or epitopes for affinity purification of modified Cas9 proteins can be performed by recombinant PCR followed by ligation into restriction endonuclease sites in the vector backbone. A workflow illustrating this process for preparing the plasmid vectors disclosed herein is shown in FIG. 7.

Nuclease Deficiency

In some embodiments the nucleic acid editing system is nuclease deficient. In these embodiments the nuclease deficient nucleic acid editing system is used to tether the donor DNA near to a target nucleic acid sequence so that donor DNA is available for use by an additional nucleic acid editing system.

For example the nuclease deficient gene editing system has reduced or eliminated nuclease activity, alternatively the nuclease activity is absent or substantially absent within levels of detection. In some embodiments the nuclease activity of the gene editing system may be undetectable using known assays, i.e. below the level of detection of known assays.

Nuclease deficient gene editing systems can be prepared by those skilled in the art using standard molecular biology techniques. Typically this involves deleting or altering one or more amino acids crucial for nuclease activity to substantially eliminate or eliminate nuclease activity.

In some embodiments the Cas9 is a nuclease-deficient Cas9. A nuclease-deficient Cas9 may be one in which one or more amino acids in Cas9 are altered or removed. For example a nuclease deficient Cas9 may be generated by removing or mutating one or more of the amino acids D10, H840, D839 and N863 (See Jinke et al., *Science* 337, 816-821 (2012). For example one or more of these amino acids may be deleted or substituted with alanine or glycine to substantially eliminates or eliminates nuclease activity.

Donor DNA

The term "donor DNA" includes a nucleic acid sequence which is to be inserted into cellular. DNA (such as of genomic DNA, mitochondrial DNA, or viral DNA). The donor nucleic acid sequence may be expressed by the cell. The donor nucleic can be exogenous, foreign to the cell or non-naturally occurring within the cell.

The donor DNA is associated with a sequence that can be bound by a DNA binding domain. For example the donor DNA may be contiguous with a consensus sequence for a DNA binding domain or may be present on the same vector as the a consensus sequence, or may be present on the same polynucleotide as the consensus sequence.

Target Nucleic Acid Sequence

A target nucleic acid sequence includes any nucleic acid sequence, such as a genomic nucleic acid sequence or a gene to which a nuclease of a nucleic acid editing system can co-localise. Target nucleic acids include nucleic acid sequences capable of being expressed into proteins. According to one aspect, the target nucleic acid is genomic DNA, mitochondrial DNA, plastid DNA, viral DNA, or exogenous DNA.

One of skill in the art will readily be able to identify or design guide RNAs, TALENs, ZFNs, meganucleases and homing endonucleases which co-localize to a target nucleic acid sequence.

Methods

The compositions and vectors described herein can be used in for editing DNA in a cell. The methods comprise contacting the cell with a composition comprising a modified gene editing system or vector encoding a modified gene editing system under conditions suitable for the interaction of the modified nucleic acid editing system with a target DNA sequence. The methods also comprise use of a nuclease-deficient modified nucleic acid editing system that interacts with a first target DNA sequence and a conventional nucleic acid editing system to edit the DNA at a second target DNA sequence.

In order to increase the efficiency of DNA editing the donor DNA is positioned close to the target DNA sequence so that it is readily available for nucleic acid editing.

In embodiments using a nuclease-deficient modified nucleic acid editing system this is achieved by spacing the first and second target sequences so that the donor DNA is closed to the conventional nucleic acid editing system when it is colocalised with its target sequence.

For example the first and second target sequences are about 75 to 150 base pairs apart, about 150-250, 250-350, 450-550, 550-650, 650-750, 750-850, 850-950, 950-1050 base pairs apart or about 1-1.5 kb apart.

The methods require delivery of the compositions or vectors to the cell. Methods of non-viral delivery of nucleic acid vectors, RNA or proteins include lipofection, microinjection, biolistics, virosomes, liposomes, immunoliposomes, polycation or lipid:nucleic acid conjugates, naked DNA, artificial virions, agent-enhanced uptake of DNA, nanoparticles, and electroporation/nucleofection. Lipofection reagents are sold commercially (e.g., Transfectam™ and Lipofectin™). Cationic and neutral lipids that are suitable for efficient receptor-recognition lipofection of polynucleotides are known. Delivery can be to cells (e.g. in vitro or ex vivo administration) or target tissues (e.g. in vivo administration). The term native includes the protein, enzyme, RNA, or guide RNA species itself as well as the corresponding nucleic acid encoding the same.

Delivery Vehicles

Delivery vehicles for the compositions and vectors disclosed herein provided herein may be viral vectors or non-viral vectors. In some embodiments, the modified nucleic acid editing system is provided in a viral vector or a non-viral vector. In other embodiments, the guide RNA is provided in a viral vector, and the modified nucleic acid editing system is provided in a non-viral vector. In still other embodiments, the guide RNA is provided in a non-viral vector and the modified nucleic acid editing system is provided in a viral vector In some embodiments, the viral vector is selected from an adeno-associated virus (AAV), adenovirus, retrovirus, and lentivirus vector. While the viral vector may deliver any component of the system described herein so long as it provides the desired profile for tissue presence or expression, in some embodiments the viral vector provides for expression of one or more of the modified nucleic acid editing system, guide RNA and optionally the delivers the donor DNA. In some embodiments, the viral delivery system is adeno-associated virus (AAV) 2/8. However, in various embodiments other AAV serotypes are used, such as AAV1, AAV2, AAV4, AAV5, AAV6, and AAV8. In some embodiments, AAV6 is used when targeting airway epithelial cells, AAV7 is used when targeting skeletal muscle cells (similarly for AAV1 and AAV5), and AAV8 is used for hepatocytes. In some embodiments, AAV1 and 5 can be used for delivery to vascular endothelial cells. Further, most AAV serotypes show neuronal tropism, while AAV5 also transduces astrocytes. In some embodiments, hybrid AAV vectors are employed. In some embodiments, each serotype is administered only once to avoid immunogenicity. Thus, subsequent administrations employ different AAV serotypes.

In some embodiments, the delivery system comprises a non-viral delivery vehicle. In some aspects, the non-viral delivery vehicle is lipid-based. In other aspects, the non-viral delivery vehicle is a polymer. In some embodiments, the non-viral delivery vehicle is biodegradable. In embodiments, the non-viral delivery vehicle is a lipid encapsulation system and/or polymeric particle.

In certain embodiments, the delivery system comprises lipid particles. In some embodiments, the lipid-based vector is a lipid nanoparticle, which is a lipid particle between about 1 and about 100 nanometers in size. In some embodiments, the lipid-based vector is a lipid or liposome. Liposomes are artificial spherical vesicles comprising a lipid bilayer.

The lipid-based vector can be a small nucleic acid-lipid particle (SNALP). SNALPs comprise small (less than 200 nm in diameter) lipid-based nanoparticles that encapsulate a nucleic acid. In some embodiments, the SNALP is useful for delivery of an RNA molecule. In some embodiments, SNALP formulations deliver nucleic acids to a particular tissue in a subject, such as the liver.

In some embodiments, the guide RNA, the modified nucleic acid editing system (or the RNA encoding the same) is delivered via polymeric vectors. In some embodiments, the polymeric vector is a polymer or polymerosome. Polymers encompass any long repeating chain of monomers and include, for example, linear polymers, branched polymers, dendrimers, and polysaccharides. Linear polymers comprise a single line of monomers, whereas branched polymers include side chains of monomers. Dendrimers are also branched molecules, which are arranged symmetrically around the core of the molecule. Polysaccharides are polymeric carbohydrate molecules, and are made up of long monosaccharide units linked together. Polymersomes are artificial vesicles made up of synthetic amphiphilic copolymers that form a vesicle membrane, and may have a hollow or aqueous core within the vesicle membrane.

Various polymer-based systems can be used for administering RNA encoding modified nucleic acid editing system. Exemplary polymeric materials include poly(D,L-lactic acid-co-glycolic acid) (PLGA), poly(caprolactone) (PCL), ethylene vinyl acetate polymer (EVA), polylactic acid) (PLA), poly(L-lactic acid) (PLLA), poly(glycolic acid) (PGA), polyp lactic acid-co-glycolic acid) (PLLGA), poly (D,L-lactide) (PDLA), poly(L-lactide) (PLLA), PLGA-b-poly(ethylene glycol)-PLGA (PLGA-bPEG-PLGA), PLLA-bPEG-PLLA, PLGA-PEG-maleimide (PLGA-PEG-mal), poly(D,L-lactide-co-caprolactone), poly(D,L-lactide-co-caprolactone-co-glycolide), poly(D,L-lactide-co-PEO-co-D, L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly (vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly (isobutyl(mefh)acrylate), poly(hexyl(meth)acrylate), poly(isodecyl(meth)acrylate), poly(lauryl(meth)acrylate), poly (phenyl(mefh)acrylate), poly(methyl acrylate), poly (isopropyl acrylate), poly(isobutyl acrylate), poly(octadecyl acrylate) (polyacrylic acids), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, polyvinylpyrrolidone, polyortho esters, polyphosphazenes, Poly([beta]-amino esters (PBAE), and polyphosphoesters, and blends and/or block copolymers of two or more such polymers. Polymer-based systems may also include Cyclodextrin polymer (CDP)-based nanoparticles such as, for example, CDP-admantane (AD)-PEG conjugates and CDP-AD-PEG-transferrin conjugates.

In one embodiment, nanoparticles are formulated with Cas9 mRNA chemically modified to reduce TLR responses, as disclosed in Kormann et al. Expression of therapeutic proteins after delivery of chemically modified mRNA in mice. Nat. Biotechnol. 29: 154-157 (2011). In a further embodiment, the nanoparticles are formulated using controlled microfluidic mixing systems, as disclosed in, for example, Chen et al. Rapid discovery of potent siRNA-containing lipid nanoparticles enabled by controlled microfluidic formulation. J. Amer. Chem. Soc. 134:6948-6951 (2012).

In some embodiments, the lipid-based delivery system comprises a lipid encapsulation system. The lipid encapsulation system can be designed to drive the desired tissue distribution and cellular entry properties, as well as to provide the requisite circulation time and biodegrading character. The lipid encapsulation may involve reverse micelles and/or further comprise polymeric matrices. In some embodiments, the particle includes a lipophilic delivery compound to enhance delivery of the particle to tissues, including in a preferential manner. Such compounds may generally include lipophilic groups and conjugated amino acids or peptides, including linear or cyclic peptides, and including isomers thereof.

The lipid or polymeric particles may have a size (e.g., an average size) in the range of about 50 nm to about 5 μm. In some embodiments, the particles are in the range of about 10 nm to about 100 μm, or about 20 nm to about 50 μm, or about 50 nm to about 5 μm, or about 70 nm to about 500 nm, or about 70 nm to about 200 nm, or about 50 nm to about 100 nm. Particles may be selected so as to avoid rapid clearance by the immune system. Particles may be spherical, or non-spherical.

In some embodiments, the non-viral delivery vehicle may be a peptide, such as a cell-penetrating peptides or cellular internalization sequences. Cell penetrating peptides are small peptides that are capable of translocating across plasma membranes. Exemplary cell-penetrating peptides include, but are not limited to, Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB I, Pep-7, I-IN-1, BGSC (Bis-Guanidinium-Spermidine-Cholesterol, and BGTC (B is-Guanidinium-Tren-Cholesterol).

In some embodiments, the guide RNA or RNA encoding the modified nucleic acid editing system is modified at the 5' end or the 3' end In a preferred embodiment, the modification is made at the 3' end of the RNA. The RNA may be modified by conjugating to cholesterol, other lipophilic molecules, polymers, peptides, antibodies, aptamers, and/or small molecules. In some embodiments, the RNA is conjugated to a N-acetylgalactosamine (GalNAc). GalNAc binds the asialoglycoprotein receptor (ASGPR) on hepatocytes, and therefore can be used to target an RNA to the liver. In some embodiments, the RNA is conjugated to a trivalent targeting ligand, e.g., triantennary GalNAc. Such conjugates comprise an RNA conjugated at the 3' terminus to three GalNAc molecules.

The delivery vehicles (e.g. conjugates, viral or non-viral vectors, or any combination thereof) may be administered by any method known in the art, including injection, optionally by direct injection to target tissues. In some embodiments, the guide RNA, modified nucleic acid editing system, and, optionally, donor DNA are administered simultaneously in the same or in different delivery vehicles. In other embodiments, the guide RNA and modified nucleic acid editing system and, optionally, donor DNA are administered sequentially via the same or separate delivery vehicles. In some embodiments, the guide RNA and/or donor DNA is administered 1, 3, 5, 7, 10, 14, or 30 days prior to administration of the modified nucleic acid editing system, such that the guide RNA and/or donor DNA accumulates in the target cell or tissue prior to administration of the modified nucleic acid editing system. In some embodiments, the guide RNA, donor DNA and/or nucleic acid editing system is administered in a plurality of doses, such as 2, 3, 4, 5, 6, 7, 8, 9, 10, 11, 12, 13, 14, 15, 16, 17, 18, 19, 20, or more doses. In various embodiments, the gRNA, donor DNA and/or nucleic acid editing system is administered over a time period of from one day week to about a month.

In one embodiment, one or both of the guide RNA and donor DNA, are provided in an AAV vector that is administered to the tissue or cell prior to administration of the modified nucleic acid editing system. In a further embodiment, the AAV vector comprising the gRNA is administered 1, 2, 3, 4, 5, 6, 7, 8, 9, or 10 days prior to the administration of the nanoparticle modified nucleic acid editing system, to allow expression of the guide RNA from the AAV vector. In a yet further embodiment, the modified nucleic acid editing system is administered multiple times, for example, once every 1, 2, 3, 4, 5, 6, 7, 8, 9, 10, 11, 12, 13, 14, or 15 days.

In another embodiment, the donor DNA is delivered via an AAV vector, and is injected 1, 2, 3, 4, 5, 6, 7, 8, 9, or 10 days prior to the administration of either or both of the modified nucleic acid editing system and the guide RNA.

In particular embodiments, either or both of guide RNA and donor DNA are provided in an AAV vector that is administered first, and the modified nucleic acid editing system is administered subsequently in a lipid-based delivery vehicle in one or more doses.

In another embodiment, each component of the compositions described herein (e.g., the modified nucleic acid editing system, guide RNA and donor DNA) are each delivery using a different vehicles, alternatively one or more components may be used with the same deliver vehicle. In a further embodiment, the modified nucleic acid editing system, guide RNA, and donor DNA, are administered at multiple time points, for example, every 1, 2, 3, 4, 5, 6, 7, 8, 9, 10, 11, 12, 13, 14 or 15 days. In another embodiment, the administration of the modified nucleic acid editing system, guide RNA and donor DNA are administered at different time points.

In some embodiments, expression of the modified nucleic acid editing system is transient. In some embodiments, such transient expression of the modified nucleic acid editing system minimizes off-target effects. For example, expression of the modified nucleic acid editing system is controlled via selection of the delivery vehicles and/or promoters.

In some embodiments, the present disclosure provides compositions and methods that allow for increased safety and/or efficacy of conventional nucleic acid editing systems. Advantageously, the methods disclosed herein provide for repeated dosing with conventional and modified nucleic acid editing systems such that the efficiency of gene editing increases with each dose. For example, in some embodiments, the methods disclosed herein result in an increase in efficiency of gene editing by conventional nucleic acid editing systems when used in conjunction with the modified nucleic acid editing systems disclosed herein. For example the percentage efficiency of gene editing increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, or more.

In another embodiment at least one of the guide RNA, modified nucleic acid editing system, and donor DNA are administered to a tissue or cell at the same time, such as on the same delivery vehicle, and one or more component (i.e., the modified nucleic acid editing system, and guide RNA) is under the control of an inducible promoter. As an example, in one embodiment the inducible promoter may be for example a small molecule-induced promoter such as tetracycline-inducible promoter.

The delivery vehicles (whether viral vector or non-viral vector or RNA conjugate material) may be administered by any method known in the art, including injection, optionally by direct injection to target tissues or cells. Nucleic acid modification can be monitored over time by, for example, periodic biopsy with PCR amplification and/or sequencing of the target region from genomic DNA, or by RT-PCR and/or sequencing of the expressed transcripts. Alternatively, nucleic acid modification can be monitored by detection of a reporter gene or reporter sequence. Alternatively, nucleic acid modification can be monitored by expression or activity of a modified gene product or a therapeutic effect in the cell or tissue or in a subject.

In some embodiments, the cell or tissue is in a subject. For example the subject may be a human, in particular a human in need of therapeutic or prophylactic intervention. Alternatively, the subject is an animal, including livestock, poultry, domesticated animal, or laboratory animal. In various embodiments, the subject is a mammal, such as a human, horse, cow, dog, cat, rodent, or pig.

In some embodiments, the methods provided herein include obtaining a cell or population of cells from a subject and modifying a target polynucleotide in the cell or cells ex vivo, using the delivery systems, compositions, methods, and/or kits disclosed herein. In further embodiments, the ex vivo modified cell or cells may be re-introduced into the subject following ex vivo modification. Thus, the present disclosure provides methods for treating a disease or disorder in a subject, comprising obtaining one or more cells from the subject, modifying one or more target nucleotide sequences in the cell ex vivo using both conventional and the modified nucleic acid editing systems described herein and re-introducing of the cell with the modified target nucleotide sequence back into the subject having the disease or disorder. In some embodiments, cells in which nucleotide sequence modification has occurred are expanded in vitro prior to reintroduction into the subject having the disease or disorder.

In other embodiments, at least one of the modified nucleic acid editing system, guide RNA and donor DNA are administered to a cell in vitro.

In some embodiments, at least one component (e.g., the guide RNA, donor, modified nucleic acid editing system or nucleic acid vector) accumulates in a cell or tissue which may be, for example, liver, heart, lung (including airway epithelial cells), skeletal muscle, CNS (e.g., nerve cells), endothelial cells, blood cells, bone marrow cells, blood cell precursor cells, stem cells, fat cells, or immune cells. Tissue targeting or distribution can be controlled by selection and design a viral delivery vehicle, or in some embodiments is achieved by selection and design of lipid or polymeric delivery vehicles.

In some embodiments, the percentage efficiency of target sequence modification (editing) using the methods disclosed herein is at least 50%, at least 55%, at least 60%, at least 65%, at least 70%, at least 75%, at least 80%, at least 85%, at least 90% at least 95%, or at least 99%.

In some embodiments, the efficiency of target sequence modification (editing) using the methods and compositions disclosed herein provides a 2-fold, 3-fold, 4-fold, 5-fold, 6-fold, a 7-fold increase or more compared to methods of making the same modification (edit) without tethering the donor DNA.

In some embodiments, the efficiency of target sequence modification is less than 100%, or wherein an effect on fewer than 100% of the cells has a therapeutic effect. For example, a therapeutic effect may be achieved when the efficiency of nucleic acid modification of about 0.01% to about 100%, about 0.01% to about 50%, about 0.05% to about 40%, about 0.1% to about 30%, about 0.5% to about 25%, about 1% to about 20%, about 1% to about 15%, about 1% to about 10%, or about 1% to about 5%. Thus, even if the efficiency of nucleotide sequence modification is relatively low (e.g., less than 50%, or less than 40%, or less than 30%, or less than 20%, or less than 10%, or less than 5%, or less than 1%, or less than 0.5%, or less than 0.1%), modest expression of the introduced or corrected or modified gene product may result in a therapeutic effect in the disease or disorder.

In some embodiments, the delivery systems and compositions disclosed herein are formulated such that the ratio of the components is optimized for consistent delivery to the target sequence. In one embodiment, the ratio of the guide RNA and modified nucleic acid editing system is optimized for consistent delivery to the target sequence. In another embodiment, the ratio of the donor DNA to the guide RNA and/or to the modified nucleic acid editing system is optimized for consistent delivery to the target sequence. For example, in one embodiment, the ratio of modified Cas9: guideRNA:donor is from about 1:1:1 to about 1:1:100. In a further embodiment, the ratio is from about 1:1:2 to about 1:1:90, from about 1:1:5 to about 1:1:75, or from about 1:1:10 to about 1:1:50. In other embodiments, the ratio is about 1:1:1 or below, such as from about 1:1:0.01 to about 1:1:1, from about 1:1:0.02 to about 1:1:0.75, or about 1:1:0.05 to about 1:1:0.5, or about 1:1:0.1 to about 1:1:0.5. In other embodiments, wherein the composition does not include a guide RNA, the ratio of modified nucleic acid editing system:donor DNA is from about 1:100 to about 100:1, or about 1:50 to about 50:1, or about 1:25 to about 25:1, or about 1:10 to about 10:1, or about 1:5 to about 5:1, or about 1:2 to about 2:1, or about 1:1.

Kits

In one aspect, there is provides kits containing any one or more of the components disclosed in the above methods, compositions, and delivery systems. Kit components may be provided individually or in combinations, and may be provided in any suitable container, such as a vial, a bottle, or a tube. In some embodiments, the kits disclosed herein comprise one or more reagents for use in the embodiments disclosed herein. For example, a kit may provide one or more reaction or storage buffers. Reagents may be provided in a form that is usable in a particular method, or in a form that requires addition of one or more other components before use (e.g. in concentrate or lyophilized form). Suitable buffers include, but are not limited to, phosphate buffered saline, sodium carbonate buffer, sodium bicarbonate buffer, borate buffer, Tris buffer, MOPS buffer, HEPES buffer, and combinations thereof. In some embodiments, the buffer is alkaline. In some embodiments, the buffer has a pH from about 7 to about 10.

For example, a kit may comprise: a donor DNA and a modified nucleic acid editing system. The kit may further comprise a guide RNA. The kit may provide an expression system providing for expression of either or both of the modified nucleic acid editing system and guide RNA in a target cell. The kit may provide one or more doses of an RNA delivery system, each dose providing for expression of the modified nucleic acid editing system in the target cell or tissue.

The kit may be custom made for use with user defined target sequences.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

Figure 2:
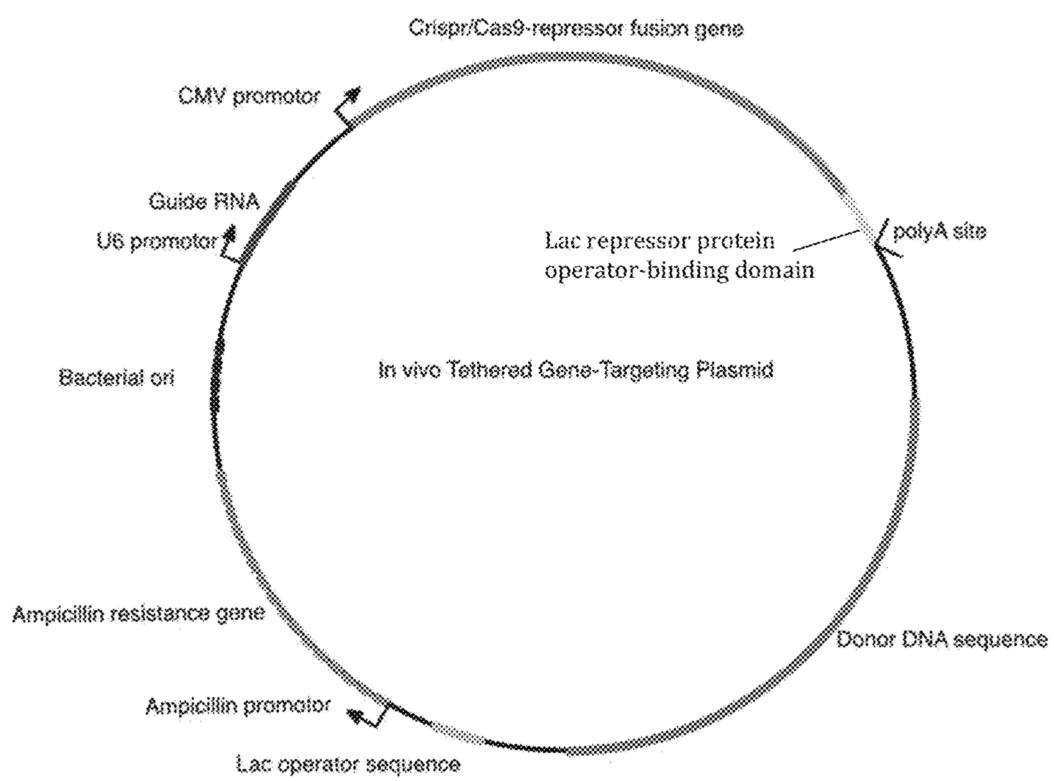
FIG. 2 is a map of a plasmid vector containing an active Cas 9 gene sequence and its guide RNA capable of directing binding of the Crispr/Cas9 complex to a genomic target DNA sequence, donor DNA sequence that can be used for repair of Crispr/Cas9 induced double strand breaks.

Example 1: Plasmid for Tethering Crispr/Cas9 Complex to a Genomic Target DNA Sequence FIG. 2 is a map of a plasmid vector containing an active Cas 9 gene sequence and its guide RNA. The coding sequence of Cas9 is contiguous with a lac repressor DNA binding domain. This fusion is operably linked to a CMV promoter. When expressed lac repressor DNA binding domain binds the lac operator sequence in the plasmid backbone sequence.

Donor DNA complementary to a genomic target DNA sequence is also cloned into the vector and provides a template for homologous recombination between the Crispr/Cas9 generated double-strand break in the target DNA sequence. In one embodiment the donor DNA sequence is modified to prevent binding of the Crispr/Cas9 nuclease to plasmid sequence and contains selectable markers to aid in identification of recombinant cell lines. It is contemplated that the donor DNA sequence may contain mutant DNA sequences to change the function of the target chromosomal gene or it may contain a 'wild type' sequence to correct a mutant target DNA sequence.

Example 2: Plasmids for a Binary Tethering System

Figure 3:
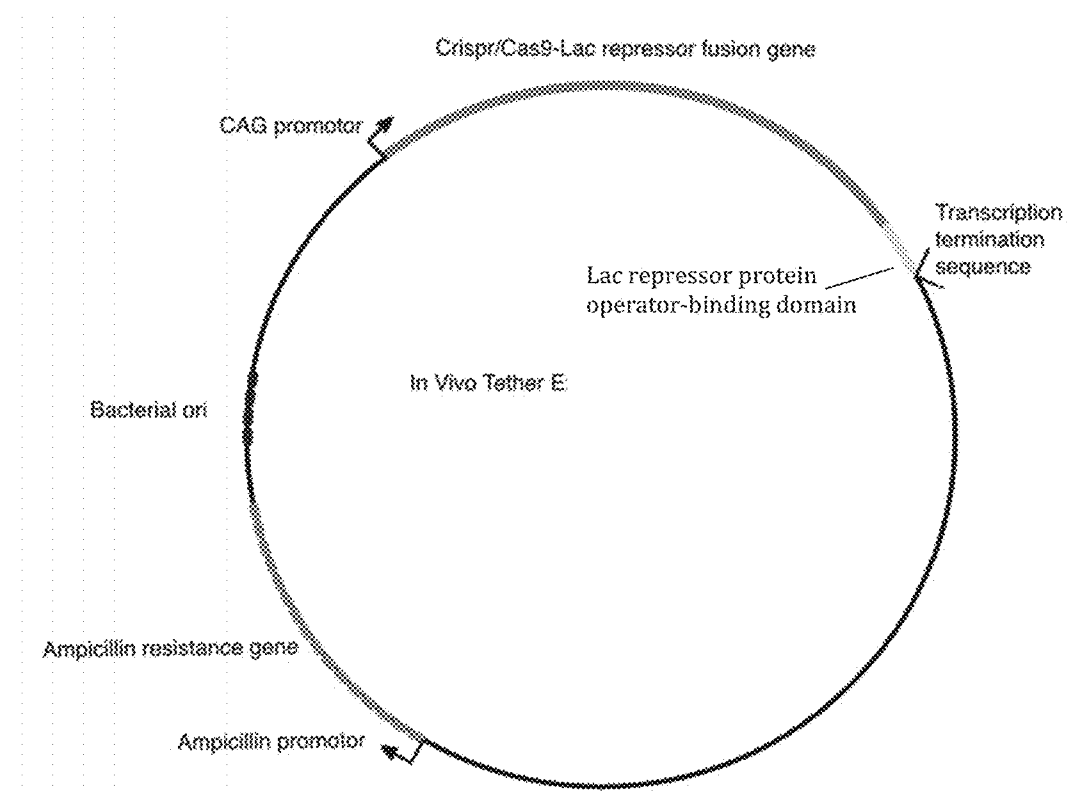
FIG. 3 is a map of a plasmid used in a binary system where the Crispr/Cas9 gene sequence containing the lac repressor fusion and guide RNA are present on a tether expression vector and the donor DNA sequence is present on a second tethered gene targeting vector.
Figure 4:
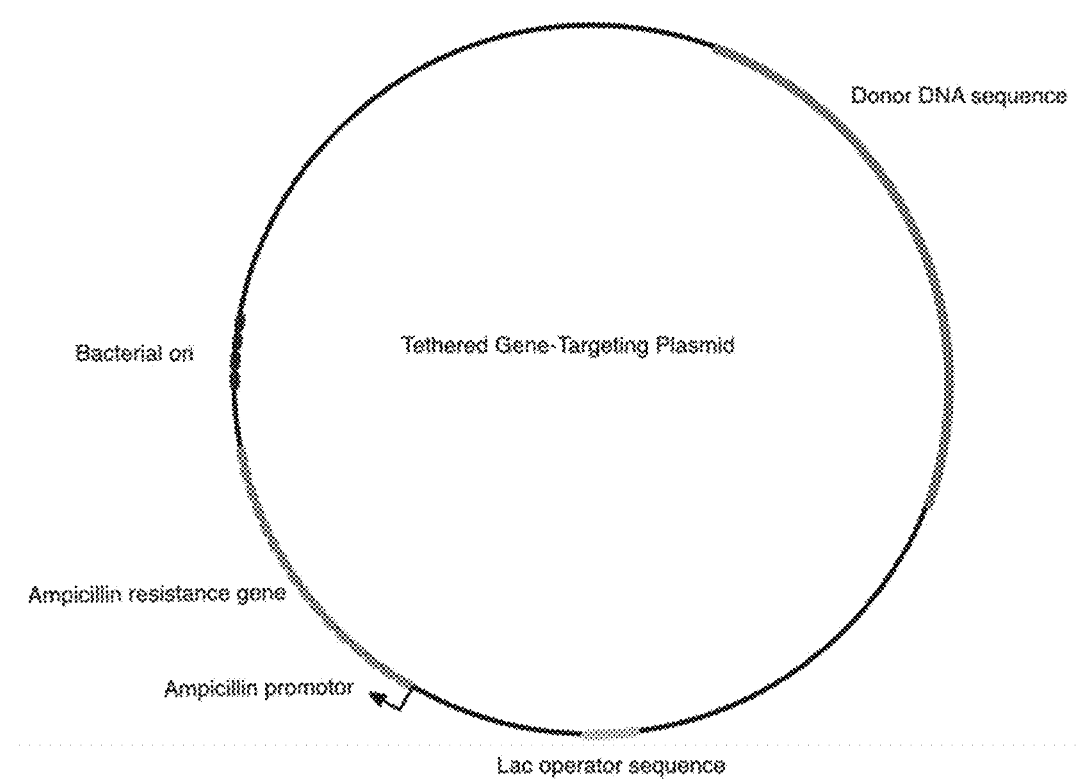
FIG. 4 is a map of a plasmid used in a binary system where the Crispr/Cas9 gene sequence containing the lac repressor fusion and guide RNA are present on a tether expression vector and the donor DNA sequence is present on a second tethered gene targeting vector.

FIGS. 3 and 4 are maps of plasmids used in a binary system where the Crispr/Cas9 gene sequence containing the lac repressor fusion and guide RNA are present on a tether expression vector (FIG. 3) and the donor DNA sequence is present on a second tethered gene targeting vector (FIG. 4). Co-transfection of both vectors is necessary for expression of the target-specific Crispr/Cas9/lac repressor nuclease binds the lac operator sequence on the tethered targeting plasmid (FIG. 4) thus localizing the gene targeting plasmid to the target DNA.

The sequences of complementary oligonucleotides used to clone the lactose operator sequence or tetracycline resistance operator sequence into HindIII/SalI restriction endonuclease digested pUC19. The correct orientation allows subsequent cloning of LacO and TetO duplexes into pUC19 to generate plasmids with one or more sequential operators that can be used to clone donor DNA molecules for gene editing by homology directed recombination in mammalian cells.

TABLE 1

LacO and TetO Oligonucleotides.

| Name | Sequence | SEQ ID NO |
| --- | --- | --- |
| tetO w | TCGAGTTTACCACTCCCTATCAGTGATAGAGAAAA GTGAAAG | 59 |
| tetO c | TCGACTTTCACTTTTCTCTATCACTGATAGGGAGT GGTAAAC | 60 |
| lacO w | TCGAGTTTAGTGGAATTGTGAGCGGATAACAATTT CACTGAAAG | 61 |
| lacO c | TCGACTTTCAGTGAAATTGTTATCCGCTCACAATT CCACTAAAC | 62 |

Example 3: Plasmids for an In Vitro Tethering System

Figure 5:
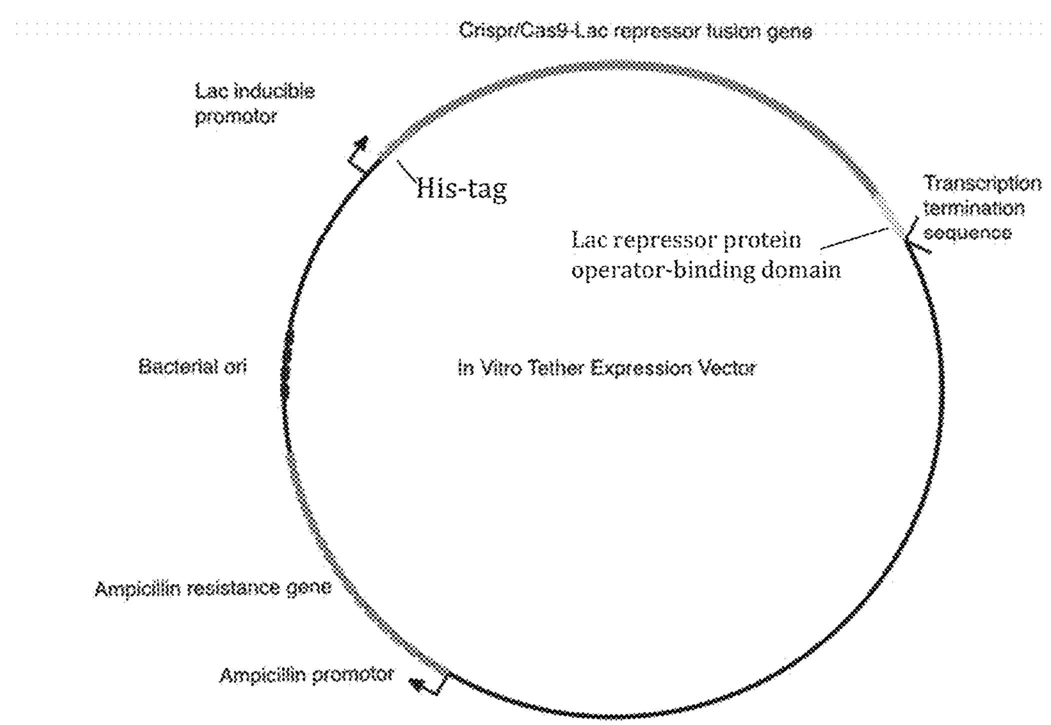
FIG. 5 is a map of a plasmid for generating an in vitro system whereby purified Crispr/Cas9 would is used to bind a gene targeting vector prior to transfection into cells.
Figure 6:
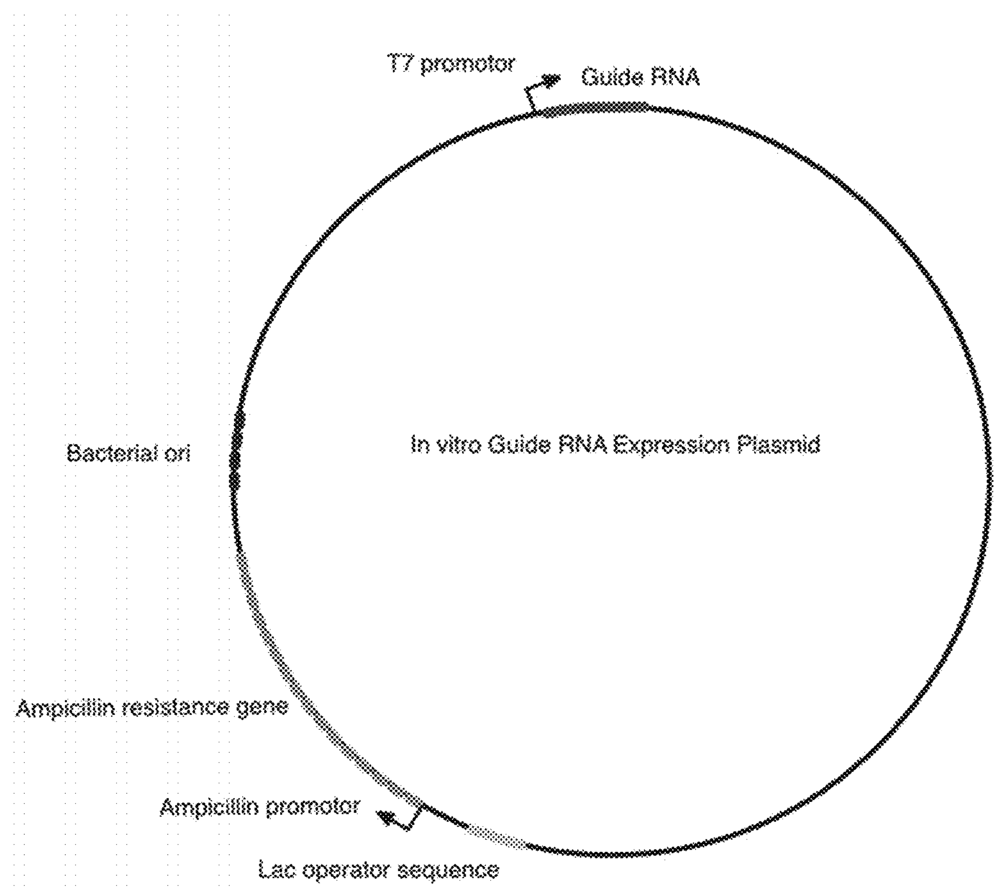
FIG. 6 is a map of a plasmid for generating an in vitro system whereby purified Crispr/Cas9 would is used to bind a gene targeting vector prior to transfection into cells.

FIGS. 5 and 6 are plasmid maps of vectors for an in vitro tethering system whereby purified Crispr/Cas9 is used to bind a gene targeting vector prior to transfection into cells. The His-tagged Crispr/Cas9-lac repressor fusion is expressed from the plasmid shown in FIG. 5, the fusion is then purified by immobilized metal affinity chromatography. FIG. 5 indicates that the Lac represser protein operator-binding domain is fused to the c-terminus of the CAS9 9. However, as set out in SEQ ID NOS: 8 and 9 a preferable arrangement is that the lac repressor is fused to the N-terminus of Cas9 preferably using a linker such as the XTEN linker. In any case the purified fusion protein is the mixed with a gene targeting vector (i.e. FIG. 4). The complex of purified fusion protein and gene targeting vector is transfected into cells with the guide RNA expression plasmid (FIG. 6).

Example 4. Gene Editing of the Cystic Fibrosis Transmembrane Conductance Regulator (CFTR) Gene by GeneTethered Donor DNA Fragments Cystic fibrosis is one of the most prevalent genetic diseases found in the Caucasian population with as many as 1/27 individuals carrying a mutation in the CFTR gene. The most common mutation found in CF patients is the delF508, or F508del, mutation that is the result of an in frame 3 base pair deletion in exon 11 resulting in a loss of phenylalanine at residue 508 in the protein. Several immortalized human cell lines have been generated from CF patients, including the CFBE41o-cell line homozygous for the delF508 mutation. The CFTR gene sequence in HEK293 cells, however, is a normal, or wild type, CFTR gene sequence.

In this example, the px458 Cas9 vector was modified by engineering a lactose repressor protein, or tetracycline repressor protein, fused in frame with the Cas9 protein sequence to create a "GeneTether". This GeneTether modification enables binding of donor DNA molecules used for gene editing to the functional Cas9 protein and localizes the donor DNA molecule at the Cas9-generated double strand break to enhance homology directed repair, reduce on-target mutations, and reduce induction of the P53 DNA repair system. These modified Cas9 proteins were transfected into cells with donor DNA molecules containing lactose operator or tetracycline operator DNA sequences to measure the gene editing efficiency introducing the delF508 mutation into the normal HEK293 CFTR gene Construction of Lac and Tet Tether Modified Cas9.

The lactose and tetracycline repressor proteins bind well-defined operator sequences with high specificity and affinity. GeneTethers are lactose or tetracycline repressor proteins fused with Cas9 (and other Cas proteins), TALENS, or ZNF with that will bind to DNA molecules containing the respective operator sequences. Binding of GeneTether-modified Cas proteins, TALENs, or ZNF to their genomic target will thereby physically localize any DNA molecules, bound to the repressor protein fusion, to the same genomic site (FIG. 1). Localization of DNA molecules, homologous to the genomic DNA target sequences, enhance the efficiency of gene editing by the homologous directed recombination DNA repair pathways and minimize DNA mutations.

Construction of Lactose Repressor-Modified Cas9

The lactose repressor gene was amplified by polymerase chain reaction from *Escherichia coli* DH5α using lacI Primer 2f/Primer 2r (Table 2) and the Q5 high fidelity thermostable polymerase (New England Biolabs) according to vendor instructions. The 1083 base pair product was gel-purified (Monarch DNA Gel Extraction Kit, New England Biolabs) and used for further modifications. Two BbsI restriction endonuclease sites in the Lactose repressor gene sequence were inactivated using polymerase chain reaction amplification with the mutagenic primers lacIBbs2f, lacIBbs2r, lacIBbs3f, and lacIBbs3r to generate A to G transitions in codons 164 and 277, retaining glutamic acid codons (Figure LacIBbsAssembled). Three gel-purified, Q5 high fidelity polymerase, polymerase chain reaction products using primer pairs lacI primer 1f/lacI Bbs Primer 2r, lacI Bbs Primer 2f/lacI Bbs Primer 3r, and lacI Bbs Primer 3f/lacI Primer 1 r (Table 2) were used to reconstruct the full length 1083 base pair BbsI-inactivated Lactose repressor protein gene (NEBuilder HiFi Assembly, New England Biolabs).

TABLE 2

| PCR Primer DNA Sequences. | | |
|---|---|---|
| Primer | Sequence | SEQ ID NO |
| CF1Bf | CCTTCTCTGTGAACCTCTATCA | 10 |
| CF1f | GCAGAGTACCTGAAACAGGA | 11 |
| CF5r | CATTCACAGTAGCTTACCCA | 12 |
| CF7Cr | ATAGGAAACACCAAAGATGA | 13 |
| CF8Cr | ATAGGAAACACCAATGATAT | 14 |
| CF8Crfull | ATAGGAAACACCAATGATATTTTCTTTAATGGTGCCAGGC | 15 |
| CF9Cf | GAAAATATCATTGGTGTTTCCTATGATGAATATAGATACA G | 16 |
| CF96250f | TGAGTTAGATGTTTGACGC | 17 |
| CF96310f | GCTGTGCATTTTCCTCTGGGTAATACTTTAG | 18 |
| CF98236f | GTCTCTATTACTTAATCTGTACCT | 19 |
| CF98328f | CTGTGAAGATTAAATAAATTAATATAGTTAAAGCAC | 20 |
| CF99287r | ATGCTCATTCCATTAGGCTATAGTATTA | 21 |
| CF99310r | CTAATTCTCTGCTGGCAGATCAATGC | 22 |
| CF101310r | CAAGACGTTGTGTTAGGTACATTACATGTACATC | 23 |
| lacl Bbs Primer 2f | CTCCCATGAGGACGGTACGCGACTGGGC | 24 |
| lacl Bbs Primer 2r | GCCCAGTCGCGTACCGTCCTCATGGGAG | 25 |
| lacl Bbs Primer 3f | GTGGGATACGACGATACCGAGGACAGCTCATGTTATATC | 26 |
| lacl Bbs Primer 3r | GATATAACATGAGCTGTCCTCGGTATCGTCGTATCCCAC | 27 |
| lacl Primer 1f | ATGAAACCAGTAACGTTATACGATGTCGC | 28 |
| lacl Primer 1r | TCACTGCCCGCTTTCCAG | 29 |
| lacl Primer 2f | GGTATCCACGGAGTCCCAGCAGCCATGAAACCAGTAAC GTTAT | 30 |
| Primer1fAge | CTGGAGCACCTGCCTGAAATCAC | 31 |
| Primer1fXba | CGCGTGCGCCAATTCTGCAGACAAATG | 32 |
| Primer1r | TGCTGGGACTCCGTGGATACCGACCTTCCGCTTC | 33 |
| Primer2f | GGTATCCACGGAGTCCCAGCAGCCGTGAAACCAGTAAC GTTAT | 34 |
| Primer2r | GGCGGACTCTGAGGTCCCGGGAGTCTCGCTGCCGCTCT GCCCGCTTTCCAG | 35 |
| Primer3f | CGGGACCTCAGAGTCCGCCACACCCGAAAGTGACAAGA AGTACAGCATC | 36 |
| Primer3r | CGTCCACCTTGGCCATCTCGTTGCTG | 37 |
| lacOsymCF 1f | GTTCGGAATATAAATTGTGAGCGCTCACAATTAAGCTTG CAGAGTACCTGAAACAGGA | 38 |
| lacOsymCF 5r | GTTCGGAATATAAATTGTGAGCGCTCACAATTAAGCTTCA TTCACAGTAGCTTACCCA | 39 |
| lacOsymCF 5kf | GTTCGGAATATAAATTGTGAGCGCTCACAATTAAGCTTG CTGTGCATTTTCCTCTGGGT | 40 |

TABLE 2-continued

| PCR Primer DNA Sequences. | | |
|---|---|---|
| Primer | Sequence | SEQ ID NO |
| lacOsymCF 5kr | GTTCGGAATATAAATTGTGAGCGCTCACAATTAAGCTTCA AGACGTTGTGTTAGGTACATTACATGTAC | 41 |
| pUC19poly CF5kr | GAATTCGAGCTCGGTACCCGGGGATCCCAAGACGTTGT GTTAGGTACATTACATGTAC | 42 |
| pUC19poly CF5r | GAATTCGAGCTCGGTACCCGGGGATCCCATTCACAGTA GCTTACCCA | 43 |
| tetoCF5kf | CACTCCCTATCAGTGATAGAGAAAAGAAAGCTGTGCATT TTCCTCTGGGT | 44 |
| tetoCF5kr | CACTCCCTATCAGTGATAGAGAAACAAGACGTTGTGTTA GGTACATTACATGTACATC | 45 |
| tetoCF1f | CACTCCCTATCAGTGATAGAGAAAAGGCAGAGTACCTGA AACAGGA | 46 |
| tetoCF5r | CACTCCCTATCAGTGATAGAGAAAAGCATTCACAGTAGC TTACCCA | 47 |
| 10635f | CGGAGCCTATGGAAAAACGCCAGC | 48 |

Construction of the lactose repressor-Cas9 fusion was performed as outlined in FIG. 8. Three overlapping DNA fragments amplified by polymerase chain reaction with the Q5 high fidelity polymerase were cloned into AgeI/BglII digested pSpCas9 BB-2A-GFP(px458) (Genescript, Inc) to generate the GeneTether lactose repressor-Cas9 fusion plasmid pGT1 (FIG. 8D, SEQ ID NO 63) using the NEBuilder system (New England Biolabs). The three, polymerase chain reaction products used for this assembly were generated using the polymerase chain reaction primers to the px458 vector Primer1fAge/Primer1r, and Primer3f/Primer3r, and the BbsI-inactivated Lactose repressor gene was amplified using Primer2f/Primer2r (Table 2). The resulting plasmid, pGT1, was screened for by colony polymerase chain reaction and the Lactose repressor-Cas9 fusion gene sequence was confirmed by DNA sequencing (Quintara Biosciences), restriction endonuclease mapping, and diagnostic polymerase chain reaction amplification.

Construction of Tetracycline Repressor-Modified Cas9.

Figure 9:
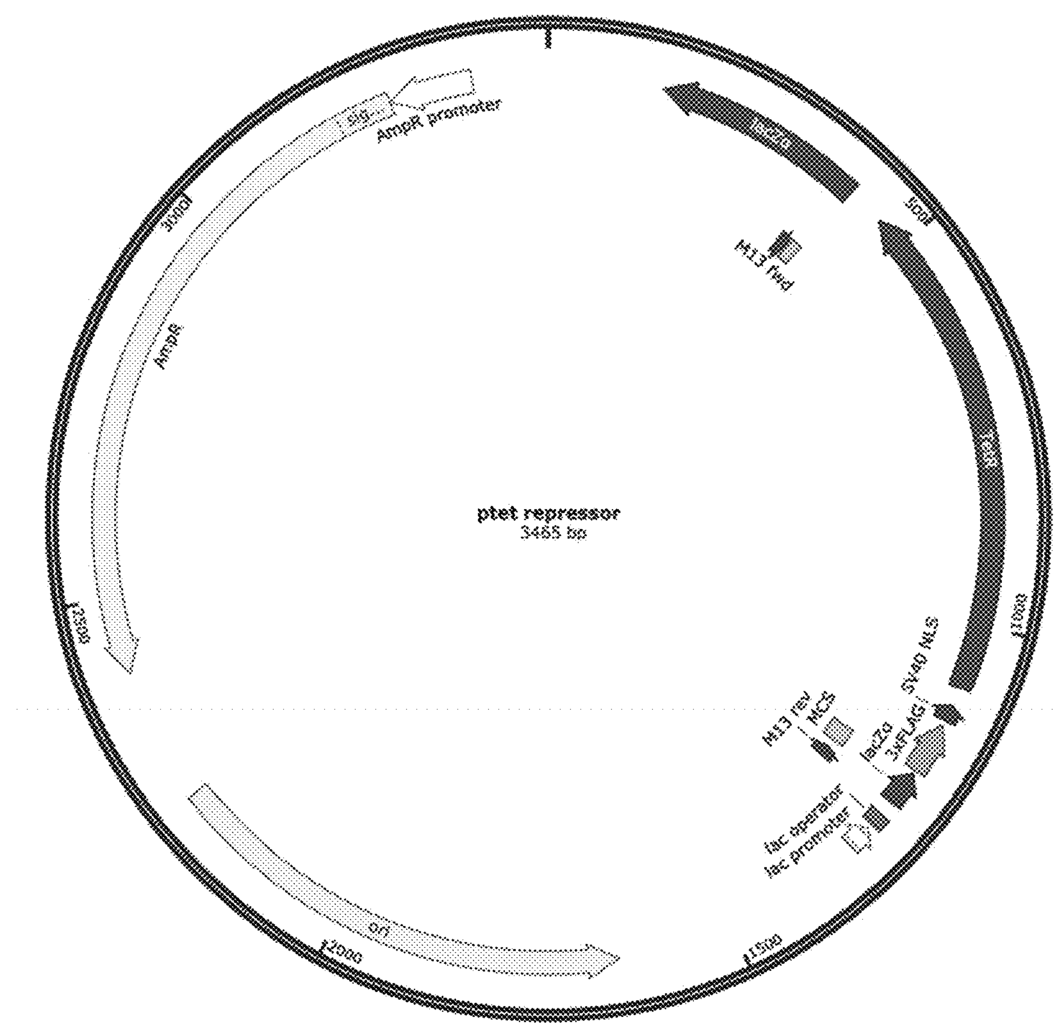
FIG. 9 is a vector map of the ptet repressor plasmid used in the construction of pGT9.
Figure 10A:
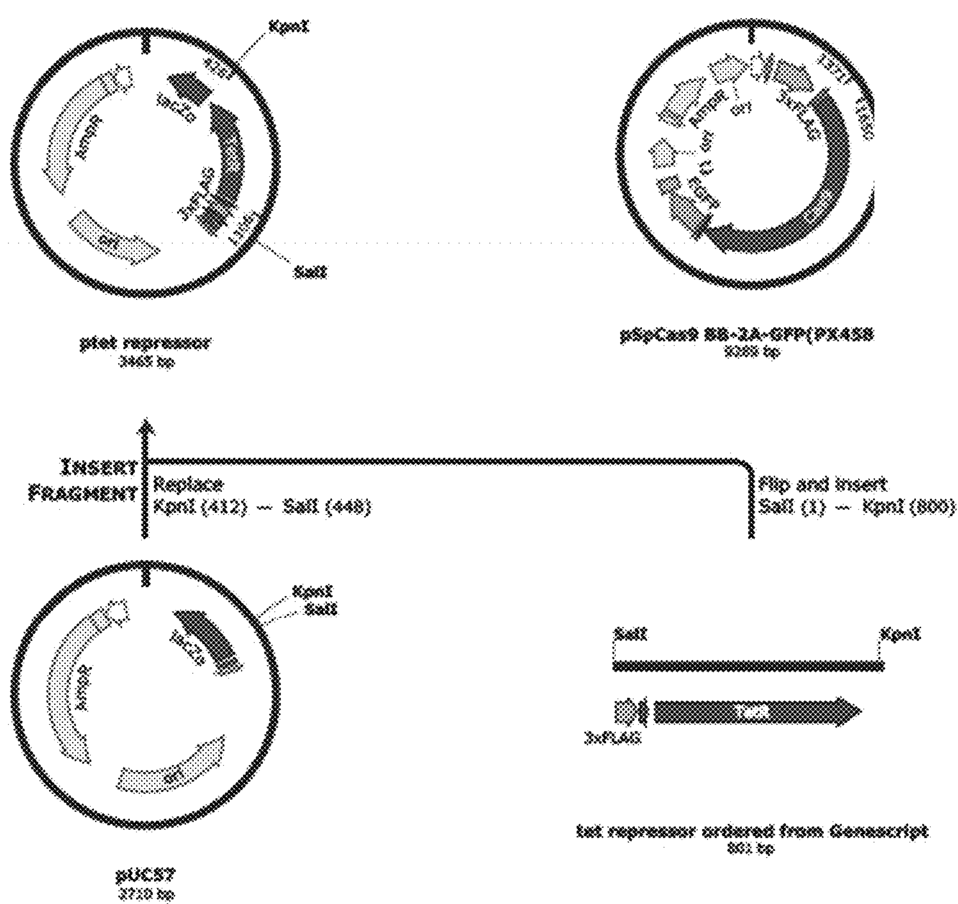
FIG. 10A is a workflow diagram for the construction of pGT9. A tet repressor cassette was cloned into pUC57 to create ptet repressor.
Figure 10B:
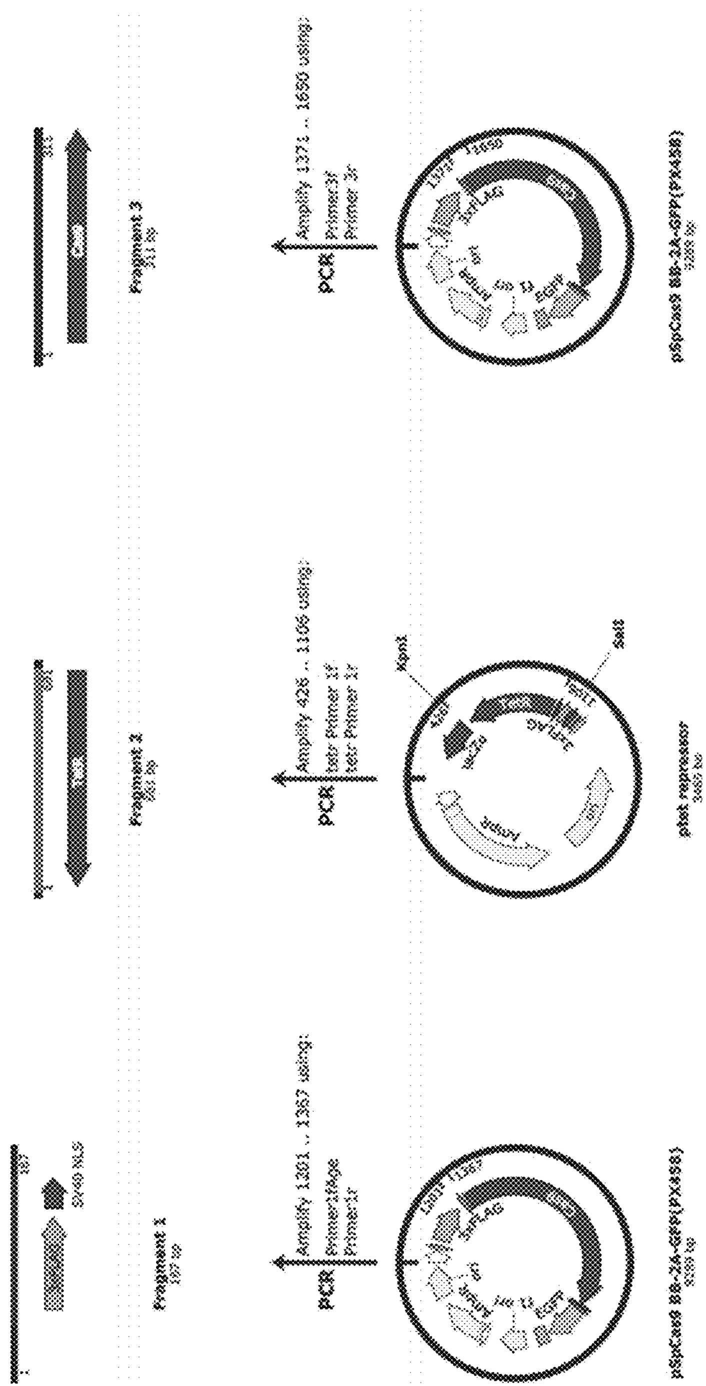
FIG. 10B is a workflow diagram for the construction of pGT9. Three polymerase chain reaction products, Flag/SV40 NLS, lacI and Cas9, were generated.
Figure 10C:
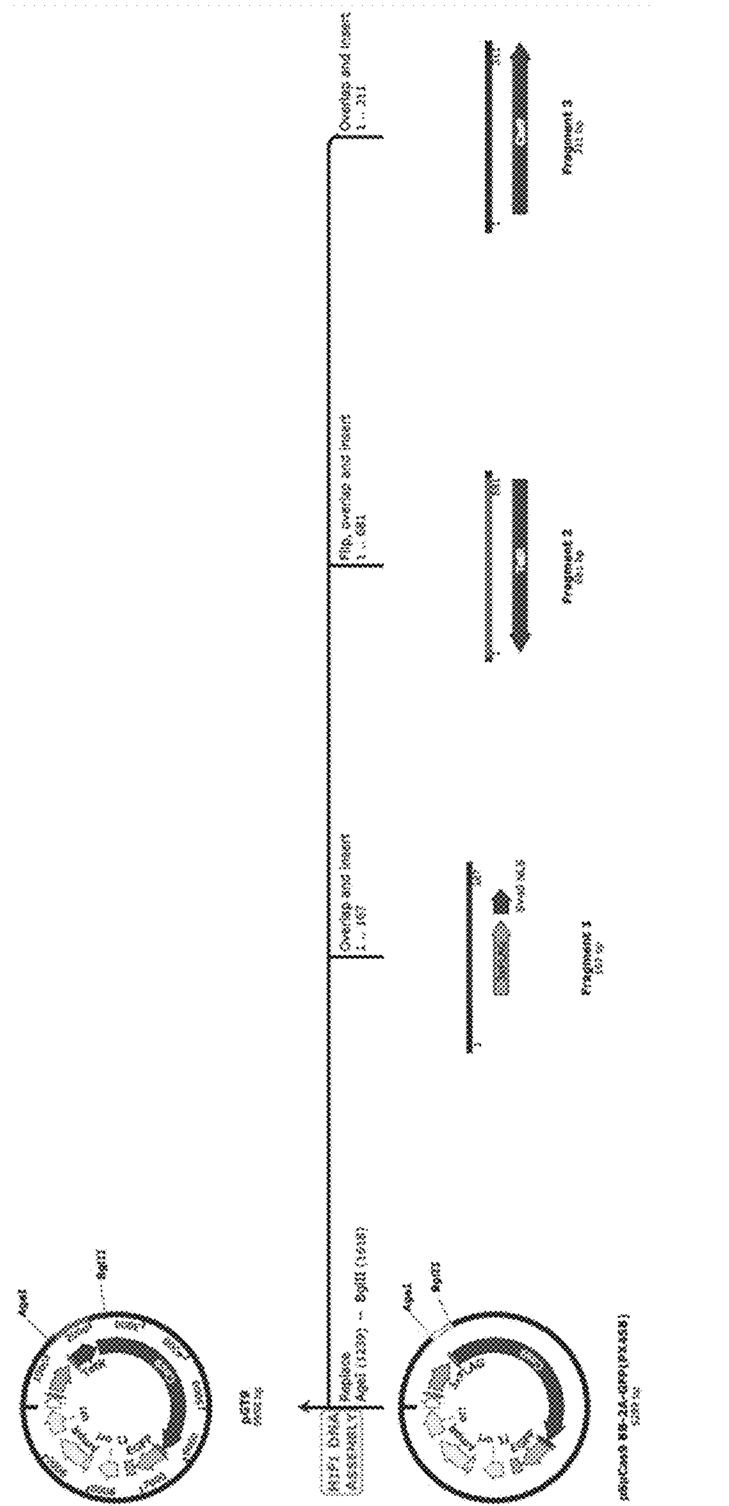
FIG. 10C is a workflow diagram for the construction of pGT9. Three polymerase chain reaction products, Flag/SV40 NLS, lacI and Cas9 were cloned into pSpCas9 BB-2A-GFP(px458).
Figure 10D:
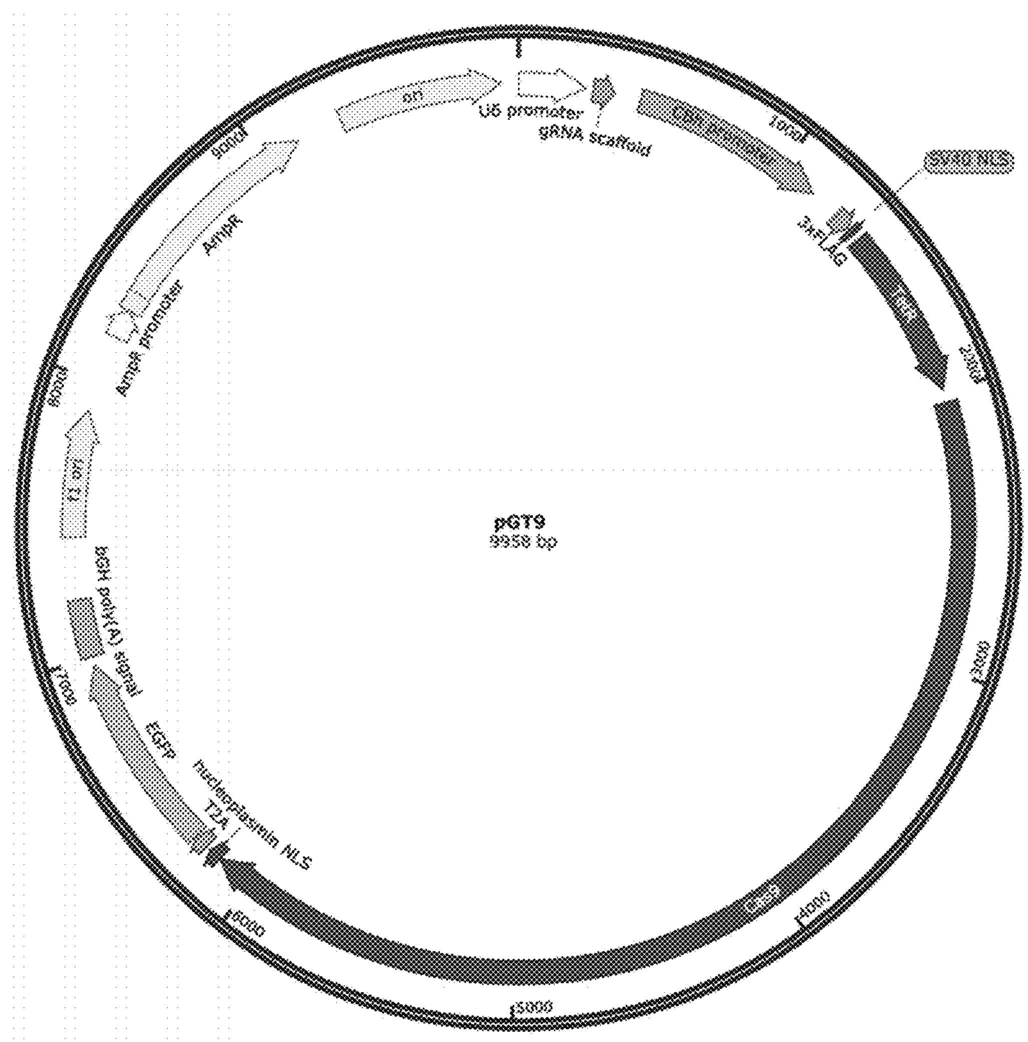
FIG. 10D is a vector map of pGT9.

The gene encoding the class B TN10 tetracycline repressor, with human codon preference, was ordered as a synthetic DNA molecule (Genescript, Inc) cloned into the pUC57 vector (FIG. 9 and SEQ ID NO: 65). Construction of the tetracycline-repressor-Cas9 fusion was performed similar to the pGT1 lactose repressor-Cas9 fusion (FIG. 10). The three, polymerase chain reaction products used for this assembly were generated using the polymerase chain reaction primers to the px458 vector Primer1fAge/Primer1r, and Primer3f/Primer3r, and the Tetracycline repressor gene was amplified using the primers NLS Linker primer1f/tet linker Cas9 Primer 1r. The resulting plasmid, pGT9 (SEQ ID NO: 63), was screened for by colony polymerase chain reaction and the Tetracycline repressor-Cas9 fusion gene sequence was confirmed by DNA sequencing (Quintara Biosciences), restriction endonuclease mapping, and diagnostic polymerase chain reaction amplification.

Guide RNA Cloning Guide RNA sequences were designed to bind the exon 11 gene sequence of the wild type CFTR gene and the CFTR del-F508 mutant gene sequence (Table 3). The guide DNA oligonucleotides were annealed to create duplex molecules with Bbs1 compatible overhang and were subsequently ligated into gel-purified BbsI restriction endonuclease digested px458, pGT1, and pGT9.

TABLE 3

| Guide Sequences. Shown are the DNA oligonucleotides for cloning into the Bbs1 sites in pGT1, pGT9, and pX458 Cas9 vectors | | |
|---|---|---|
| Name | Sequence | SEQ ID NO |
| CFWT 130117 fw | CACCGATTAAAGAAAATATCATCTT | 49 |
| CFWT 130117 fc | AAACAAGATGATATTTTCTTTAATC | 50 |
| CFWT 130121 rw | CACCGAAAGATGATATTTTCTTTAA | 51 |
| CFWT 130121 rc | AAACTTAAAGAAAATATCATCTTTC | 52 |
| delF 130127 fw | CACCGACCATTAAAGAAAATATCAT | 53 |
| delF 130127 fc | AAACATGATATTTTCTTTAATGGTC | 54 |
| delF 130138 rw | CACCGACCAATGATATTTTCTTTAA | 55 |
| delF 130138 rc | AAACTTAAAGAAAATATCATTGGTC | 56 |

aCFTR Donor DNA Generation 5 kilobasepair CFTR DNA fragments approximately centered on the CFTR gene exon 11 were generated by polymerase chain reaction using the Q5 high fidelity DNA polymerase and primers CF96310f and CF101310r. Donor DNA fragments containing the CFTR delF508 mutation were generated using genomic DNA from the CFBE41o-cell line that is homozygous for the delF508 mutation. Donor DNA fragments containing the wild type (nonmutant) CFTR gene sequence were generated using genomic DNA from the HEK293 cell line.

Donor DNA fragments used for gene editing were modified at the 5' or 3' end of the fragment to contain either the lactose operator sequence (AATTGTGAGCGCTCACAATT, SEQ ID NO: 57) or tetracycline operator sequence (CACTCCCTATCAGTGATAGAGAAA SEQ ID NO: 58). To generate 500 base pair donor DNA molecules, polymerase chain reaction amplification using the Q5 high fidelity thermostable DNA polymerase with the primer pairs lacOsymCF1f/CF5r to add the lactose operator sequence to the 5' end of the donor DNA or primer pairs Cf1f/lacOsymCF5r to add the lactose operator to the 3' end of the donor DNA fragment (Figure Donor DNA Molecules). Donor DNA molecules with the tetracycline operator sequence were generated using the primer pairs tetoCF1f/CF5r and CF1f/tetoCF5r. Donor DNA fragments were gel-purified prior to use in cell transfections for gene editing.

Cell Transfection with Px458, pGT1, pGT9 Cas9 Vectors and 500 Base Pair Donor DNA Fragments HEK293 cells were transfected in 12-well plates using Lipofectamine 3000 (Invitrogen, Inc) with 500 ng of plasmid DNA and 500 ng of gel purified donor DNA fragments. The px458, pGT1, and pGT9 plasmids contain a green fluorescent protein reporter gene that is expressed in transfected cells and allows monitoring of transfection efficiencies. Green fluorescent protein expression was visualized by fluorescence microscopy at approximately 48 hours post transfection. At 48-72 hours post transfection, 12-well plates of transfected cells were washed once with phosphate buffered saline and stored at −80° C. until DNA was harvested for analysis of gene editing efficiencies.

Analysis for the delF508 Mutation by Allele-Specific Polymerase Chain Reaction Analysis The presence of the delF508 mutation in a population of CFTR wild type cells can be detected using polymerase chain reaction with Taq polymerase and the primer pair CF1Bf/CF8Cr. Since the CF1Bf primer is located 5' or outside of the donor DNA fragment, the 388 basepair product is generated from an "inside-out" approach and is specifically diagnostic for gene edited events and will not amplify randomly integrated or unintegrated donor DNA molecules.

Genomic DNA was prepared directly from each well of a 12-well plate (Genejet Genomic Purification Kit, ThermoFisher, Inc) and DNA concentration determined by ultraviolet spectroscopy. Allele specific polymerase chain reactions were performed on 100 ng of genomic DNA and 500 μM primer, 1.5 mM $MgCl_2$, HotStart Taq polymerase (New England Biolabs). The thermocycler program for semiquantitative amplification of the delF508 mutant DNA sequence was 95° C., 2 minutes; 35 cycles of 95° C., 30 seconds, 50° C., 30 seconds, 72° C., 1 minute; followed by 72° C., 8 minutes. The 388 base pair polymerase chain reaction product was visualized with ultraviolet light on a 1.5% agarose gel stained with Gelred (Biotium, Inc). For semi-quantification of the PCR product, standard genomic DNA samples with varying ratios of wild type and delF508 mutant DNA were amplified in parallel to experimental DNA samples.

Cell Transfection

Figure 11:
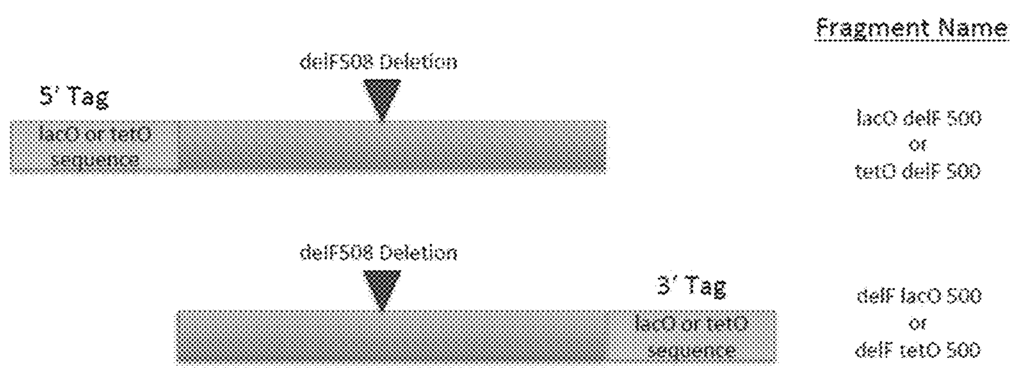
FIG. 11 is an overview of a donor fragment, showing a 500 pase pair donor fragment with delF508 Mutation and lacO or tetO Recognition Sequences
Figure 12:
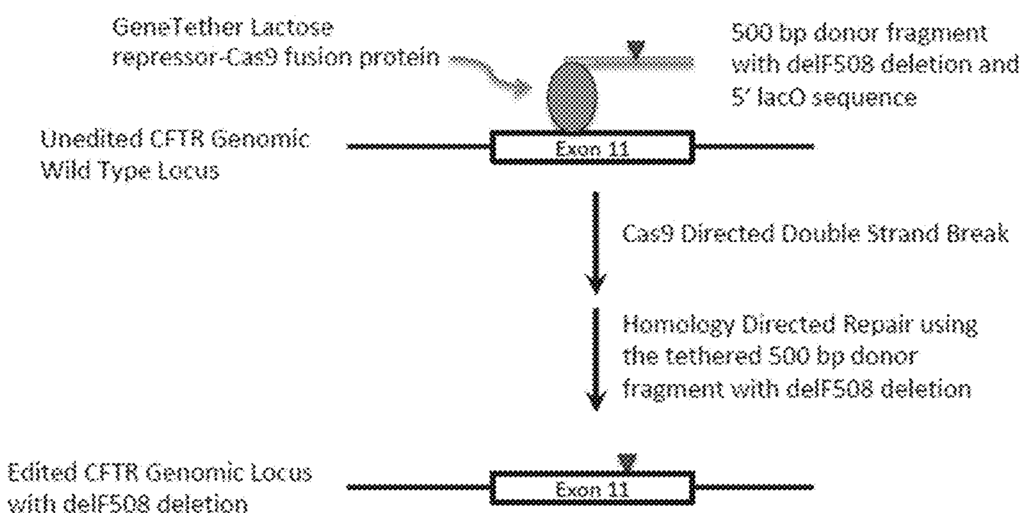
FIG. 12 is an overview of the use of the compositions described herein for homology directed repair by homologous recombination between the genomic CFTR target Cas9-induced double strand break and donor fragment to catalyze transfer of the delF508 DNA sequence to the genomic target.

Two different tethers (lactose-repressor-Cas9 fusion or tetracycline repressor-Cas9 fusion) were used in combination with donor DNA molecules containing a 5' lactose or tetracycline operator sequence or a 3' lactose or tetracycline operator sequence (FIGS. 11 and 12) and containing the delF508 deletion sequence. Homology directed repair by homologous recombination between the genomic CFTR target Cas9-induced double strand break and donor fragment would catalyze transfer of the delF508 DNA sequence to the genomic target (FIG. 12).

Cas9 guides complementary to the nonmutated wild type CFTR exon 11 DNA sequence, but not to the delF508 DNA sequence were selected to allow recognition of the genomic DNA target and prevent the Cas9 enzyme from recognizing, and cleaving, the delf508 donor DNA fragment.

Approximately $5\times10^5$ HEK293 cells per well were seeded, 24 hours before transfection, into Corning 12-well tissue culture plates such that the wells were 50-80% confluent at the time of transfection. The media on the cells was changed prior to transfection.

For transfections, 500 ng of px458, pGT1 or pGT9 was mixed with 500 ng of donor DNA fragment in 50 μL of DMEM medium. 2 μL of the P3000 reagent was then added to the DNA/DMEM solution, mixed well, and allowed to incubate at room temperature for 5 minutes. A solution of Lipofectamine 3000 was made by adding 1.5 μL of undiluted Lipofectamine 3000 to 50 μL. of DMEM and equal volumes of DNA/DMEM solutions and Lipofectamine/DMEM solutions were mixed and incubated at room temperature for 12-15 minutes. 100 μL of the DNA/P3000/Lipofectamine solution was then added per well of Corning 12-well plates. Two days after transfection the cells are examined with fluorescent microscopy to assess the extent of successful transfection.

GeneTethers Increase Gene Editing Efficiency

Several variables for the effect of GeneTether modified Cas9 vectors on gene editing efficiency were tested: a lactose repressor-Cas9 fusion protein, tetracycline repressor-Cas9 fusion protein, Cas9 guides complementary to the top or bottom strand of genomic target, and 500 bp donor DNA molecules containing the delF508 deletion with the lactose operator sequence at the 5' or 3' end of the donor DNA fragment.

Figure 13:
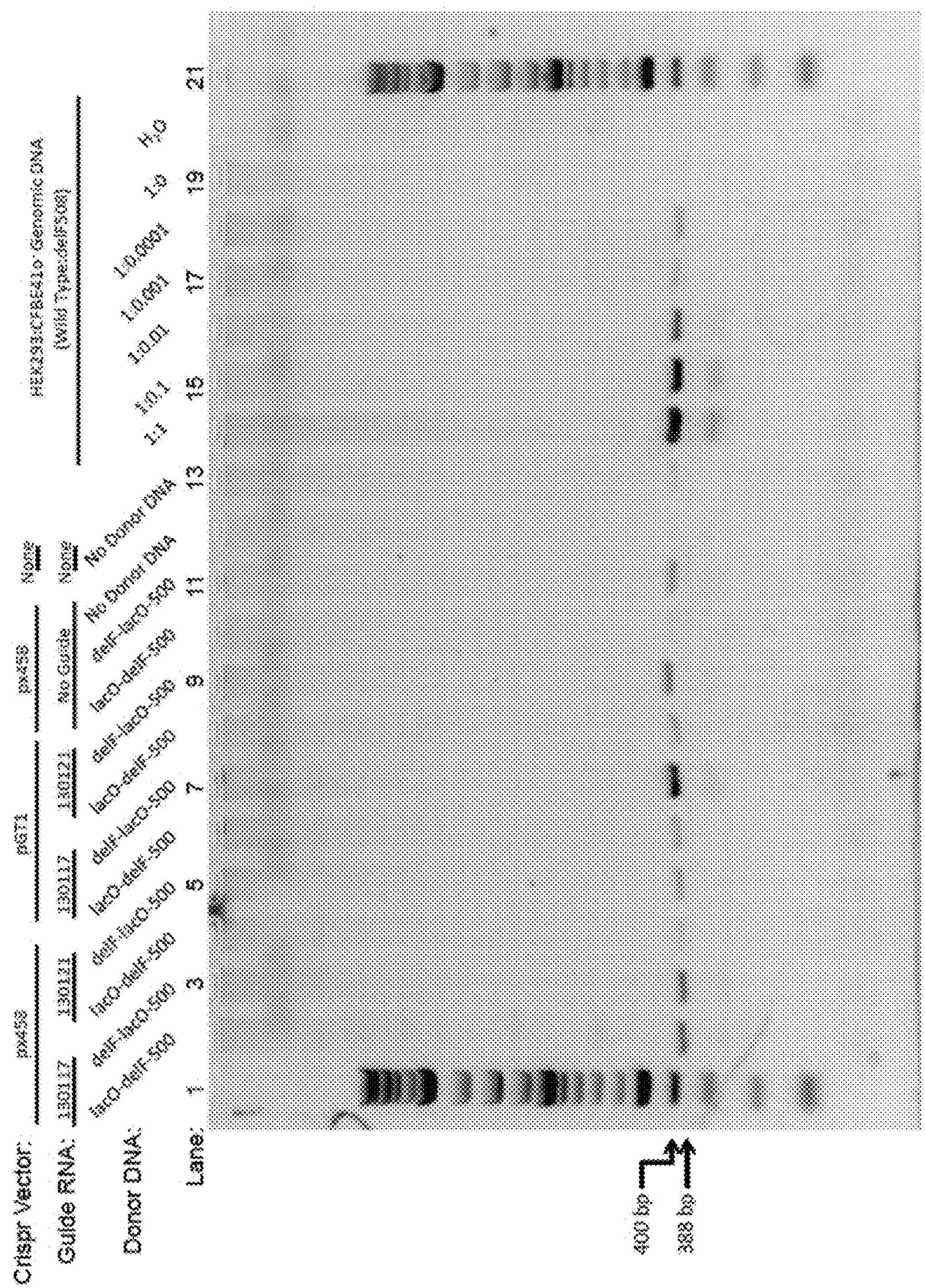
FIG. 13 illustrates that combination of pGT1 vector (lactose repressor-Cas9 fusion) with the 130117 guide (genomic target forward strand) and lactose operator on the 3' end of donor DNA (FIG. 13, lane 7) demonstrates higher gene editing efficiency as compared to the px458 vector with unmodified Cas9 and same donor DNA fragment

The combination of pGT1 vector (lactose repressor-Cas9 fusion) with the 130117 guide (genomic target forward strand) and lactose operator on the 3' end of donor DNA (FIG. 13, lane 7) demonstrates higher gene editing efficiency as compared to the px458 vector with unmodified Cas9 and same donor DNA fragment (compare 388 basepair products lane 3 and lane 7, FIG. 13. Measurement of band intensities using ImageJ software (imagej.nih.gov) indicates that the tethered donor DNA complex has an approximate 7-fold higher gene editing efficiency compared to the px458 unmodified Cas9. Indeed, comparison of lane 7 band intensity to the reconstructed mixture of WT:delF508 DNA (lanes 14-19) suggests the delF508 mutation is present in approximately 10% of the genomic DNA. Since transfection efficiencies for these experiments were 10%, or less, up to 100% of cells transfected with the combination of pGT1/130117guide/3' lactose operator sequence underwent successful gene editing.

Other combinations of pGT1/guide/donor DNA performed equal to or, slightly better than, unmodified Cas9 (FIG. 13; lane 9 vs lane 5) for gene editing, demonstrating that the Cas9 protein activity was not affected by the lactose repressor fusion. The placement of the lactose operator sequence may slightly favor the 3' placement (FIG. 13; lanes 7 and 9 vs lanes 3 and 5). Donor DNA transfected with px458 not containing guide sequence showed low levels of gene editing (FIG. 13; lanes 10 and 11). Some faint 388 bp product is evident in lanes 10, 12, and 13 that is likely due to artifactual low-level mispriming of PCR primers used for the allele-specific PCR.

Figure 14:
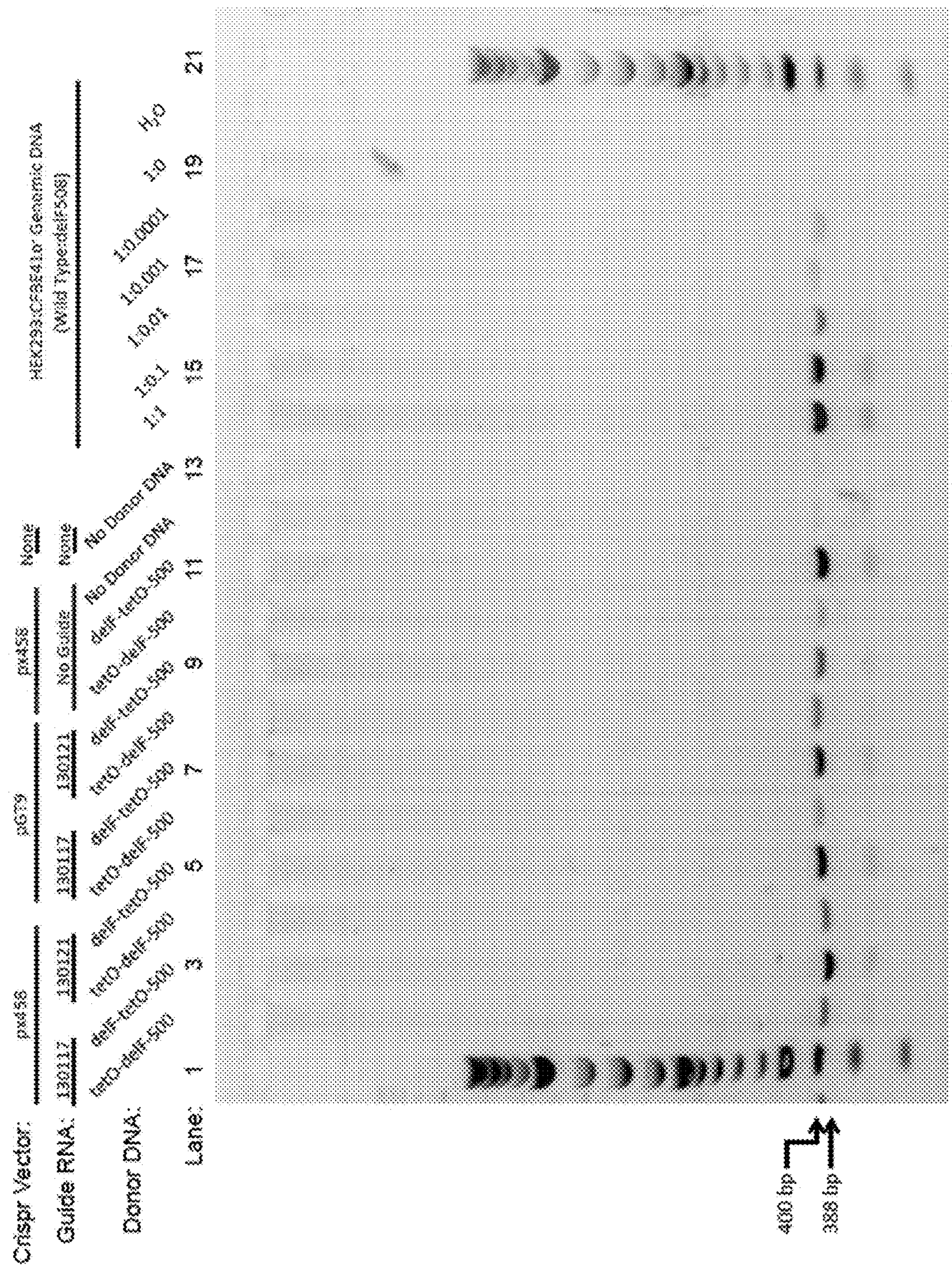
FIG. 14 illustrates that gene editing with the pGT9 tetracycline repressor-Cas9 fusion vector, guide sequences, and donor fragments did not yield appreciably better gene editing frequencies than the control px458 vector

Gene editing with the pGT9 tetracycline repressor-Cas9 fusion vector, guide sequences, and donor fragments did not yield appreciably better gene editing frequencies than the control px458 vector (FIG. 14, lanes 2-5 vs lanes 6-9). The placement of the tetracycline at the 3' end of the donor DNA fragment appears to result in slightly better gene editing efficiencies (FIG. 14 lanes 2, 4, 6, 8 vs lanes 3, 5, 7) similar to placement of the lactose operator sequence.

These results demonstrate that the GeneTether lactose repressor-Cas9 fusion protein encoded by pGT1 can significantly increases gene editing efficiency as compared to the unmodified Cas9 found in the px458 vector. Indeed, it is possible that the combination of pGT1/130117 guide/delF508 lacO 500 successfully caused gene editing of WT to delF508 in almost 100% of transfected cells.

The invention claimed is:

1. A composition for tethering donor DNA to a nuclease, the composition comprising a nucleic acid comprising donor DNA and a consensus sequence for a DNA binding domain; and at least one of:

a fusion protein a fusion protein comprising a nuclease and further comprising a DNA binding domain for binding the consensus sequence, wherein the DNA binding domain consists of amino acids 43-403 of SEQ ID NO: 9; and a nucleic acid encoding the fusion protein.

2. The composition of claim 1 wherein the nuclease is a Cas protein, a Transcription activator-like effector nuclease (TALEN), a meganuclease, or a Zinc Finger.

3. The composition of claim 1 wherein the nuclease is a Cas protein.

4. The composition of claim 3 wherein the Cas protein is Cas9.

5. The composition of claim 1 wherein the fusion protein further comprises a nuclear localization sequence.

6. The composition of claim 2, further comprising a guide RNA that interacts with the Cas protein and a target DNA sequence.

7. The composition of claim 1 wherein the consensus sequence comprises a Lac operator.

8. The composition of claim 7 wherein the consensus sequence comprises a sequence with at least 80%, 85%, 90%, 95% or at least 99% identity to the Lac operator as set forth in SEQ ID NO: 66.

9. The composition of claim 1 wherein the nuclease is coupled to the DNA binding domain via a linker.

10. The composition of claim 9 wherein the linker comprises a sequence selected from any one of SEQ ID NOs: 3 to 7, a GGS linker, or amino acids 404-419 of SEQ ID NO: 9.

11. The composition of claim 1 wherein the fusion protein comprises a LAC repressor and a Cas9.

12. The composition of claim 1 comprising a vector, wherein either or both of:

a. the nucleic acid comprising the donor DNA and the consensus sequence for a DNA binding domain; and b. the nucleic acid encoding the fusion protein, are present in a vector.

13. The composition of claim 12 wherein the vector further comprises a nucleic acid sequence encoding a guide RNA that interacts with the Cas protein and a target DNA sequence.

14. The composition of claim 1 wherein the nuclease is modified to reduce or eliminate nuclease activity.

15. A kit comprising:

a nucleic acid comprising donor DNA and a consensus sequence for a DNA binding domain; and at least one of a fusion protein a fusion protein comprising a nuclease and further comprising a DNA binding domain for binding the consensus sequence, wherein the DNA binding domain consists of amino acids 43-403 of SEQ ID NO: 9; and a nucleic acid encoding the fusion protein.

16. The kit of claim 15 wherein the nuclease is a Cas protein, a Transcription activator-like effector nuclease (TALEN), a meganuclease, or a Zinc Finger.

17. The kit of claim 16 wherein the Cas protein is Cas9.

* * * * *